United States Patent
Yu et al.

(10) Patent No.: US 9,200,279 B2
(45) Date of Patent: Dec. 1, 2015

(54) METHODS AND COMPOSITIONS FOR THE TREATMENT OF CANCER OR OTHER DISEASES

(71) Applicant: CITY OF HOPE, Duarte, CA (US)

(72) Inventors: Hua Yu, Glendora, CA (US); Marcin Kortylewski, Monrovia, CA (US); Richard Jove, Glendora, CA (US); Piotr Marek Swiderski, San Dimas, CA (US); John J. Rossi, Alta Loma, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/154,833

(22) Filed: Jan. 14, 2014

(65) Prior Publication Data
US 2014/0128324 A1    May 8, 2014

Related U.S. Application Data

(60) Division of application No. 13/229,146, filed on Sep. 9, 2011, now Pat. No. 8,748,405, which is a continuation-in-part of application No. 12/879,199, filed on Sep. 10, 2010, now abandoned, which is a continuation-in-part of application No. 11/966,423, filed on Dec. 28, 2007, now abandoned.

(60) Provisional application No. 61/241,764, filed on Sep. 11, 2009, provisional application No. 60/897,495, filed on Jan. 26, 2007, provisional application No. 61/466,086, filed on Mar. 22, 2011.

(51) Int. Cl.
| | |
|---|---|
| *C07H 21/02* | (2006.01) |
| *C07H 21/04* | (2006.01) |
| *A61K 48/00* | (2006.01) |
| *C12N 15/11* | (2006.01) |
| *C12N 15/113* | (2010.01) |
| *A61K 31/7105* | (2006.01) |

(Continued)

(52) U.S. Cl.
CPC ............ *C12N 15/113* (2013.01); *A61K 31/713* (2013.01); *A61K 31/7105* (2013.01); *A61K 47/481* (2013.01); *A61K 47/48092* (2013.01); *C07H 21/02* (2013.01); *C07K 14/47* (2013.01); *C12N 15/1135* (2013.01)

(58) Field of Classification Search
USPC .................................. 514/44; 536/23.1, 24.5
See application file for complete search history.

(56) References Cited

U.S. PATENT DOCUMENTS

| | | | |
|---|---|---|---|
| 6,159,694 | A | 12/2000 | Karras |
| 6,692,959 | B2 | 2/2004 | Bennett et al. |

(Continued)

FOREIGN PATENT DOCUMENTS

| | | |
|---|---|---|
| WO | 2006096754 A2 | 9/2006 |
| WO | 2007143086 A2 | 12/2007 |

OTHER PUBLICATIONS

Chu, T.C. et al., "Aptamer Mediated siRNA Delivery," Nucleic Acids Research, Jan. 1, 2006, vol. 34, No. 10, E73 (pp. 1-6), XP-002579007, copyright 2006 The Author(s).

(Continued)

*Primary Examiner* — Terra C Gibbs
(74) *Attorney, Agent, or Firm* — Rothwell, Figg, Ernst & Manbeck P.C.

(57) ABSTRACT

The present invention relates to methods and compositions for the treatment of diseases, including cancer, infectious diseases and autoimmune diseases. The present invention also relates to methods and compositions for improving immune function. More particularly, the present invention relates to multifunctional molecules that are capable of being delivered to cells of interest for the treatment of diseases and for the improvement in immune function.

4 Claims, 51 Drawing Sheets

(51) Int. Cl.
  A61K 31/713    (2006.01)
  A61K 47/48     (2006.01)
  C07K 14/47     (2006.01)

(56) References Cited

U.S. PATENT DOCUMENTS

| | | |
|---|---|---|
| 6,710,174 B2 | 3/2004 | Bennett et al. |
| 2003/0060440 A1 | 3/2003 | Klinman et al. |
| 2004/0097719 A1 | 5/2004 | Agrawal et al. |
| 2004/0198685 A1 | 10/2004 | Agrawal et al. |
| 2005/0130922 A1 | 6/2005 | Altaba et al. |
| 2005/0256071 A1 | 11/2005 | Davis |
| 2006/0127502 A1 | 6/2006 | Yu et al. |
| 2008/0214436 A1 | 9/2008 | Yu et al. |
| 2010/0298409 A1 | 11/2010 | Xie et al. |

OTHER PUBLICATIONS

Maurer, T. et al., "CpG-DNA Aided Cross-Presentation of Soluble Antigens by Dendritic Cells," European Journal of Immunology, Aug. 1, 2002, vol. 32, No. 8, pp. 2356-2364. XP009073688, copyright Wiley-VCH Verlag GmbH, D-69451 Weinhelm, 2002.

EP extended search report, Reference—HB/P41762EP; Application No./Patent No. 07868108.7-1453/2125855 PCT/US2007026432; Applicant—City of Hope, 9 pages.

Hoene, V. et al., "Human monocyte-derived dendritic cells express TLR9 and react directly to the CpG-A oligonucleotide D19," Journal of Leukocyte Biology, vol. 80(6), Dec. 2006, pp. 1328-1336, © Society for Leukocyte Biology.

Chiu, Ya-Lin et al., "siRNA function in RNAi: A chemical modification analysis," RNA, vol. 9, No. 9, pp. 1034-1048, © 2003 RNA Society.

PCT International Search Report, Int'l Appln No. PCT/US11/51042, int'l filing date: Sep. 9, 2011, (Earliest) Priority Date: Mar. 22, 2011, Applicant: City of Hope, 6 pages.

Kexiong Zhang et al., "Receptor-mediated delivery of siRNAs by tethered nucleic acid base-paired interactions," RNA (2008), vol. 14:577-583, published by Cold Spring Harbor Laboratory Press, copyright 2008 RNA Society.

Marcin Kortylewski et al., "In vivo delivery of siRNA to immune cells by conjugaton to a TLR9 agonist enhances antitumor immune responses," Nature Biotechnology, vol. 27(10):925-932, Oct. 2009.

Non-Final Office Action dated Oct. 15, 2008, 38 pages, U.S. Appl. No. 11/966,423, filed Dec. 28, 2007; Response filed Mar. 12, 2009, 10 pages.

Final Office Action dated Dec. 24, 2009, 35 pages, U.S. Appl. No. 11/966,423, filed Dec. 28, 2007; Response filed May 7, 2010, 10 pages.

Non-Final Office Action dated May 27, 2010, 13 pages, U.S. Appl. No. 11/966,423, filed Dec. 28, 2007; Response filed Nov. 18, 2010, 10 pages.

Non-Final Office Action dated Feb. 3, 2011, 14 pages, U.S. Appl. No. 11/966,423, filed Dec. 28, 2007; No response filed to date.

Vollmer et al., Oligonucleotides, 2004, vol. 14:23-31.

McNamara et al., Nature Biotechnology, 2006, vol. 24:1005-1015.

Nesterova et al., Clinical Cancer Research, 2005, vol. 11(16):5950-5955.

Scanlon, KJ, Current Pharmaceutical Biotechnoiogy, 2004, vol. 5:415-420.

Kortylewski, M. et al., "Inhibiting Stat3 signaling in the hematopoietic system elicits multicomponent antitumor immunity," Nature Medicine, vol. 11, No. 12, Dec. 2005.

Kortylewski, M. et al., "Targeting STAT3 affects melanoma on multiple fronts," Cancer and Metastasis Reviews, 24: 315-327, 2005, © 2005 Springer Science and Business Media.

Li, Long-Cheung et al., "Small dsRNAS induce transcriptional activation in human cells," PNAS, Nov. 14, 2008, vol. 103, No. 46, pp. 17337-17342.

Kuwabara T. et al., "The NRSE smRNA specifies the fate of adult hippocampal neural stem cells," Nucleic Acids Symposium Series No. 49, pp. 87-88, © 2005 Oxford University Press.

Santulli-Marotto, S. et al., "Multivalent RNA Aptamers That Inhibit CTLA-4 and Enhance Tumor Immunity," Cancer Research 63, pp. 7483-7489, Nov. 1, 2003.

Janowski, B.A. et al, "Activating gene expression in mammalian cells with promoter-targeted duplex RNAs," Nature Chemical Biology, vol. 3, No. 3, Mar. 2007.

Yu, Hua et al., "The Stats of Cancer—New Molecular Targets Come of Age;" Nature Reviews, Cancer, vol. 4, Feb. 2004, © 2004 Nature Publishing Group.

Yu, Hua et al., "Crosstalk between cancer and immune cells: role of STAT3 in the tumor microenviroment," Nature reviews, Immunology, vol. 7, Jan. 2007, © 2007 Nature Publishing Group.

News Feature, "Hitting the on switch," Nature, vol. 448, Aug. 23, 2007, pp. 855-858, © Nature Publishing Group.

Morris, K.V. et al., "Small Interfering RNA-Induced Transcriptional Gene Silencing in Human Cells," Science, vol. 305, Aug. 27, 2004, pp. 1289-1292 and 14 supplemental pages.

Hammond, S.M., "Post-Transcriptional Gene Silencing by Double-Stranded RNA," Reviews, Feb. 2001, vol. 2, pp. 110-119, © Macmillan Magazines Ltd.

Furumoto, K. et al., "Induction of potent antitumor immunity by in situ targeting of intratumoral DCs," The Journal of Clinical Investigation, vol. 113, No. 5, Mar. 2004, pp. 774-783.

Hemmi, H. et al., "A Toll-like receptor recognizes bacterial DNA," Nature, vol. 408, Dec. 2000, pp. 740-745.

Kreig, A.M., "CpG motifs: the active ingredient in bacterial extracts?," Nature Medicine, vol. 9, No. 7, Jul. 2003, pp. 831-835.

Latz E. et al., "TLR9 signals after translocating fom the ER to CpG DNA in the lysosome," Nature Immunology, vol. 5, No. 2, Feb. pp. 190-198.

Vicari, A.P., "Reversal of tumor-induced dendritic cell paralysis by CpG immunostimulatory oligonucleotide and anti-interieukin 10 receptor antibody," J. Exp. Med., vol. 196, No. 4, pp. 541-549.

Yasuda, K., "Endosomal translocation of vertebrate DNA activates dendritic cells via TLR9-dependet and -independent pathways," The Journal of Immunology, vol. 174, 2005, pp. 6129-6136.

Yu, D. et al., "'Immunomers'—novel 3'-3'-linked CpG oligodeoxyribonucleotides as potent immunomodulatory agents," Nucleic Acids Research, vol. 30, No. 20, 2002, pp. 4460-4469.

Non-final Office Action dated Oct. 15, 2008, in U.S. Appl. No. 11/966,423, 15 pages.

Final Office Action dated Dec. 24, 2009, in U.S. Appl. No. 11/966,423, 17 pages.

Non-final Office Action dated May 27, 2010, in U.S. Appl. No. 11/966,423, 13 pages.

Final Office Action dated Feb. 3, 2011, in U.S. Appl. No. 11/966,423, 14 pages.

Amendment in response to Office Action dated Oct. 15, 2008, in U.S. Appl. No. 11/966,423, 10 pages.

Amendment in response to Office Action dated Dec. 24, 2009, in U.S. Appl. No. 11/966,423, 10 pages.

Amendment in response to Office Action dated May 27, 2010, in U.S. Appl. No. 11/966,423, 10 pages.

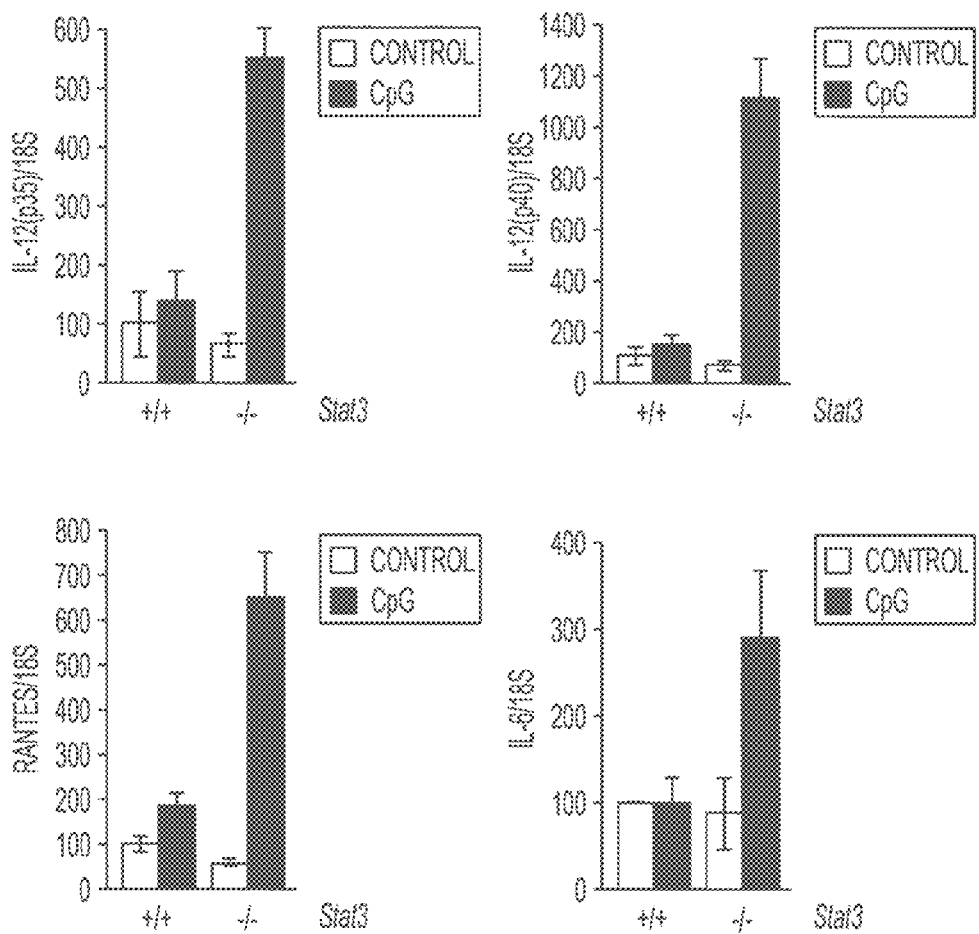
FIG. 1f
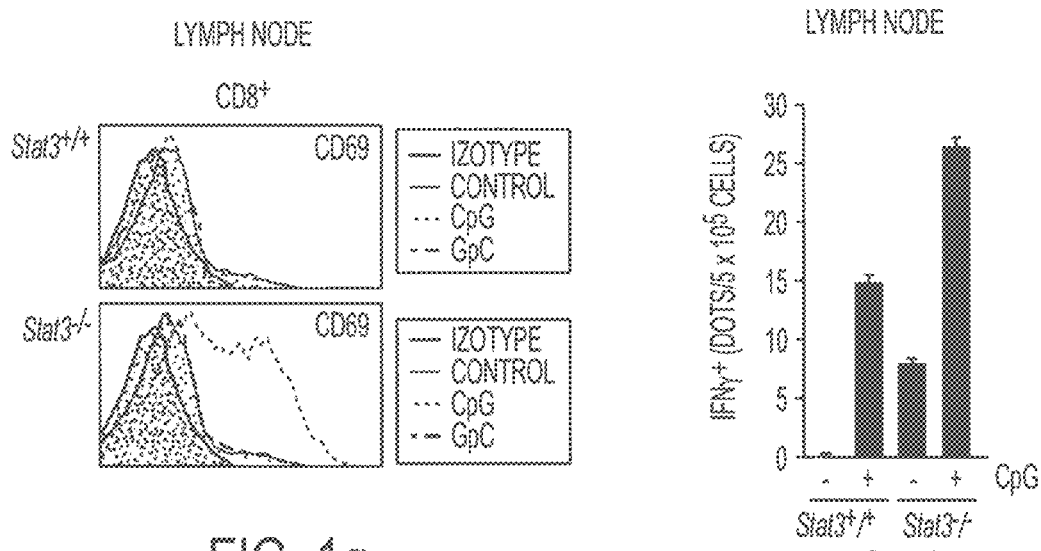
FIG. 1g
FIG. 1h

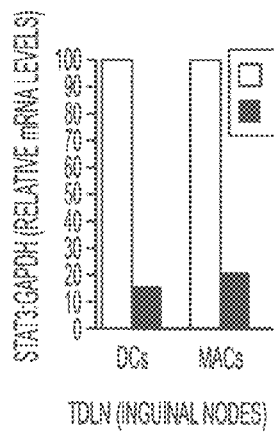
FIG. 3b
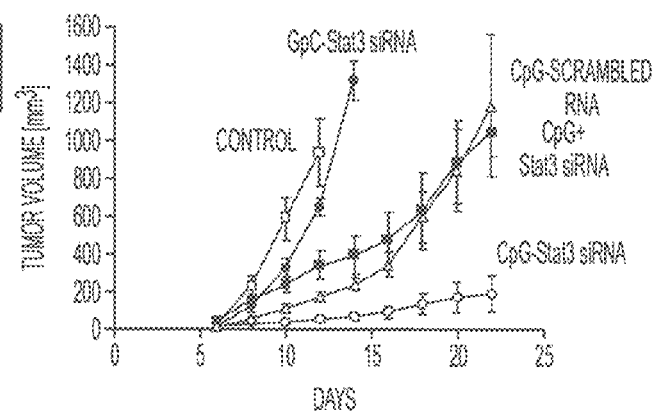
FIG. 3c
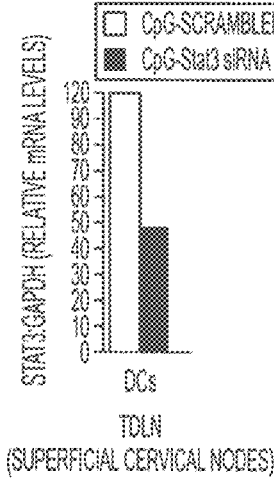
FIG. 3d
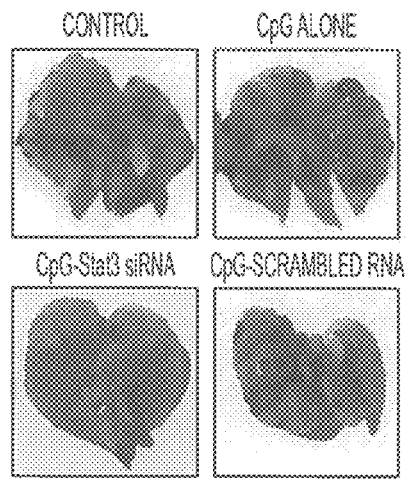
FIG. 3e
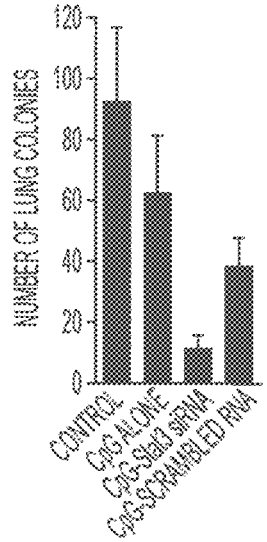

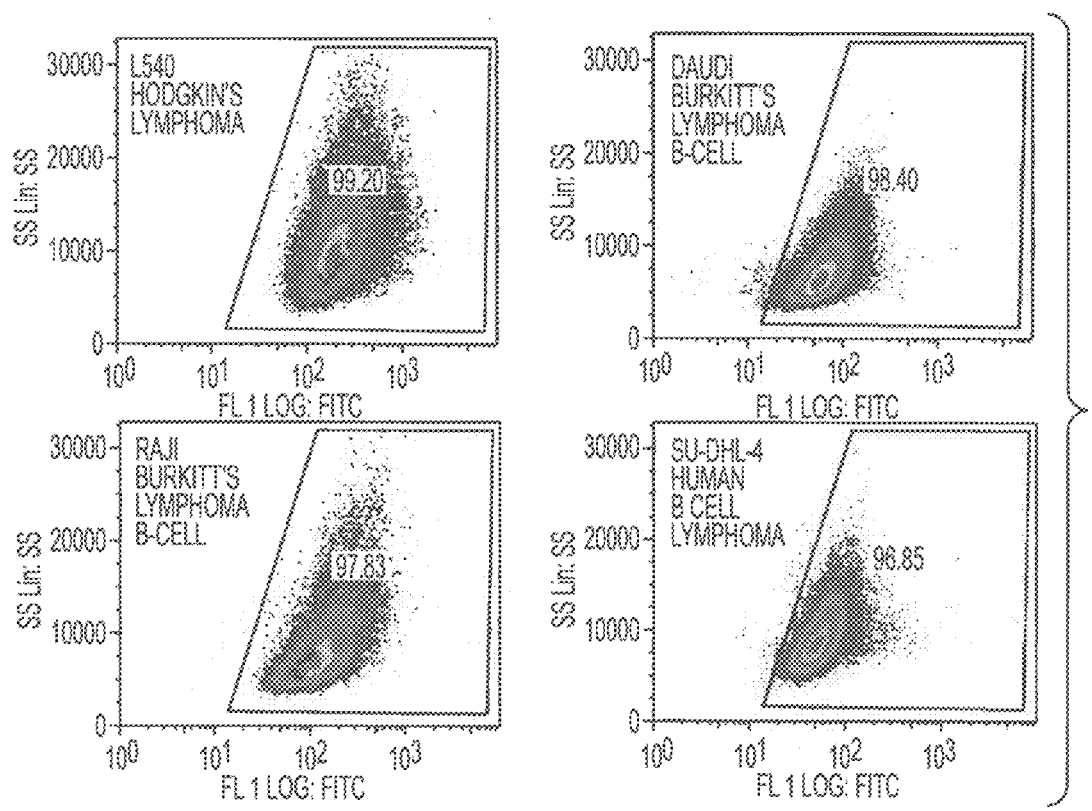
FIG. 5b
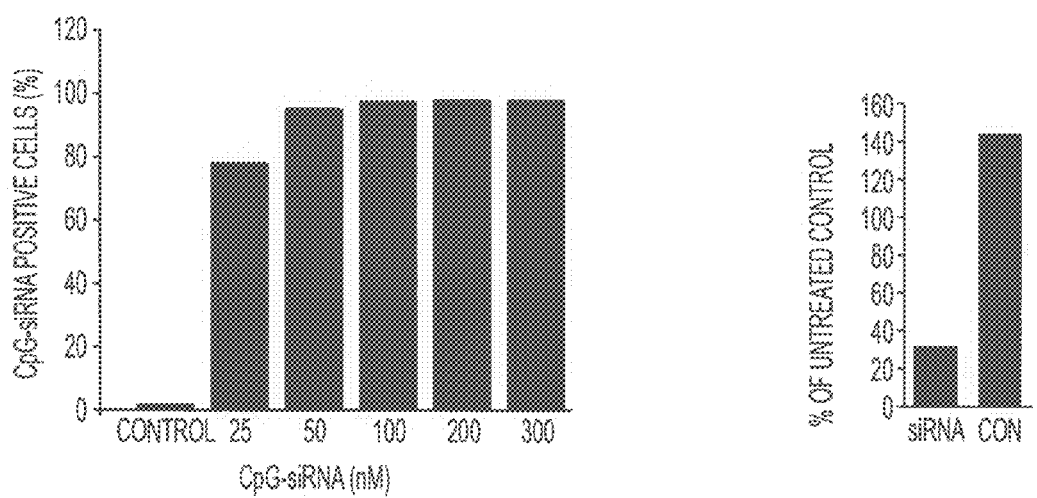
FIG. 5c
FIG. 5d

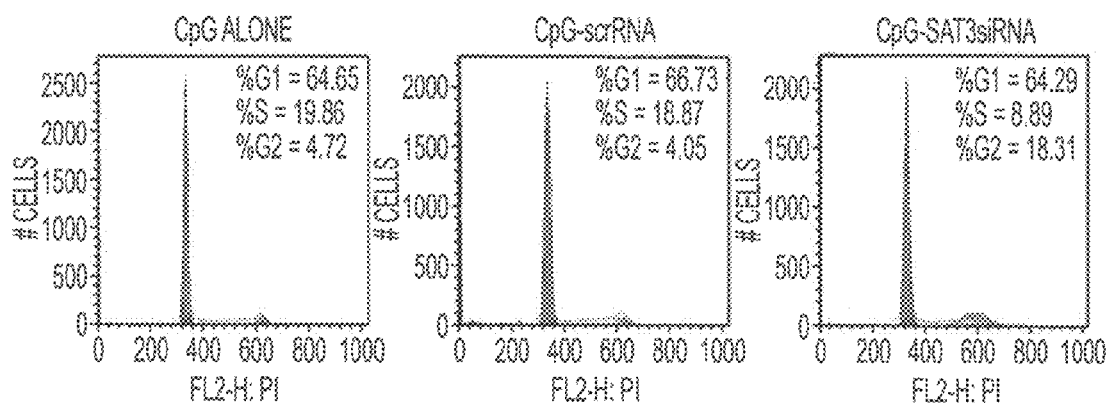
FIG. 5e
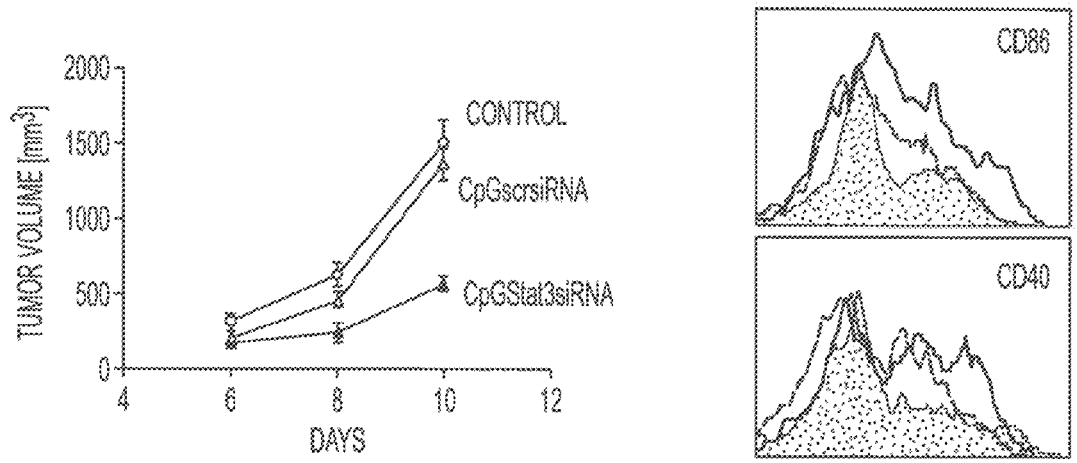
FIG. 6a
FIG. 6c
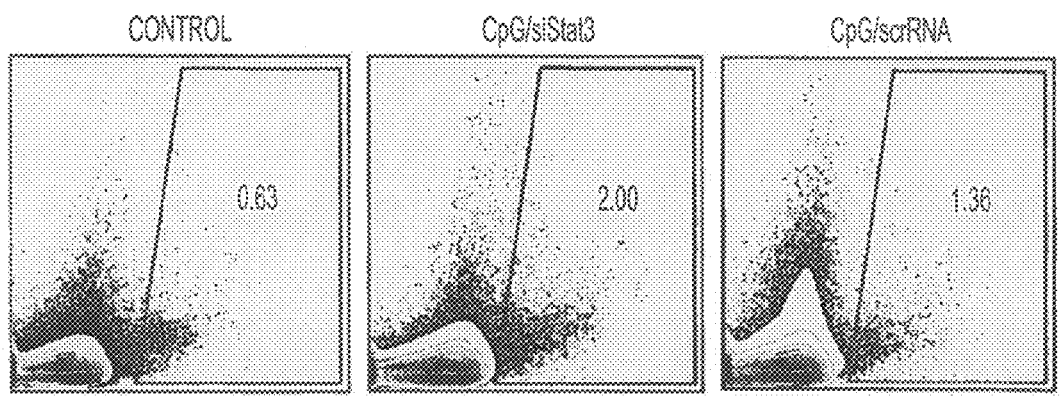
FIG. 6b

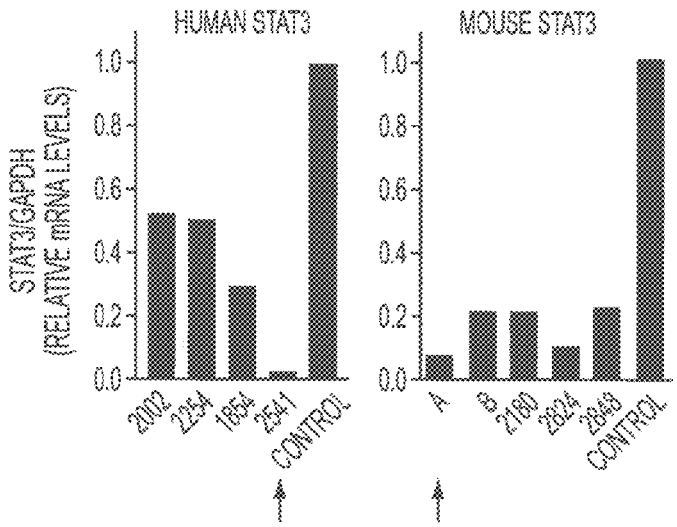

Optimal sequence for human STAT3 siRNA (#2541):
SS 5' rGrGrA rArGrC rUrGrC rArGrA rArArG rArUrA rCrGrA rCrUdG dA 3'
AS 5' rUrCrA rGrUrC rGrUrA rUrCrU rUrUrC rUrGrC rArGrC rUrUrC rCrGrU 3'

Optimal sequence for mouse Stat3 siRNA (A):
SS 5' rCrArG rGrGrU rGrUrC rArGrA rUrCrA rCrArU rGrGrG rCrUdA dA 3'
AS 5' rUrUrA rGrCrC rCrArU rGrUrG rArUrC rUrGrA rCrArC rCrCrU rGrArA 3'

FIG. 7

Mouse Stat3 siRNA (SS)
    5' CAGGGUGUCAGAUCACAUGGGCUAA 3'
CpG1668-mouse Stat3 siRNA(AS)
    5' TCCATGACGTTCCTGATGCT-linker-UUAGCCCAUGUGAUCUGACACCCUGAA 3'
GpC-mouse Stat3 siRNA (AS)
    5' TCCATGACGTTCCTGATGCT-linker-UUAGCCCAUGUGAUCUGACACCCUGAA 3'
Human STAT3 siRNA (SS)
    5' GGAABCUGCAGAAAGAUACGACUGA 3'
CpG(D19)-human STAT3 siRNA (AS)
    5' GGTGCATCGATGCAGGGGGG-linker-UCAGUCGUAUCUUUCUGCAGCUUCCGU 3'
Scrambled RNA (SS)
    5' UCCAAGUAGAUUCGACGGCGAAGUG 3'
CpG1668-scrambled RNA (AS)
    5' TCCATGACGTTCCTGATGCT-linker-CACUUCGCCGUCGAAUCUACUUGGAUU 3'

FIG. 8

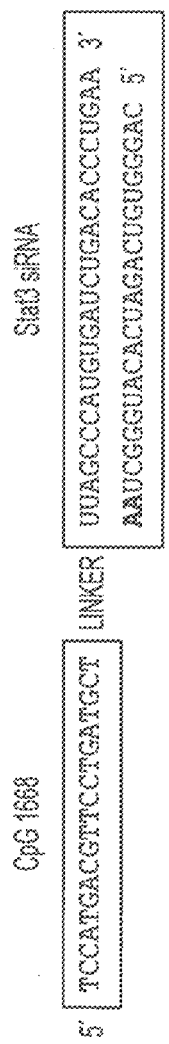
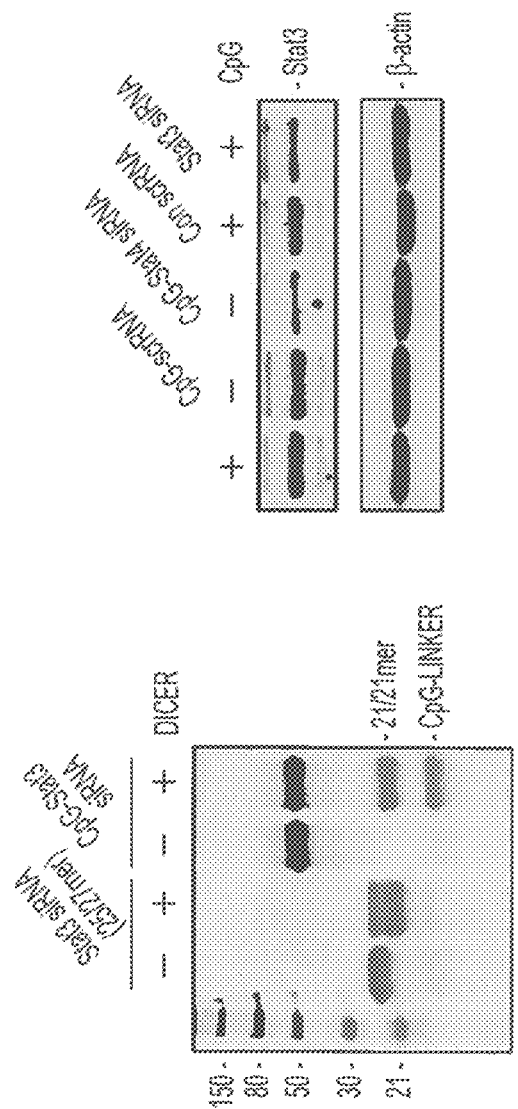
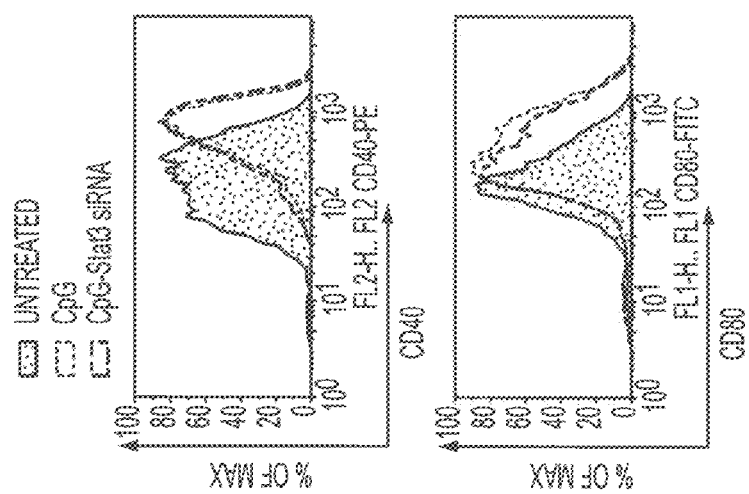
FIG. 11a
FIG. 11b
FIG. 11c
FIG. 11d

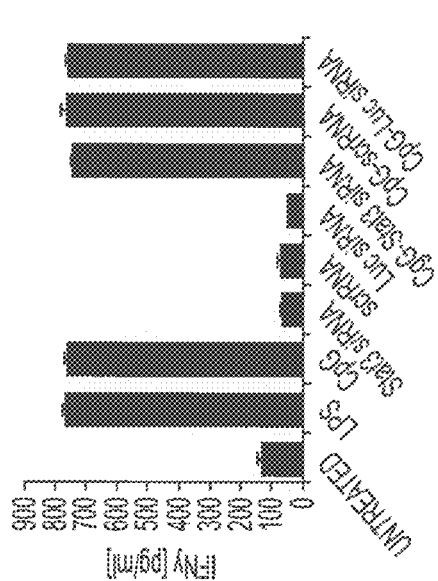
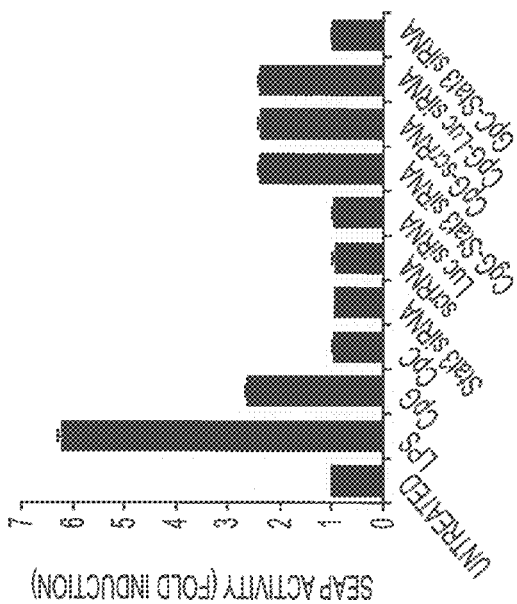
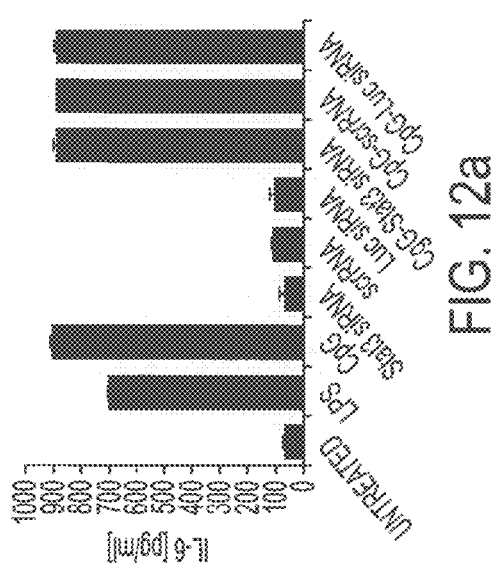
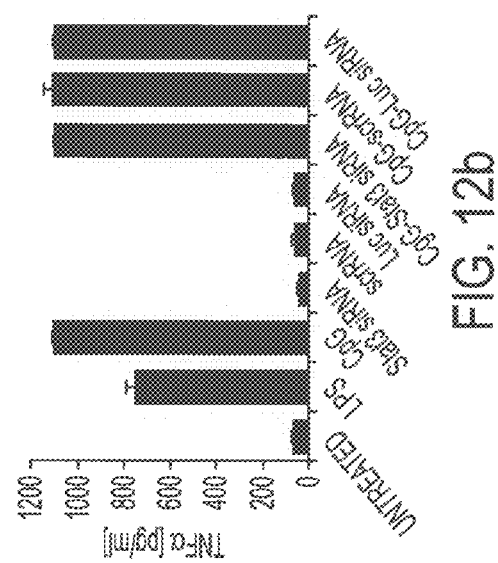
FIG. 12a
FIG. 12b
FIG. 12c
FIG. 12d

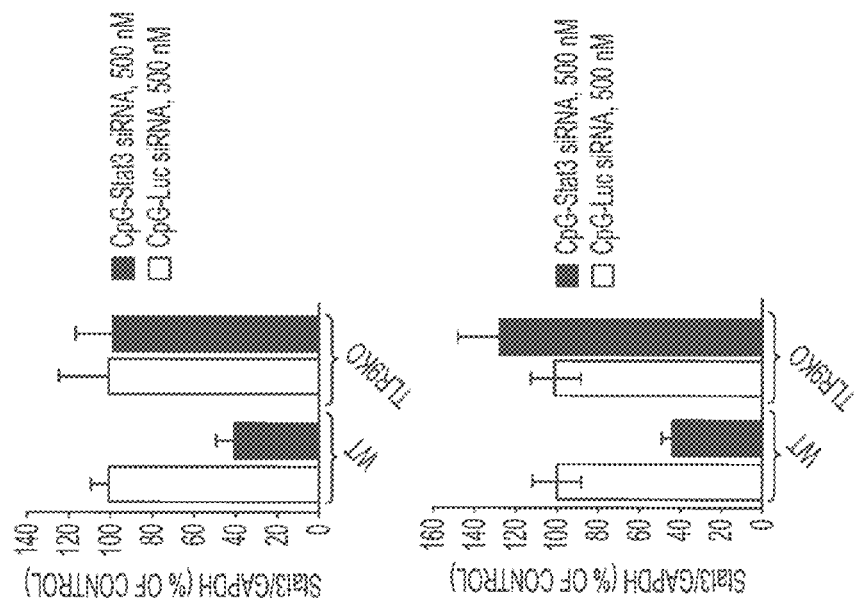
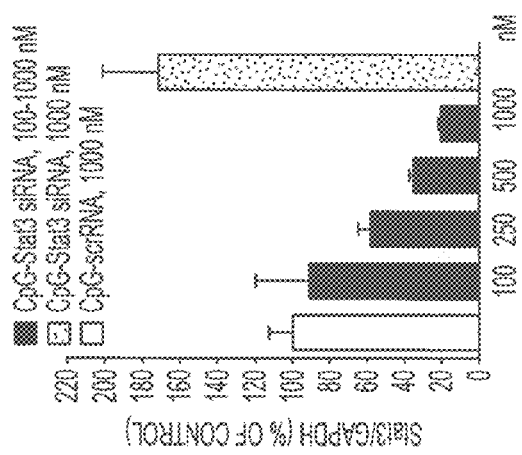
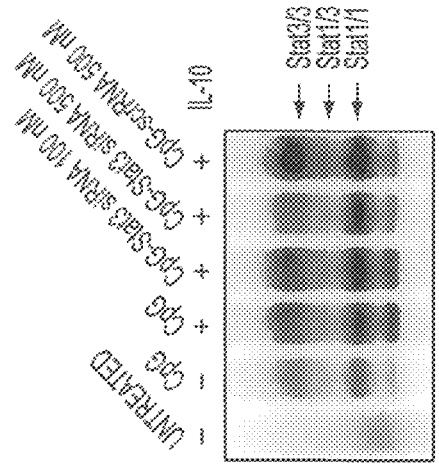

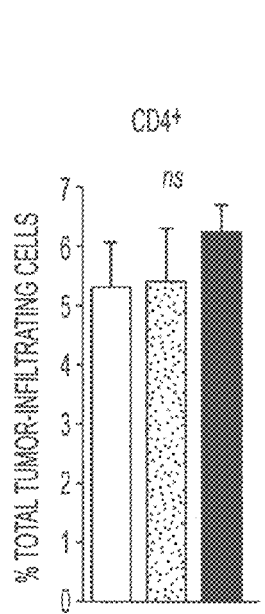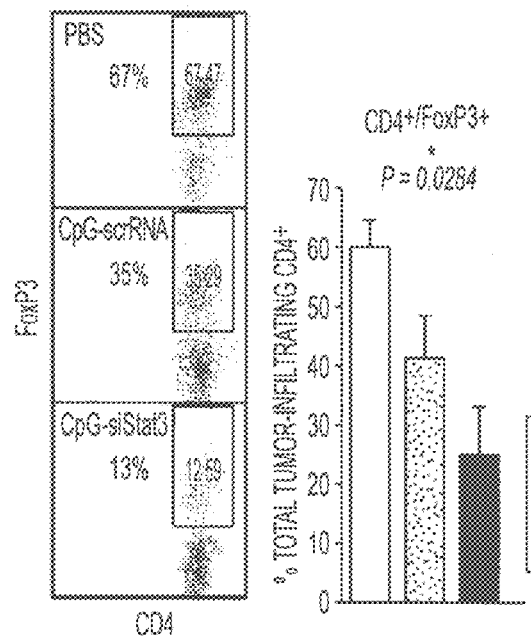
FIG. 28a    FIG. 28b
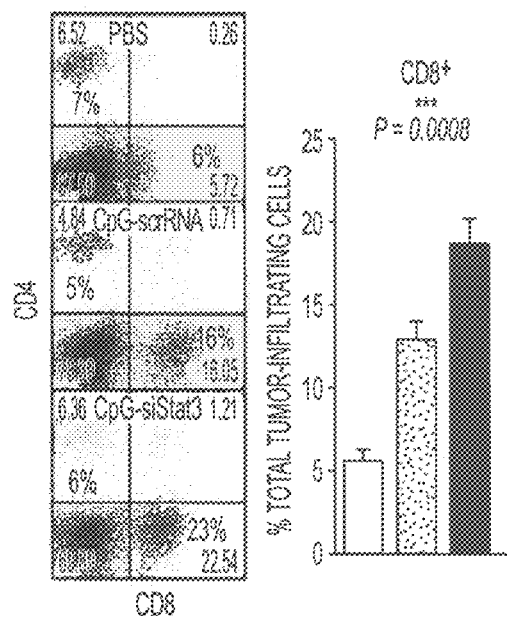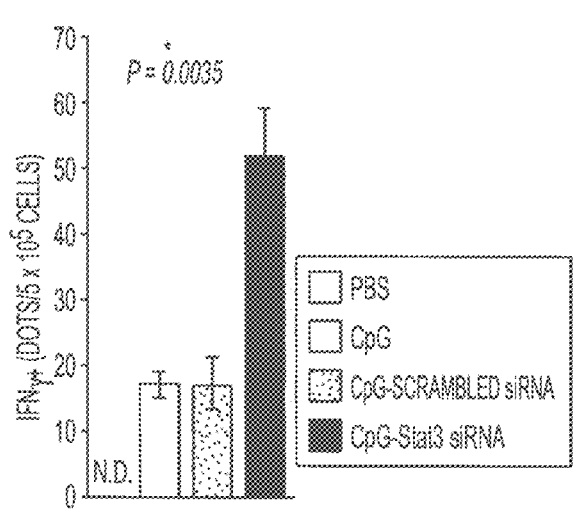
FIG. 28c    FIG. 28d

*Mouse Stat3 siRNA #2 (SS)*
5' GUGACACCAACGACCUGCAGCAA<u>TA</u> 3'
*CpG1668-mouse Stat3 siRNA #2 (AS)*
5' <u>TCCATGACGTTCCTGATGCT</u>-linker-UAUUGCUGCAGGUCGUUGGUGUCACAC 3'
*Mouse Stat3 siRNA #3 (SS)*
5' GUCUGAAACUCCUAACUUUGUGG<u>TT</u> 3'
*CpG1668-mouse Stat3 siRNA #3 (AS)*
5' <u>TCCATGACGTTCCTGATGCT</u>-linker-AACCACAAAGUUAGGAGUUUCAGACGA 3'
FIG. 29a
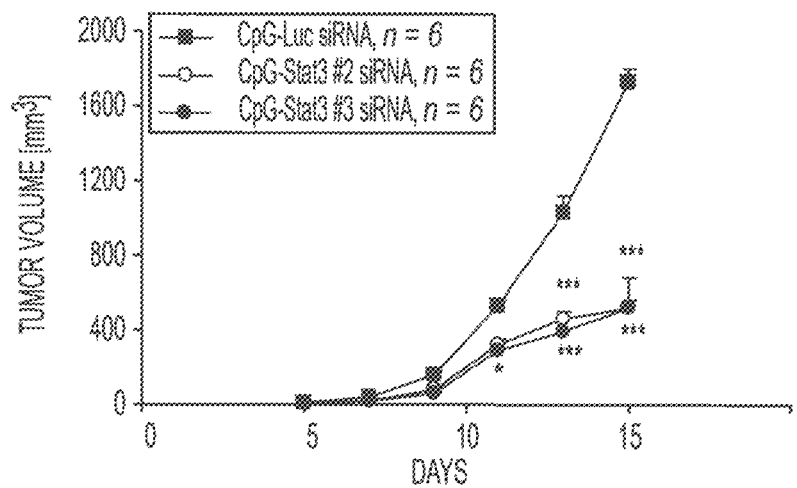
FIG. 29b
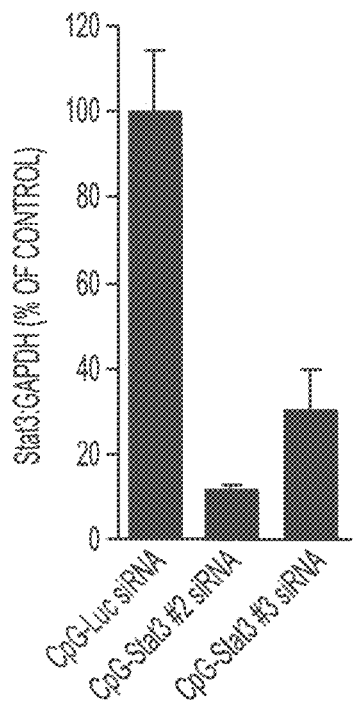
FIG. 29c

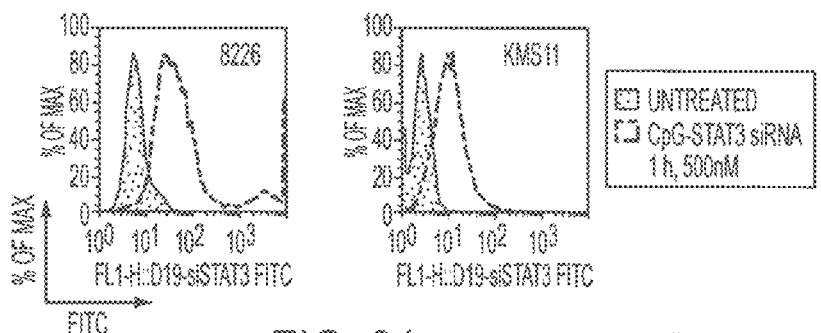
FIG. 31a
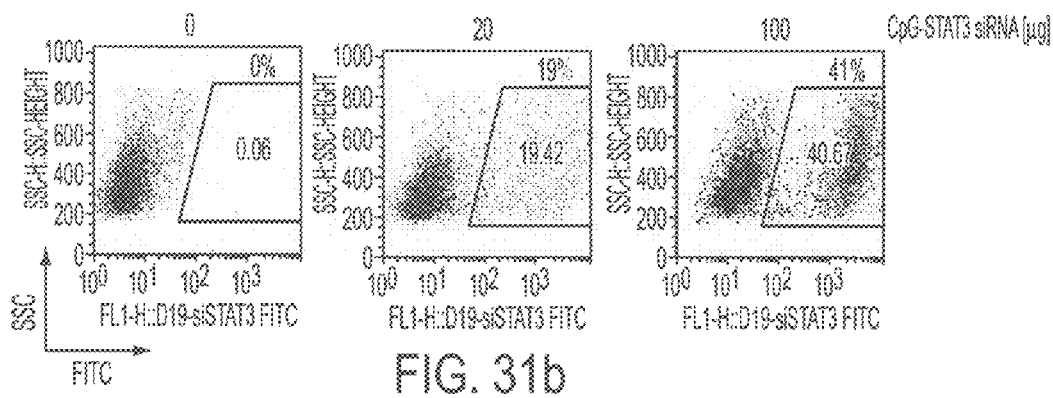
FIG. 31b
 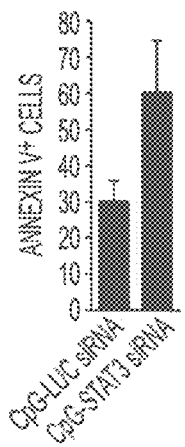 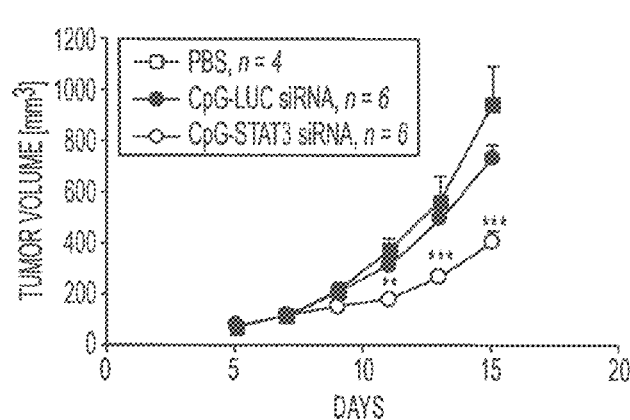
FIG. 31c  FIG. 31d  FIG. 31e

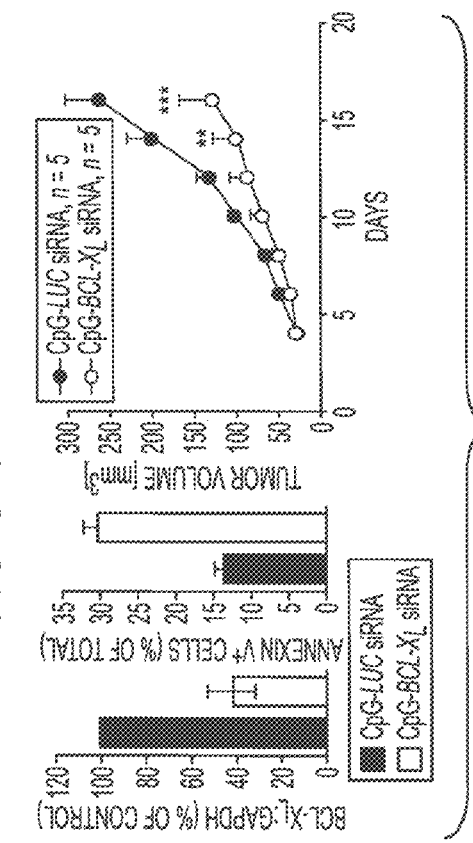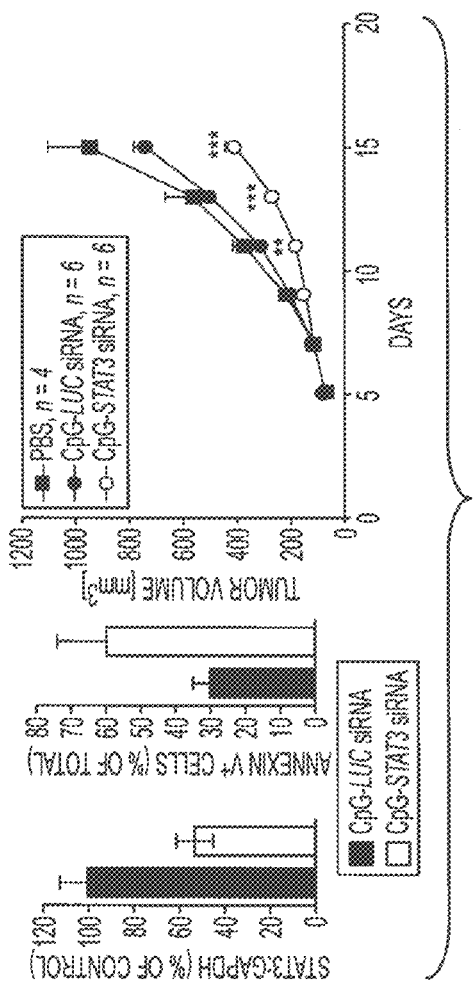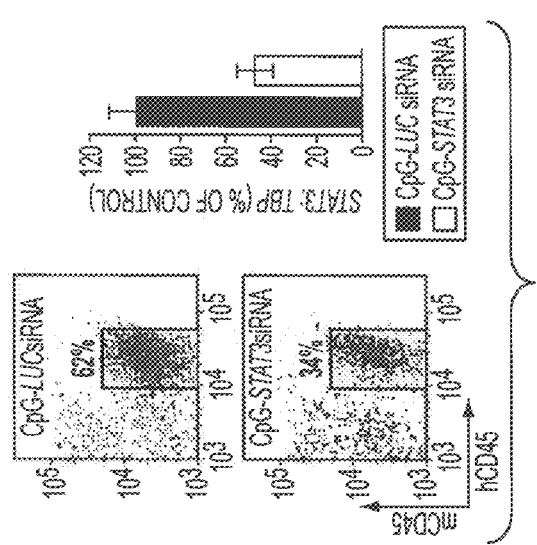
FIG. 32b
FIG. 32d
FIG. 32a
FIG. 32c

METHODS AND COMPOSITIONS FOR THE TREATMENT OF CANCER OR OTHER DISEASES

CROSS-REFERENCE TO RELATED APPLICATION

The present application is a division of U.S. patent application Ser. No. 13/229,146 filed 9 Sep. 2011, now U.S. Pat. No. 8,748,405, which in turn is a continuation-in-part of U.S. patent application Ser. No. 12/879,199 filed 10 Sep. 2010, now abandoned, which in turn is a continuation-in-part of U.S. patent application Ser. No. 11/966,423 filed 28 Dec. 2007, now abandoned. The present application is further related to and claims priority under 35 U.S.C. §119(e) to U.S. Provisional Patent Application Ser. No. 61/466,086 filed on 22 Mar. 2011. application Ser. No. 12/879,199 is further related to and claims priority under 35 U.S.C. §119(e) to U.S. Provisional Patent Application Ser. No. 61/241,764 filed on 11 Sep. 2009. application Ser. No. 11/966,423 is further related to and claims priority under 35 U.S.C. §119(e) to U.S. Provisional Patent Application Ser. No. 60/897,495 filed on 26 Jan. 2007. Each application is incorporated herein by reference.

STATEMENT OF FEDERALLY SPONSORED RESEARCH

The present invention was made in part with Government support under Grant Numbers R01-89693, R01-100878, R01CA115815, R01CA122976, R01CA115674 and P50CA107399 awarded by the National Institutes of Health/National Cancer Institute, Bethesda, Md. The Government has certain rights in this invention.

SEQUENCE SUBMISSION

The present application is being filed along with a Sequence Listing in electronic format. The Sequence Listing is entitled 1954568SequenceListing.txt, created on 8 Jan. 2014, and is 7 kb in size. The information in the electronic format of the Sequence Listing is part of the present application and is incorporated herein by reference in its entirety.

BACKGROUND OF THE INVENTION

The present invention relates to methods and compositions for the treatment of diseases, including cancer, infectious diseases and autoimmune diseases. The present invention also relates to methods and compositions for improving immune function. More particularly, the present invention relates to multifunctional molecules that are capable of being delivered to cells of interest for the treatment of diseases and for the improvement in immune function.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Signal Transducer and Activator of Transcription 3 (Stat3) is constitutively activated at high frequency (50 to 100%) in diverse cancers (Yu and Jove, 2004; Yu et al., 2007; Kortylewski et al., 2005a). Blocking Stat3 in tumor cells induces tumor cell apoptosis, inhibits tumor angiogenesis and abrogates metastasis (Yu and Jove, 2004; Yu et al., 2007; Xie et al., 2004; Xie et al., 2006), and activates antitumor immune responses (Wang et al., 2004; Kortylewski et al., 2005b). Our recent studies further demonstrate that Stat3 is constitutively activated in tumor-stromal myeloid cells, including $Gr1^+$ immature myeloid cells, DCs, macrophages, NK cell, neutrophils. Activated Stat3 inhibits expression of Th-1 type immune responses while promoting tumor accumulation of T regulatory cells and Th17 cells, compromising antitumor effects of immune effector cells, such as NK cells, neutrophils and $CD8^+$ T cells (Kortylewski et al., 2005b). Blocking Stat3 in the immune subsets leads to activation of antitumor immunity and immune-mediated tumor growth inhibition and tumor regression (Kortylewski et al., 2005b). Our preliminary data further demonstrate that Stat3 is constitutively activated in $CD4^+CD25^+/Foxp3^+$ T regulatory cells within the tumor stroma. A requirement of Stat3 for expression of Foxp3, TGFβ and IL-10—the hallmarks of T regulatory cells—in $CD4^+$ T cells has been demonstrated in both animal models and human T cells obtained from clinical trials (Yu et al., 2007). A recent study involving human melanoma cells has also confirmed a critical role of Stat3 in mediating tumor immune evasion/suppression (Sumimoto et al., 2006).

Stat3 is a point of convergence for numerous tyrosine kinase signaling pathways, which are the most frequently overactive oncogenic pathways in tumor cells of diverse origins (Yu and Jove, 2004). The reason Stat3 is also constitutively-activated in tumor stromal cells is because many of the Stat3 target genes encode secreted molecules whose cognate receptors signal through Stat3 (Yu et al., 2007). For example, Stat3-regulated products such as IL-10, IL-6 and VEGF have their receptors in diverse myeloid cells and T lymphocytes. VEGF and bFGF, both of which also require Stat3 for their expression, activates Stat3 in endothelial cells. Activated Stat3 promotes expression of a wide range of genes critical for tumor cell survival, proliferation, angiogenesis/metastasis and immune suppression. Activated Stat3 also inhibits expression multiple genes that are pro-apoptotic, anti-angiogenic and Th-1 type immunostimulatory, whose upregulation are critical for anti-cancer therapy (Yu and Jove, 2004; Yu et al., 2007; Kortylewski et al., 2005b).

RNA interference provides compelling opportunities to control gene expression in cells and siRNAs therefore represent a family of new drugs with broad potential for the treatment of diverse human diseases. Several recent studies have demonstrated the feasibility of in vivo siRNA delivery, leading to therapeutic effects in mouse models (Song et al., 2005; Hu-Lieskovan et al., 2005; McNamara et al., 2006; Kumar et al., 2007; Poeck et al., 2008) and also in non-human-primates (Li et al., 2005; Zimmermann et al., 2006). Nevertheless, efficient in vivo targeted delivery of siRNA into specific cell types, especially those of immune origin, which are important constituents of the tumor microenvironment and active players in promoting tumor progression, remains to be fully explored before the full potential of therapeutic RNA interference can be realized. One promising approach for targeted delivery of siRNA is the use of aptamers, which are oligonucleotide-based ligands that bind to specific receptors, such as those on tumor cells (McNamara et al., 2006). Recent studies further indicated the ability of specific aptamers to bind and modulate the functions of their cognate targets in T cells, leading to potent antitumor immune responses (McNamara et al., 2008). However, whether these aptamers can mediate siRNA delivery into T cells remains to be determined.

The immune system can serve as extrinsic tumor suppressor (Bui and Schreiber, 2007; Koebel et al., 2007; Shankaran et al., 2001). However, the microenvironment of established tumors is typically characterized by a paucity of tumor-specific CD8+ T cells together with an excess of suppressive regulatory T cells and myeloid-derived suppressor cells (MDSC) that promote tumor immune evasion (Kortylewski et al., 2005b; Yu et al., 2005; Curiel et al., 2004; Ghiringhelli et al., 2005; Melani et al., 2003). Myeloid cells and other immune cells in the tumor microenvironment also produce growth factors and angiogenic/metastatic factors critical for tumor progression (Kujawski et al., 2008). As noted above, Stat3 is an important oncogenic molecule. The orchestration of these processes in the tumor microenvironment is highly dependent on the oncogenic transcription factor, Stat3 (Yu et al., 1995; Bromberg et al., 1999; Yu and Jove, 2004; Darnell, 2002; Yu et al., 2007). In particular, we and others have recently demonstrated a critical role of Stat3 in mediating tumor immune evasion (Wang et al., 2004; Kortylewski et al. 2005b; Yu et al., 2007). Activated Stat3 in myeloid cells inhibits expression of a large number of immunostimulatory molecules related to Th1-type responses, while promoting production of several key immunosuppressive factors (Yu et al., 2007, Kortylewski and Yu, 2008; Kortylewski et al., 2009a) as well as angiogenic factors (Kujawski et al., 2008). In addition, by mediating signaling of certain cytokines and growth factors, notably IL-6, Stat3 activation in myeloid cells activates Stat3 in tumor cells, enhancing tumor cell proliferation and survival (Bollrath et al., 2009; Grivennikov et al., 2009; Lee et al., 2009; Wang et al., 2009).

It is desired to develop new molecules and methods for the treatment of cancer and other diseases, including new molecules and methods for treatment that involve pathways within cells that modulate the disease, such as the Stat3 pathway.

SUMMARY OF THE INVENTION

The present invention relates to methods and compositions for the treatment of diseases, including cancer, infectious diseases and autoimmune diseases. The present invention also relates to methods and compositions for improving immune function. The present invention relates to blocking Stat3, either through genetic knockout, Stat3 small-molecule inhibitor, or Stat3 siRNA, which drastically improves the immune responses induced by CpG.

The present invention relates to multifunctional molecules that are capable of being delivered to cells of interest. The multifunctional molecules incorporate an activation element together with a therapeutic element, e.g., a Stat3 blocking element. The multifunctional molecules are capable of being delivered to specific cells of interest including, but not limited to, dendritic cells. These molecules are capable of treating diseases, including cancer, infectious diseases and autoimmune diseases. More particularly, the present invention is related to chimeric molecules consisting of an active oligonucleotide, such as Toll-like receptor (TLR) ligands, and an active agent, such as double stranded RNA, such as siRNA or activating RNA. Such chimeric molecules are taken up and internalized by immune cells and malignant cells, allowing actions of both the TLR ligand and the active agent. More specifically, the present invention relates to specific chimeric molecules that are useful for the treatment of diseases.

In one aspect, the present invention provides a novel molecule for the delivery of an active agent into cells for the treatment of diseases including, but not limited to cancer, infectious diseases and autoimmune diseases. The novel molecules comprises one or more of a first moiety that directs cell or tissue specific delivery of the novel molecule linked to one or more of a second moiety that is an active agent useful for treating cancer or other diseases. The moieties can be linked together directly or they can be linked together indirectly through a linker. In one embodiment, the novel molecule comprises two moieties as one molecule that is multifunctional. For example, a TLR ligand and an siRNA are made into one molecule for delivery, immune stimulation and blocking immunosuppressive elements, such as Stat3, and/or oncogenic effects, such as caused by Stat3. In another embodiment, the novel molecule comprises multifunctional moieties attached to a linker, such that it can contain a multitude of moieties. In another embodiment, the linker is bifunctional producing a molecule of the structure A-X-B, where X is a linker, one of A and B is a moiety that is capable of delivering the molecule to cells of interest and the other one of A and B is an active agent useful for treating the cancer or other disease. A and/or B may also be subject to further linking. In another embodiment, the linker is multifunctional, producing a molecule having more than two moieties. In one embodiment, using as an example a quadrifunctional form, such a molecule can have the structure

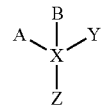

where X is a linker with four binding sites, one or more of A, B, Y and Z is a moiety that is capable of delivering the molecule to cells of interest and the others are an active agent useful for treating the cancer or other disease. In one embodiment, the active agent is a double stranded RNA molecule that either downregulates gene expression, such as an siRNA molecule, or activates gene expression, such as an activating RNA molecule. In another embodiment, the active agent is a small molecule drug or peptide. In one embodiment, the delivery moiety is a ligand for a toll-like receptor (such as oligonucleotides described herein). In another embodiment, the delivery moiety is another cell-specific ligand (including, but not limited to, aptamers).

The binding sites on a linker may be specific for each type of moiety to be linked, for example a linker with a structure that has one region capable of likening to an oligonucleotide and another region capable of binding to a peptide. Other variations of structure can be proposed by utilizing structures and linkers that promote branching, circularization or linearization of the molecules, including combinations thereof. Any element of a multimeric molecule, including the linker, may also have additional functional properties such as being a substrate for chemical reactions, including enzyme catalyzed reactions, lability in environmental conditions such as oxygen tension, pH, ionic conditions. In addition, any element of a multimeric molecule, including linkers may also include labels to promote detection—using active or passive detection of electromagnetic emissions (e.g. optical, ultraviolet, infra-red), radioactivity, magnetic resonance or ability to be cleaved or catalyse a reaction. Many means are available to promote this including use of fluorochromes, quantum dots, dyes, inherent physical chemical properties structures such as spectral absorbance or emission characteristics magnetic resonance enhancers, and radioisotopes.

In a second aspect, the present invention provides a method for the treatment of diseases (including, but not limited to, cancer, infectious diseases, autoimmune diseases, diseases due to excessive angiogenesis and diseases that can benefit from increased angiogenesis) which comprises using the novel molecules of the present invention. The molecules of the present invention are administered to patients in need of treatment using conventional pharmaceutical practices.

In a third aspect, the present invention provides active agents that are capable of acting in the Stat3 pathway which, when taken up by the cells of interest, results in the treatment of diseases including, but not limited to, cancer, infectious diseases and autoimmune diseases.

BRIEF DESCRIPTION OF THE FIGURES

FIGS. 1a-1i show that ablating Stat3 drastically improves TLR ligand induced antiumor effects which is caused by immune activation. Mice with Stat3$^{+/+}$ and Stat3$^{-/-}$ hematopoietic cells were challenged with B16 melanoma tumors (s.c.) and treated with a single peritumoral injection of 5 μg CpG ODNs. FIG. 1a: Changes in tumor volume within 3 days post-CpG treatment. FIG. 1b: Results from two independent experiments with either smaller (10 mm$^3$) or larger (70 mm$^3$) average tumor sizes at the time of CpG ODN injection (n=4). FIGS. 1c and 1d: Blocking Stat3 signaling in immune cells leads to CpG-induced tumor eradication and improved survival, which is in part mediated through CD4 and CD8 T cells. Mice with B16 tumors were treated with a single peritumoral injection of CpG ODNs. Depleting antibodies against CD4$^+$ and CD8$^+$ T cells were given to the indicated groups of mice. Rat IgG antibody was used as a control. Shown are the results representative of three independent experiments. FIG. 1e: Stat3 ablation enhances TLR9-mediated DC maturation within tumor-draining lymph nodes in vivo. The phenotypic analysis of CD11c$^+$ DCs residing in tumor-draining lymph nodes of Stat3$^{+/+}$ and Stat3$^{-/-}$ mice 48 h post-CpG injection. The maturation of CD11c$^+$ DCs is increased by Stat3 ablation as shown by a greater percentage of double-positive MHC class II$^{hi}$ and CD86$^{hi}$ DCs (upper panels), as well as higher expression of costimulatory molecules CD80 and CD40 on DCs (lower panels). Shown are representative results of FACS analysis from one of three independent experiments with 3-4 mice per group. FIG. 1f: Expression of proinflammatory mediators is strongly upregulated in DCs isolated form CpG-treated tumors. Upper panel—both p35 and p40 subunits of IL-12, RANTES and IL-6 is upregulated in Stat3$^{-/-}$ DCs in vivo 18 hrs after CpG treatment. Shown are the results of real-time PCR analysis of gene expression in CD11c$^+$ cells isolated from tumor-draining lymph nodes. Lower panel—enhanced secretion of proinflammatory cytokines and chemokines by tumor-infiltrating Stat3$^{-/-}$ DCs within 48 h post-CpG injection. Cytokine and chemokine expression was analyzed using antibody arrays in supernatants collected from cultured tumor-infiltrating DCs isolated from Stat3$^{+/+}$ and Stat3$^{-/-}$ mice without or after CpG treatment. FIG. 1g: CD8$^+$ lymphocyte subsets in tumor-draining lymph nodes of Stat3$^{-/-}$ mice show increased activation 24 h after CpG ODN injection. The expression of the early lymphocyte activation marker CD69 was analyzed by flow cytometry on CD8$^+$ T cells. Results shown represent one of three independent experiments using lymph node cell suspensions from 3-4 mice per group. FIG. 1h: Stat3$^{-/-}$ mice mount stronger response against an endogenous B16 tumor-antigen than their Stat3$^{+/+}$ counterparts, following treatment with CpG ODN. IFN-γ production in T cells derived from tumor-draining lymph node was assessed by ELISPOT assay. Data shown are mean numbers of p15E-specific IFNγ-producing spots from one of two separate experiments with cells pooled from four separate animals per group analyzed. FIG. 1i: FIG. 1i: Blocking Stat3 using a small-molecule Stat3 inhibitor drastically improves CpG antitumor effects. Top panel: growth of B16 tumor is significantly inhibited when peritumoral CpG ODNs treatment is combined with systemic inhibition of Stat3 activity by a Stat3 inhibitor, CPA7. Mice with established tumors (average diameter 5-8 mm) were treated with CPA7, followed by peritumoral CpG injection a day later. The treatment was repeated twice weekly. Bottom panel: local CpG treatment promotes concomitant antitumor immunity when Stat3 activity is systemically suppressed. Mice surviving after primary tumor challenge were injected with the same tumor cells as the primary tumor challenges into the opposite flanks. Shown are the results representative of three independent experiments; n=10 for each experiment.

FIG. 2a: Upper panel: Sequence of the CpG1668-Stat3 siRNA construct: deoxynucleotides (left portion of molecule) in CpG1668 sequence (SEQ ID NO:1) were phosphothioated and connected through linker (7 units of C3 spacer) to the antisense strand of a Stat3 siRNA (right portion of molecule; antisense strand: SEQ ID NO:2; sense strand: SEQ ID NO:3)). Lower panel: CpG-Stat3 siRNA is processed to active 21-mer siRNA by recombinant Dicer in vitro. Various double stranded siRNAs were incubated with 1 U of recombinant Dicer for 1 h at 37° C. and then visualized on polyacrylamide gel through SYBRGold staining FIG. 2b: Left panels: splenocytes were incubated for 24 h with two concentrations of CpG-linked mouse Stat3 siRNA (CpG-Stat3 siRNA, three upper panels) or unconjugated mouse Stat3 siRNA labeled with fluorescein (bottom panel). Percentage of fluorescein-positive DCs, macrophages, granulocytes, B cells and T cells was assessed by FACS analysis. Splenic CD11c$^+$ DCs express high levels of TLR9. Intracellular staining of TLR9 as shown in fixed splenic DCs by flow cytometry. FIG. 2c: CpG-Stat3 siRNA-FITC is quickly internalized by dendritic cells in the absence of transfection reagents. The uptake by DC2.4 cells is analyzed by flow cytometry (upper panel) and confocal microscopy (lower panels) after incubation times as indicated. FIG. 2d: Internalized CpG-Stat3 siRNA colocalizes with TLR9 (two upper rows) and transiently interacts with Dicer (two lower rows) as shown by confocal microscopy. DC2.4 cells were incubated with 500 pmol/ml of CpG-Stat3siRNA for times as indicated. Shown are confocal microscopy images; green: CpG-Stat3 siRNA-FITC, red—TLR9 or Dicer, blue—nuclear staining with Hoechst. FIG. 2e: Treatment with CpG-Stat3siRNA leads to silencing of Stat3 expression in DC2.4 cells. Cells were treated for 24 hrs with 1 μM CpG-Stat3 siRNA or CpG-scrambled RNA. Shown are the results of real-time PCR for Stat3, normalized to GAPDH levels. The level of Stat3 expression in CpG-scrambled RNA sample is set as 100%. FIG. 2f: Stat3 DNA-binding is reduced following 48 h of incubation with CpG-Stat3 siRNA but not with CpG-scrambled RNA.

FIGS. 3a-3h show that treatment with CpG-Stat3 siRNA leads to antitumor effects in vivo. FIG. 3a: In vivo uptake of intratumorally injected CpG-Stat3 siRNA by myeloid cells. Upper panel: immunofluorescent imaging on frozen tumor and lymph node tissue sections 6 h after CpG-construct injection. Green: FITC-labeled CpG-Stat3 siRNA, red: staining with anti-CD11b-specific antibody, blue: nuclear staining with Hoechst. Lower panel: intravital two-photon microscopy on tumor-draining lymph node within 1 h after intratumoral injection of FITC-labeled CpG-Stat3 siRNA (green), blood vessels: red, nuclei: blue; top right panel: close-up of the lymph node tissue to visualize increased number of FITC-positive cells entering the lymph node, bottom right panel: intracellular distribution of FITC-labeled CpG-Stat3 siRNA. FIG. 3b: Local treatment with CpG-Stat3 siRNA reduces Stat3 expression in DCs within tumor draining lymph nodes.

Total RNA was isolated from tumor-draining lymph node DCs and analyzed by real-time PCR. FIG. 3c: B16 tumor growth is inhibited by local treatment with CpG-Stat3 siRNA. Mice with subcutaneously growing tumors were treated by repeated peritumoral injections of 14 μg CpG-Stat3 siRNA, GpC-Stat3 siRNA, CpG-scrambled RNA or combination of equimolar amounts of uncoupled CpG and Stat3 siRNA every second day, starting six days after challenge with $1 \times 10^5$ B16 cells. FIG. 3d: Right panel: Stat3 expression is reduced by systemic CpG-Stat3 siRNA treatment in DCs within tumor draining cervical lymph nodes. Shown are results of real-time PCR analysis. FIG. 3e: Systemic treatment with CpG-Stat3 siRNA reduces the number of B16 tumor metastasis. Mice were injected i. v. with $1 \times 10^5$ B16 cells and treated with 14 μg CpG-Stat3 siRNA or CpG-scrambled RNA injections every second day starting from two days post-challenge. Lung colonies were enumerated 15 days later when mice become moribund. Significant differences between mean numbers±SEM, of CpG-Stat3 siRNA or CpG-scrambled RNA-treated mice are indicated (right panel). Representative picture of lung excised from mice inoculated and treated as described above (left panel). FIGS. 3f and 3g: Stat3 inhibition promotes DC maturation (FIG. 3f) and increases ratio of effector to regulatory T cells within tumor tissue (FIG. 3g). Single cell suspensions prepared from tumor-draining lymph nodes (FIG. 3f) or tumors (FIG. 3g) treated with peritumoral injections of CpG-Stat3 siRNA or CpG-scrambled RNA as described in 3a, were analyzed by flow cytometry. FIG. 3h: Local treatments with CpG-Stat3 siRNA lead to increased tumor infiltration by $CD8^+$ T cells (left), and generate tumor antigen-specific CD8+T cell immune responses as measured by TRP-2 specific IFN-γ ELISPOT (right).

FIG. 4d: STAT3 silencing in monocyte-derived DCs. Enriched $CD14^+$ monocytes were cultured for 6 days in the presence of GM-CSF and IL-4 with the addition of fluorescein-labeled CpG(D19)-STAT3 siRNA or CpG-scrambled RNA control. The expression of STAT3 was estimated by real-time PCR on total RNA isolated on day 6.

FIGS. 5a-5e show that CpG-STAT3 siRNA mediates siRNA delivery into human and mouse tumor cells of hematopoietic origin. FIG. 5a: Dose-dependent uptake of FITC-labeled CpG-STAT3 siRNA by human L540 Hodgkin's lymphoma cells after overnight incubation. FIG. 5b: CpGsiRNA internalization by human different types of lymphoma cells. Cells of each type were incubated overnight with 500 nM FITC-labeled CpG-STAT3 siRNA and analyzed with flow cytometry. FIG. 5c: MCP11 cells internalize FITC-labeled CpG-Stat3 siRNA in a dose-dependent manner, as shown by flow cytometry after 24 h incubation. FIG. 5d: Stat3 silencing in MPC 11 cells treated with 100 nM CpG-Stat3 siRNA for 24 h, as measured by real-time PCR. Con, control scrambled siRNA, siRNA=mouse Stat3siRNA. FIG. 5e: MCP11 cells accumulate in the $G_2M$ phase of cell cycle after 48 h incubation with CpG-Stat3 siRNA as measured by flow cytometry after propidium iodide staining.

FIGS. 6a-6c show that targeting Stat3 by CpG-Stat3 siRNA leads to antitumor effects against MPC11 multiple myeloma. FIG. 6a: In vivo treatment with CpG-Stat3 siRNA results in immune activation and tumor growth inhibition. Mice bearing large MCP11 tumors (10-13 mm in diameter) were injected intratumorally with 0.78 nmole of CpG-Stat3siRNA or CpG-scrRNA, followed by two more times every second day. FIG. 6b: Increased percentage of DCs in tumor-draining lymph nodes after CpG-Stat3siRNA treatment. FIG. 6c: CD40 and CD86 expression on activated DCs in tumor-draining lymph nodes as measured by flow cytometry in CpG-siStat3 (red) or CpG-scrRNA (blue) injected mice comparing to untreated controls.

FIG. 7 shows selection of the most effective human and mouse STAT3 siRNA sequences. More than 50 double-stranded oligoribonucleotides (27mer, Dicer substrate) with potential STAT3 siRNA sequences were tested in human A2058 or mouse B16 melanoma cells. STAT3 silencing was assessed by quantitative real-time PCR, 24 h after transfection, and normalized to GAPDH expression. Control=scrambled siRNA, arrows indicate the most potent STAT3 siRNAs. The sequences of the optimal Stat3 siRNAs are shown. Human sense strand is SEQ ID NO:4; human antisense strand is SEQ ID NO:5; mouse sense strand is SEQ ID NO:3; mouse antisense strand is SEQ ID NO:2.

FIG. 8 shows TLR ligand-linker-Stat3siRNA sequences. Mouse Stat3 siRNA (SS): SEQ ID NO:3; CpG1668:SEQ ID NO:1; mouse Stat3 siRNA (AS): SEQ ID NO:2; GpC: SEQ ID NO:6; human Stat3 siRNA (SS): SEQ ID NO:4; CpG (D19): SEQ ID NO:7; human Stat3 siRNA (AS): SEQ ID NO:3; scrambled RNA (SS): SEQ ID NO:8; scrambled RNA (AS): SEQ ID NO:9).

FIGS. 11a-11d show the structure and function of the CpG-Stat3 siRNA conjugate. FIG. 11a: Sequence of the CpG-linked mouse Stat3 siRNA conjugate (CpG1668-Stat3 siRNA): CpG1668 sequence (deoxyribonucleotides; SEQ ID NO:1) were phosphothioated and connected through a carbon linker (6 of C3 units) to the antisense strand of Stat3 siRNA (ribonucleotides in the upper strand (SEQ ID NO:2); ribonucleotides in the lower strand except AA on the 3' end which are deoxyribonucleotides (SEQ ID NO:3). FIG. 11b: CpG-siRNA has similar immunostimulatory activity compared to uncoupled CpG ODN, as indicated by increased expression of costimulatory molecules, CD40 and CD80, on primary splenic DCs after 24 h incubation with or without ODNs; splenocytes were pooled from 2-3 mice and the experiment was done twice with similar results. FIG. 11c: Linked CpG-Stat3 siRNA is processed to active 21mer siRNA by recombinant Dicer in vitro. Comparable processing of conjugated CpG-Stat3 siRNA molecules and uncoupled Stat3 siRNA visualized on polyacrylamide gel through SYBRGold staining; position of the 21/21mer and the remaining part of the molecule (CpG plus carbon linker) are indicated. FIG. 11d: Stat3 siRNA linked to CpG ODN retains the ability to mediate RNA interference. B16 cells were transfected using lipofectamine reagent with CpG-linked dsRNAs or unconjugated dsRNAs in the presence of 15 nM CpG ODN as indicated. Stat3 gene silencing effects were evaluated by western blot analysis.

FIGS. 12a-12d show the relative immunostimulatory properties of various oligonucleotide sequences used in the study. FIGS. 12a-12c: Freshly isolated splenocytes (pooled from three C57BL/6 mice) were cultured for 24 h in the presence of LPS (0.5 μg/ml) or various oligonucleotides (500 nM of each) as indicated. The secretion of proinflammatory mediators including IL-6 (FIG. 12a), TNFα (FIG. 12b) and IFNγ (FIG. 12c) into culture media was assessed using ELISA. FIG. 12d: Immunostimulatory effects of various TLR agonists as measured using SEAP reporter gene assay. RAW-Blue™ cells (InvivoGen) were incubated for 24 h with LPS (5 μg/ml) or 500 nM of various oligonucleotides as indicated. The level of immune activation was assessed based on NF-κB/AP1-dependent induction of SEAP expression measured calorimetrically. Shown are representative results of two independent experiments analyzed in triplicates±SEM. This figure shows that linking siRNA to CpG does not create non-specific immune response.

FIGS. 13a-13f show CpG-Stat3 siRNA uptake and gene silencing in vitro. FIG. 13a: Targeted delivery: splenocytes derived form 2-3 mice were incubated for 3 h with various concentrations of CpG-Stat3 siRNA (top two columns) or for 24 h with unconjugated Stat3 siRNA labeled with fluorescein (bottom right panel) in the absence of any transfection reagents. Percentage of fluorescein-positive $CD11c^+B220^-$ non-plasmacytoid (mDCs) and $CD11c^+B220^+$ plasmacytoid (pDCs) DCs, $F4/80^+Gr1^-$ macrophages (MACs), $B220^+CD11c^-$ B cells, $Gr1^+F4/80^-$ granulocytes and $CD3^+$ T cells was assessed by FACS analysis (see also Table 1). Splenic $CD11c^+$ DCs express high levels of TLR9. Intracellular staining of TLR9 as shown in fixed splenic DCs by flow cytometry (bottom right panel). Similar results were obtained in two independent experiments using splenocytes pooled from 3 mice. FIG. 13b: Kinetics of CpG-siRNA internalization: CpG-Stat3 siRNA-FITC is quickly internalized by dendritic cells in the absence of transfection reagents. The uptake by DC2.4 cells is analyzed by flow cytometry (top row) and confocal microscopy (two lower rows) after incubation with CpG-Stat3 siRNA-FITC at the concentration of 500 nM for indicated times (two upper rows) or after 1 h incubation concentrations as indicated (bottom row); shown are results representative for 3 independent experiments. FIG. 13c: Internalized CpG-Stat3 siRNA colocalizes with TLR9 (two upper rows) and transiently interacts with Dicer (two lower rows) as shown by confocal microscopy. DC2.4 cells were incubated with 500 nM of CpG-Stat3 siRNA for indicated times. Shown are confocal microscopy images; green—CpG-Stat3 siRNA-FITC, red—immunofluorescent detection of endogenous TLR9 or Dicer, blue—nuclear staining with DAPI. All confocal imaging studies were performed at least thrice with similar results and the images acquired were characteristic for the majority of analyzed cells (FIG. 16). FIG. 13d: Dose-dependent gene silencing effects of CpG-Stat3 siRNA, comparing to GpC-Stat3 siRNA at the highest dose, as determined by quantitative real-time PCR in DC2.4 cells. Shown are the results of real-time PCR for Stat3, normalized to GAPDH expression levels. The level of Stat3 expression in CpG-scrambled RNA sample is set as 100%. Shown are means±SEM from three independent experiments analyzed in duplicates. FIG. 13e: Stat3 silencing is impaired in TLR9-deficient primary myeloid cells (top panel) and dendritic cells (bottom panel). Shown are results of two independent experiments, analyzed in triplicates by real-time PCR; means±SEM. FIG. 13f: Stat3 DNA-binding is reduced following 48 h incubation of DC2.4 cells with CpG-Stat3 siRNA, relative to CpG-scrambled RNA. Shown are results of electrophoretic mobility gel-shift assay using radiolabeled probe specifically bound by Stat3 and Stat1 in one of three independent experiments. Positions of Stat dimers are indicated.

FIG. 18a: A20 cells were cultured in the presence of the chimeric constructs for 24 h at indicated concentrations. FIG. 18b: CpG-Luc siRNA silences gene expression as shown by reduction in luciferase activity. CpG-Luc siRNA and CpG-scrambled RNA were added to Luc-A20 cells (100 nM). Shown are averages±SEM, n=5.

FIG. 20a: In vivo uptake of intratumorally injected CpG-Stat3 siRNA by myeloid cells. Shown is immunofluorescent staining of frozen tumor tissue section 6 h after injection of CpG-siRNA conjugate. Green: FITC-labeled CpG-Stat3 siRNA; red: myeloid cells stained with anti-CD11b antibodies: blue: nuclear staining with Hoechst. FIG. 20b: Left panel—intravital two-photon microscopy on tumor-draining lymph node at 1 h after intratumoral injection of FITC-labeled CpG-Stat3 siRNA (green); blood vessels stained with dextran-rhodamine (red); Hoechst-stained nuclei (blue). Top right panel: close-up of the lymph node tissue to visualize increased number of FITC-positive cells entering the lymph node; bottom right panel: intracellular distribution of FITC-labeled CpG-Stat3 siRNA. Results representative for two independent experiments using 2 mice per experiment are shown. FIGS. 20c and 20d: Repeated local peritumoral treatment with CpG-Stat3 siRNA significantly reduces Stat3 mRNA and protein in immune cells within tumor draining lymph nodes. Total RNA and protein were isolated from CD11c$^+$ DCs, CD19$^+$ B cells and CD11b$^+$c$^-$ myeloid cells accumulated in tumor-draining inguinal lymph nodes using cells pooled from 4-9 mice. FIG. 20c: Shown are combined results of quantitative real-time PCR analysis from 3-4 independent experiments±SEM comparing Stat3 expression levels in CpG-Stat3 siRNA-treated mice in relation to control CpG-Luc siRNA set as 100%. FIG. 20d: Stat3 activation and protein levels are reduced by CpG-Stat3 siRNA but not by control CpG-Luc siRNA conjugates. Representative results of Western blot analysis for tyrosine-phosphorylated or total Stat3 and β-actin from one of two independent experiments are shown. FIG. 20e: Two weeks after B16 tumor challenge, luciferase-overexpressing mice were injected peritumorally with CpG-Luc siRNA or CpG-scrambled RNA every day for a total of three injections. The level of luciferase activity was assessed in CD11b$^+$ and CD4$^+$ cells isolated from tumor-draining lymph nodes; shown are representative results from one of 3 independent experiments using 3 mice/group.

FIG. 23a: Local treatment using CpG-Stat3 siRNA leads to Stat3 silencing in tumor-draining lymph nodes. Shown are the results of real-time PCR for Stat3, normalized to GAPDH levels. The level of Stat3 expression in control PBS-treated sample is set as 100%. FIG. 23b: Levels of Stat3 protein in total tumor-draining lymph node cells are reduced by CpG-Stat3 siRNA but not control conjugates, CpG-scrambled RNA and CpG-Luc siRNA. Representative results of Western blot analysis from one of two independent experiments are shown.

FIG. 24a: Mice with subcutaneous B16 tumors were treated by peritumoral injections of CpG-Stat3 siRNA, GpC-Stat3 siRNA, CpG-scrambled RNA, combination of equimolar amounts of uncoupled CpG and Stat3 siRNA or PBS only every other day, starting six days after challenge with 1×10$^5$ B16 cells, n=5-6. Statistically significant differences between CpG-Stat3 siRNA- and CpG-scrambled RNA-treated groups are indicated by asterisks. Similar results were reproduced in three independent experiments. FIG. 24b: Tumor growth inhibition by CpG-Stat3 siRNA depends on NK cell- and T cell-mediated immunity. Mice with established B16 tumors were depleted of NK cell or CD4/CD8 lymphocytes prior to the repeated treatment with CpG-Stat3 siRNA every other day; shown are means±SEM, P<0.0001 (from two-way ANOVA test). FIG. 24c and FIG. 24d: Local treatment with CpG-Stat3 siRNA reduces growth of other tumor models independently of genetic background. C4 melanoma cells (FIG. 24c) and CT26 colon carcinoma cells (FIG. 24d) were injected s.c. into C3H or BALB/c mice, respectively. Mice with established tumors were treated by peritumoral injections of CpG-Stat3 siRNA, CpG-Luc siRNA, CpG alone or PBS every other day, starting seven (C4, CT26) days after challenge with 1×10$^5$ tumor cells. Statistically significant differences between CpG-Stat3 siRNA- and CpG-Luc siRNA-treated groups are indicated by asterisks. FIG. 24e: C57BL/6.CEA mice were challenged s.c. with 1×10$^5$ of MC38.CEA cells and treated as described above using CpG-Stat3 siRNA (left panel) or CpG-Luc siRNA (right panel) starting from day 11. Shown are tumor growth curves for both groups with statistically significant differences indicated by asterisks; P<0.0001 by two-way ANOVA (n=4 for each group). FIG. 24f: Systemic treatment using CpG-Stat3 siRNA reduces Stat3 expression in DCs within tumor-draining cervical lymph nodes. Samples pooled from 6 mice/group were analyzed by real-time PCR. Shown is the average level of Stat3 expression in CpG-Stat3 siRNA-treated mice from one of two independent experiments analyzed in triplicates±SEM in relation to control CpG-scrambled RNA set as 100%. FIG. 24g: Systemic treatment with CpG-Stat3 siRNA reduces the number of B16 tumor metastasis. Mice were i.v. injected with B16 cells and treated with CpG-Stat3 siRNA or CpG-scrambled RNA injections every other day starting from two days post tumor challenge. Lung colonies were enumerated 15 days later when control mice become moribund. Shown are mean numbers of colonies±SEM (n=7), analyzed for statistical significance by two-way ANOVA test; P=0.0054. Representative photos of lung excised from mice inoculated and treated as described above. The in vivo data are representative of two independent experiments.

FIG. 26a: Immunostimulatory cytokine/chemokine gene expression was analyzed in DCs enriched from tumor-draining lymph node cell suspensions pooled from 4-10 mice, prepared after 3 peritumoral injections of CpG-Stat3 siRNA or CpG-Luc siRNA. Data from quantitative real-time PCRs run in triplicates were normalized to GAPDH expression. The averaged results from 4 independent in vivo experiments were combined and analyzed for statistical significance using unpaired t-test with unequal variance. Shown are mean values±SEM; CpG-Luc siRNA was set as a baseline (100%). FIG. 26b: Frozen sections of tumor tissues isolated from mice after treatments as indicated, were stained with antibodies specific to neutrophils (green) and activated caspase-3 (red) and analyzed by fluorescent microscopy. Shown are results of two independent experiments; original magnification: ×100. FIG. 26c: Single cell suspensions prepared from tumors pooled from 3-6 mice were analyzed by flow cytometry for the presence of Gr1+ CD11b− neutrophils. Shown are means±SEM combined from three independent experiments.

FIGS. 28a and 28b show targeting Stat3 using CpG-siRNA augments innate and adaptive antitumor immunity. Effects of in vivo CpG-siRNA treatment on immune cell populations within tumor. Single cell suspensions prepared from tumors pooled from 3-6 mice were analyzed by flow cytometry for the presence of CD4+ (FIG. 28a), CD4+FoxP3+ (FIG. 28b) and CD8+ (FIG. 28c). Shown are means±SEM from combined three independent experiments and representative dot plots (left panels in (FIG. 28b, FIG. 28c). FIG. 28d: Local treatments with CpG-Stat3 siRNA generate tumor antigen-specific immune responses as measured by ELISPOT. IFNγ ELISPOT assays were performed using cell suspensions prepared from four pooled tumor-draining lymph nodes per each treatment group as described in FIG. 3d; presented are the results form one of two independent experiments. Bars represent average numbers of TRP2-specific dots±SEM from triplicate samples; P-values from one-way ANOVA test for statistical significance are indicated.

FIGS. 29a-29c show Stat3 silencing and antitumor responses induced by alternative sequences of Stat3 siRNA conjugated with CpG. FIG. 29a: New Stat3 sequences of single stranded constructs (deoxynucleotides are shown underlined). Mouse Stat3 siRNA #2 (SS): SEQ ID NO:12; CpG1668-mouse Stat3 siRNA #2 (AS): SEQ ID NO:1-linker-SEQ ID NO:13; mouse Stat3 siRNA #3 (SS): SEQ ID NO:14; CpG1668-mouse Stat3 siRNA #2 (AS): SEQ ID NO:1-linker-SEQ ID NO:15. FIG. 29b: New CpG-Stat3 siRNAs stimulate antitumor responses in vivo. Mice with established s.c. B16 tumors (average diameter 10 mm) were treated by peritumoral injections of CpG-Stat3siRNA in two versions or equimolar amounts of CpG-Luc siRNA every other day. Shown are means±SEM; P<0.0001 by two-way ANOVA; statistically significant differences between CpG-Stat3 siRNAs- and CpG-Luc siRNA-treated groups indicated by Bonferroniposttest are indicated by asterisks (n=6). FIG. 29c: Stat3 expression in B cells freshly isolated from tumor-draining lymph nodes was assessed using real-time PCR, comparing Stat3 expression levels in CpG-Stat3 siRNA-treated mice in relation to control CpG-Luc siRNA set as 100%. Shown are means±SEM (n=3); P=0.0018 by one-way ANOVA. This figure shows the validation of CpG-siRNA approach for cancer immunotherapy by using additional siRNAs with different sequences.

FIG. 30a: Freshly isolated PBMCs were incubated for 1 h with 500 nM CpG-Stat3siRNA labeled with FITC. Percentages of fluorescein-positive CD11b+myeloid cells assessed by FACS are indicated. Shown are representative results from one of two independent experiments. FIG. 30b: Stat3silencing is impaired in TLR9-deficient primary myeloid cells (top panel) and dendritic cells (bottom panel); means±SEM (n=3). This figure shows that TLR9 is not necessary for uptake but is required for silencing effect of CpG-Stat3 siRNA by myeloid cells.

FIGS. 31a-31e show that CpG-STAT3 siRNA targets human TLR9-positive tumor cells leading to gene silencing and growth inhibition of xenotransplantmyeloma in mice. FIG. 31a: The uptake of FITC-labeled CpG-STAT3 siRNA by cultured myeloma cells estimated by flow cytometry. FIG. 31b: In vivo internalization of CpG-STAT3 siRNA injected intratumorally. KMS11 tumors grown in NOD/SCID mice were harvested 3 h after injection of various doses of the conjugate and dispersed into single cell suspensions. After removal of CD11b+ myeloid cells and CD19+ B cells, the percentage of FITC+cells was analyzed by FACS. FIGS. 31c-31e: CpG-STAT3 siRNA in vivo treatment leads to STAT3 gene silencing (FIG. 31c), tumor cell death (FIG. 31d) and reduced growth rate of human myeloma tumors in NOD/SCID mice (FIG. 31e). Tumors were treated with daily intratumoral injections of 20 μg CpG-STAT3 siRNA starting 5 days after injection of $1 \times 10^7$ of KMS11 myeloma cells (at the average tumor size 10 mm); P<0.001 (by two-way ANOVA). This figure shows that the CpG-siRNA approach effectively silences genes in TLR9+ human tumor cells leading to therapeutic antitumor effects in animals.

FIGS. 32a-32d show that CpG-STAT3 siRNA approach effectively silences genes in TLR9+human acute myeloid leukemia (AML) cells, leading to therapeutic antitumor effects in xenotransplanted tumor models in mice. FIG. 32a: NOD/SCID/IL-2Rγnull (NSG) mice were injected i.v. with $10^7$ of human MV4-11 leukemia cells. Four weeks later, mice with engrafted AML cells were injected i.v. with the 100 μg dose of various CpG(A)-siRNAs daily for three days. The percentages of viable bone-marrow resident AML tumor cells after treatment using CpG(A)-Luciferase siRNA (top) and CpG(A)-STAT3 siRNA (bottom) were assessed by FACS using antibodies specific for human CD45 expressed on the surface of MV4-11 cells. STAT3 gene silencing was assessed in bone marrow-derived AML cells using quantitative real-time PCR (qPCR) (right graph). FIG. 32b: CpG(A)-STAT3 siRNA in vivo treatment leads to STAT3 gene silencing (left, by qPCR), tumor cell death (middle, by FACS analysis of Annexin V-positive tumor cell suspensions) and reduced growth rate of human myeloma tumors in NSG mice (right). Tumors were treated with daily intratumoral injections of 20 μg CpG-STAT3 siRNA starting 4-5 days after injection of $10^7$ of tumor cells (at the average tumor size 10 mm) Blocking of STAT3 in MonoMac6 cells (FIG. 32c) and BCL-XL in MV4-11 AML cells (FIG. 32d) in vivo inhibits growth of xenotransplanted tumors in NSG mice. The target gene silencing (left graphs in FIG. 32c, 32d), tumor cell death (middle graph in FIG. 32d) and tumor growth kinetics (right panels) were assessed as described above. Statistically significant differences between CpG-STAT3 or BCL-XL siRNA- and CpG-Luc RNA-treated groups (from two-way ANOVA test) are indicated by asterisks as described in the legend for FIG. 34. Shown are the representative results from one of two independent experiments (FIG. 32b) or from single experiments (FIGS. 32a, 32c, 32d) using 5-6 mice per each experimental group; means±s.e.m.

FIG. 33 (top): NOD/SCID/IL-2Rγnull (NSG) mice were injected s.c. with $5 \times 10^6$ of human MV4-11 leukemia cells. Tumors were treated with two daily intratumoral injections of 20 μg various CpG-siRNAs as indicated, including CpG- Luciferase siRNA and CpG-STAT3 siRNA in two versions, conjugated to class A (D19 ODN) or class B (7909) CpG ODN. The STAT3 gene silencing was assessed by quantitative real-time PCR (FIG. 33 (top)), while tumor cell death was measured by FACS analysis using Annexin V staining of tumor cell suspensions (FIG. 33 (bottom)). Shown are the representative results from a single experiments using 5-6 mice per each experimental group; means±s.e.m.

DETAILED DESCRIPTION OF THE INVENTION

Figure 1A:
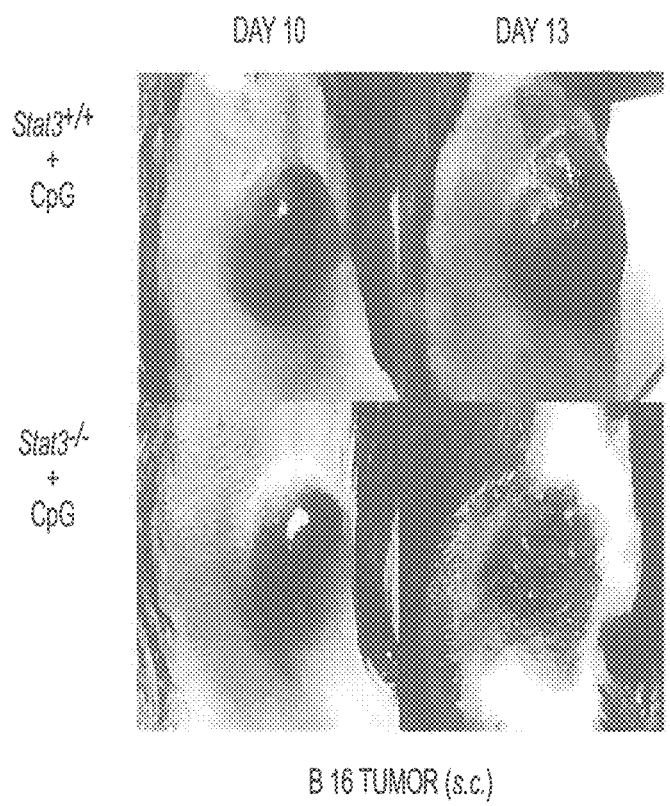

Unless defined otherwise, all technical and scientific terms used herein have the same meaning as is commonly understood by one of skill in the art to which the invention belongs.

The present invention relates to methods and compositions for the treatment of diseases. More particularly, the present invention relates to multifunctional molecules that are capable of being delivered to cells of interest for the treatment of diseases including, but not limited to, cancer, infectious diseases and autoimmune diseases. More specifically, the present invention relates to specific chimeric molecules that are useful for the treatment of diseases.

In one aspect, the present invention provides a novel molecule for the delivery of an active agent into cells for the treatment of cancer and other diseases including, but not limited to infectious diseases and autoimmune diseases. The novel molecules comprises one or more of a first moiety that directs cell or tissue specific delivery of the novel molecule linked to one or more of a second moiety that is an active agent useful for treating cancer or other diseases. The moieties can be linked together directly or they can be linked together indirectly through a linker. In one embodiment, the novel molecule comprises two moieties as one molecule that is multifunctional. For example, a TLR ligand and an siRNA are made into one molecule for delivery, immune stimulation and blocking immunosuppressive elements, such as Stat3, and/or oncogenic effects, such as caused by Stat3. In another embodiment, the novel molecule comprises moieties attached to a linker that is multifunctional, such that it can contain a multitude of moieties. In another embodiment, the linker is bifunctional producing a molecule of the structure A-X-B, where X is a linker, one of A and B is a moiety that is capable of delivering the molecule to cells of interest and the other one of A and B is an active agent useful for treating the cancer or other disease. In another embodiment the linker is a modification of, or structure present on, either moiety A or B, or both, that results in a binding between the two elements. The binding maybe covalent or non-covalent bonds. In another embodiment, the linker is multifunctional, for example, quadrifunctional, producing a molecule having more than two moieties. In one embodiment, such a molecule can have the structure

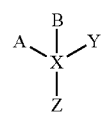

where X is the linker, one or more of A, B, Y and Z is a moiety that is capable of delivering the molecule to cells of interest and the others are an active agent useful for treating the cancer or other disease. The linker may have any number of other moieties attached to it, and the examples of having two or four moieties, and their lack of any secondary extension, for example a modification of Y, is merely for illustration purposes and not intended to be limiting.

In one embodiment, the active agent is a double stranded RNA molecule that either downregulates gene expression, such as a siRNA molecule, or activates gene expression, such as an activating RNA molecule. In another embodiment, the active agent is a small molecule drug or peptide. In one embodiment, the delivery moiety is a ligand for a toll-like receptor (such as oligonucleotides described herein). In another embodiment, the delivery moiety is another cell-specific ligand (such as aptamers).

In a second aspect, the present invention provides a method for the treatment of diseases which comprises using the novel molecules of the present invention. Diseases which can be treated in accordance with the present invention include cancer, infectious diseases, autoimmune diseases, diseases due to excessive angiogenesis and diseases that can benefit from increased angiogenesis. Cancers which can be treated with the molecules of the present invention include, but are not limited to, melanoma, skin cancer, precancerous skin lesions, breast cancer, prostate cancer, lung cancer, glioma, pancreatic cancer, head and neck cancer, multiple myeloma, leukemias, lymphomas. Examples of infectious diseases include, but are not limited to, HIV, HPV infection and hepatitis. Examples of autoimmune diseases include, but are not limited to, psoriasis, multiple sclerosis (MS) and inflammatory bowel disease (IBD). Examples of diseases due to excessive angiogenesis include, but are not limited to, cancer, diabetic retinopathy and Kaposi's Sarcoma. Examples of diseases that can benefit from increased angiogenesis include, but are not limited to, diseases needing wound repair (healing). The molecules of the present invention are administered to patients in need of treatment using conventional pharmaceutical practices.

In a third aspect, the present invention provides active agents that are capable of acting in the Stat3 pathway which, when taken up by the cells of interest, results in the treatment diseases including, but not limited to cancer, infectious diseases and autoimmune diseases.

The molecules of the present invention have several advantages that result from the characteristics of the molecules. These advantages include:

(a) ease of use and cost effectiveness primarily because of a reduction in the need to use transfection reagents;

(b) simplicity primarily because of the ability to make the molecules by chemical synthesis using standard synthesizers;

(c) versatility primarily because the molecules of the present invention can be easily adapted for various gene targets and modified be further modified for small molecule drug or peptide delivery with the use of appropriate chemical linkers; and (d) flexibility primarily because a similar design can be adapted for different cell types capable of ODN or ORN uptake.

An "oligonucleotide" or "oligo" shall mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). The term "oligonucleotide" as used herein refers to both oligoribonucleotides (ORNs) and oligodeoxyribonucleotides (ODNs). The term "oligonucleotide" shall also include oligonucleosides (i.e. an oligonucleotide minus the phosphate) and any other organic base containing polymer. Oligonucleotides can be obtained from existing nucleic acid sources (e.g. genomic or cDNA), but are preferably synthetic (e.g. produced by oligonucleotide synthesis).

A "stabilized oligonucleotide" shall mean an oligonucleotide that is relatively resistant to in vivo degradation (e.g. via an exo- or endo-nuclease). Preferred stabilized oligonucleotides of the instant invention have a modified phosphate backbone. Especially preferred oligonucleotides have a phosphorothioate modified phosphate backbone (i.e. at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

A "CpG containing oligonucleotide," "CpG ODN" or "CpG ORN" refers to an oligonucleotide, which contains a cytosine/guanine dinucleotide sequence. Preferred CpG oligonucleotides are between 2 to 100 base pairs in size and contain a consensus mitogenic CpG motif represented by the formula:

wherein C and G are unmethylated, $X_1$, $X_2$, $X_3$ and $X_4$ are nucleotides and a GCG trinucleotide sequence is not present at or near the 5' and 3' ends. Examples of CpG ODNs are described in U.S. Pat. Nos. 6,194,388 and 6,207,646, each incorporated herein by reference. Preferably the CpG oligonucleotides range between 8 and 40 base pairs in size. In addition, the CpG oligonucleotides are preferably stabilized oligonucleotides, particularly preferred are phosphorothioate stabilized oligonucleotides. The CpG ODNs or CpG ORNs can be synthesized as an oligonucleotide. Alternatively, CpG ODNs or CpG ORNs can be produced on a large scale in plasmids.

An "aptamer" refers to a nucleic acid molecule that is capable of binding to a particular molecule of interest with high affinity and specificity (Tuerk and Gold, 1990; Ellington and Szostak, 1990). The binding of a ligand to an aptamer, which is typically RNA, changes the conformation of the aptamer and the nucleic acid within which the aptamer is located. The conformation change inhibits translation of an mRNA in which the aptamer is located, for example, or otherwise interferes with the normal activity of the nucleic acid. Aptamers may also be composed of DNA or may comprise non-natural nucleotides and nucleotide analogs. An aptamer will most typically have been obtained by in vitro selection for binding of a target molecule. However, in vivo selection of an aptamer is also possible. An aptamer will typically be between about 10 and about 300 nucleotides in length. More commonly, an aptamer will be between about 30 and about 100 nucleotides in length. See, e.g., U.S. Pat. No. 6,949,379, incorporated herein by reference. Examples of aptamers that are useful for the present invention include, but are not limited to, PSMA aptamer (McNamara et al., 2006), CTLA4 aptamer (Santulli-Marotto et al., 2003) and 4-1BB aptamer (McNamara et al., 2007).

As used herein, the terms "Toll-like receptor" or "TLR" refer to any member of a family of at least ten highly conserved mammalian pattern recognition receptor proteins (TLR1-TLR10) which recognize pathogen-associated molecular patterns (PAMPs) and act as key signaling elements in innate immunity. TLR polypeptides share a characteristic structure that includes an extracellular (extracytoplasmic) domain that has leucine-rich repeats, a transmembrane domain, and an intracellular (cytoplasmic) domain that is involved in TLR signaling. TLRs include, but are not limited, to human TLRs. TLRs include, but are not limited to TLR9, TLR8 and TLR3.

As used herein, the terms "TLR ligand" or "ligand for a TLR" refer to a molecule, that interacts, directly or indirectly, with a TLR through a TLR domain and is capable of being internalized by cells. In one embodiment a TLR ligand is a natural ligand, i.e., a TLR ligand that is found in nature. In one embodiment a TLR ligand refers to a molecule other than a natural ligand of a TLR, e.g., a molecule prepared by human activity, such as a CpG containing oligonucleotide.

In accordance with the present invention, target cells for ODN- or ORN-mediated delivery include any cell that is capable of internalizing a TLR ligand. Such cells include (a) cells of the myeloid lineage including dendritic cells, macrophages and monocytes, (b) cells of the lymphoid lineage including B cells and T cells, (c) endothelial cells and (d) malignant cells being derivatives of the previously mentioned cells, e.g., multiple myeloma, B cell lymphoma and T cell lymphoma. The malignant cells can also be any cells that possess the capacity of uptaking and/or internalizing a TLR ligand.

In accordance with the present invention, novel molecules are provided by an active moiety for delivering an active agent to a cell of interest for the treatment of diseases as disclosed herein. The novel molecules comprises one or more of a first moiety that directs cell or tissue specific delivery of the novel molecule linked to one or more of a second moiety that is an active agent useful for treating cancer or other diseases. The moieties can be linked together directly or they can be linked together indirectly through a linker. In one embodiment, the novel molecule comprises two moieties as one molecule that is multifunctional. For example, a TLR ligand and an siRNA are made into one molecule for delivery, immune stimulation and blocking immunosuppressive elements, such as Stat3, and/or oncogenic effects, such as caused by Stat3. In another embodiment, the novel molecule comprises moieties attached to a linker that is multifunctional, such that it can contain a multitude of moieties. The linkage of the first and second moieties can be provided through diverse structures and/or chemistry. The linkage can also be designed to allow for one first moiety to be linked to multiple second moieties. The linkage can be designed to allow for linkage of a first moiety to small molecule drugs or peptides.

In one embodiment, the molecule may have the structure A-X-B. In another embodiment, the molecule may have the structure

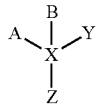

where X is a linker between the A and B moieties or between the A, B, Y and Z moieties. In one embodiment, we can make 2 or (n)-element chains, stars, branches (or mixtures thereof) etc and defining the chemistry and valency of the linker(s). Valency can be substrate specific to control polymerization. In one embodiment, X may be multifunctional reactive molecule having, e.g., NNP, where N is a nucleic acid binding sites and P is a peptide binding site. The linker may be derivatized, e.g., with FITC, such that the X moiety itself is also functional. In this embodiment, X may be derivatized with a fluorochrome or similar molecule, or may be derivatized with a chemotherapeutic agent.

In one embodiment, A, B, etc., i.e., any moiety attached to the linker, can be small molecules, peptides, polypeptides, proteins, antibodies and fragments thereof, other molecules such as lectins, DNA, RNA, ds RNA ds DNA, RNA/DNA hybrids (and modifications thereto), locked nucleic acids, RNA with 5' triphosphates, antibodies, antibody fragments, antigens or antigen fragments.

In one embodiment, the function of A, B, etc., i.e., any moiety attached to the linker, can be selected to include from delivery (including approaches to target to cells, tissues, organs), improved pharmacokinetic properties, cytotoxic, cytostatic, apoptotic, gene modulating (including upregulation, e.g., activating RNA, or downregulation, e.g., siRNA), pro-inflammatory, anti-inflammatory, antigenic, immunogenic pro-coagulant, anti-coagulant properties, pro-drug elements and combinations thereof. In another embodiment, each of these moieties can modified as known in current state of art to improve their desired properties. These (A, B or desired modifications) can also be selected for via screening, evolution or combinatorial approaches as is well known to the skilled artisan.

In one embodiment, moieties that can be used for delivery include CpG ODNs, CpG ORNs, polyG (Peng et al., 2005), poly(I:C) (Alexopoulou et al., 2001) (such as ligands for toll-like receptors (TLRs)) and aptamers. The TLR ligands are useful for delivering the molecules of the present invention to cells that are capable of internalizing TLR ligands. Aptamers are useful for delivering the molecules of the present invention to cells which specifically bind the aptamers.

In one embodiment, some elements or moieties may be themselves bifunctional or derivatized to be bifunctional or have improved function (e.g., adding a 5' triphosphate on a CpG may be an enhanced stimulator of intracellular and/or extracellular signaling).

The present invention also provides for linkers and/or methods for providing the molecules of the present invention. In one embodiment, a molecule of the present invention is prepared by linking a first moiety, e.g. a CpG ODN, CpG ORN, oligonucleotides or aptamer, to a second moiety, e.g., a dsRNA, using multiple units of the C3 spacer as the linker (Dela et al., 1987). A method for preparing such a molecule in which the first moiety is a CpG ODN is shown in the Examples.

In an embodiment in which the first moiety is an ODN, ORN, oligonucleotides or aptamer and the second moiety is a dsRNA, a molecule of the present invention can be prepared by providing a dsRNA in which one of the strands has an overhang and the first moiety has a complementary overhang. The overhang can be spaced from the first moiety and the dsRNA by using linkers comprising multiple units of the C3 spacer. After annealing, both components are connected creating a desired construct. By controlling the length of the overhang and its makeup we can control the strength and the specificity of the attachment. The preferred component of the overhang are: 2'-O-methyl RNA (2'-OMe), 2'-Fluoro RNA (2'-F) or Locked Nucleic Acids (LNAs) or PNA. Extremely high melting temperatures of an LNA/LNA duplex allow for the use of much shorter overhangs. 2'-Fluoro RNA (2'-F) were reported to have lower toxicity then 2'-O-methyl RNA (2'-OMe). Since the cost of LNA is still 10-15 times higher then 2'-Fluoro RNA (2'-F) the latter seems to be the optimal choice for overhang component. Use of all of the above increases the resistance of the oligonucleotide to cellular nucleases. See, for example, Kurreck et al. (2002, Braasch et al. (2002) and Braasch et al. (2003). The other exemplary sugar modifications include, for example, a 2'-O-methoxyethyl nucleotide, a 2'-O-NMA, a 2'-DMAEOE, a 2'-AP, 2'-hydroxy, or a 2'-arafluoro or extended nucleic acid (ENA), hexose nucleic acid (HNA), or cyclohexene nucleic acid (CeNA). The use of overhangs for the construction allows for: (i) use of smaller molecules, (ii) higher purity at lower cost, (iii) lower cost of final product and (iv) flexibility (construction of product on demand; possibility of matching of one component with multiple components). The use of a universal overhangs allows for the interchangeability of the components.

The use of branching or bridging compounds allows for the synthesis of a component carrying two or more overhangs. Such branching or bridging compounds allows for the attachment of multiple first moiety components, e.g., CpG ODN, to the second moiety component, e.g., dsRNA, and/or for the attachment of multiple second moiety components to the multiple first moiety components. The use of molecules having in multiple overhangs allows for the assembly of complementary constructs consisting of two or more aptamers. Constructs of this kind would be used in the dimerization experiments. The use of molecules having multiple overhangs allows for the assembly of complementary constructs consisting of an aptamer and two or more siRNA duplexes.

Covalent constructs can also be prepared to form the molecules of the present invention. In this embodiment, the first and second moieties have reactive groups. A covalent bond is created during the chemical reaction between the reactive groups. Examples of such pairs of the reactive groups are as follows.

(A) carboxyl group and amino group. The attachment to be achieved by creating a covalent bond between the carboxyl group on one component and the amino group at the other component; it is possible to use a carbodimide to create the covalent bond.

(B) azide and acetylene groups. These groups combine readily with each other—when held in close proximity—to form triazoles. Click chemistry is the use of chemical building blocks with "built-in high-energy content to drive a spontaneous and irreversible linkage reaction with appropriate complementary sites in other blocks." Use of the azide-acetylene reaction represents "true progress" because of its high selectivity.

(C) vinyl sulfones and sulfuhydryl group, vinyl sulfones and terminal phosphothioesters, vinyl sulfones and amino group. Vinyl sulfones and substituted divinyl sulfones readily react with sulfuhydryl group (SH) in pH 5-7, with and terminal phosphothioesters in pH7, and with primary and secondary amines at higher pH.

Conjugation of two biopolymers with the use of click chemistry (as described above) can also be used to create the molecules of the present invention. Reaction of dsRNA component having multiple reactive groups with the excess of the CPG or aptamer component leads to the products consisting of multiple dsRNAs attached to the single CPG or aptamer component. Reaction of first moiety having multiple reactive groups with the excess of the small molecule drug leads to the products consisting of multiple drug molecules attached to a single CpG or aptamer component. Drugs may be attached to the constructs through the hydrolysable-digestible linker, such as a short peptide hydrolysable by esterase, to facilitate its release upon delivery to the target.

In one aspect, the active agents of the present invention are double stranded RNA molecules. These double stranded RNA molecules may be useful for downregulating gene expression, such as siRNA molecules. Alternatively, the double stranded RNA molecules may be useful for upregulating gene transcription, such as activating RNA molecules.

The siRNA molecule may have different forms, including a single strand, a paired double strand (dsRNA) or a hairpin (shRNA) and can be produced, for example, either synthetically or by expression in cells. In one embodiment, DNA sequences for encoding the sense and antisense strands of the siRNA molecule to be expressed directly in mammalian cells can be produced by methods known in the art, including but not limited to, methods described in U.S. published application Nos. 2004/0171118, 2005/0244858 and 2005/0277610, each incorporated herein by reference. The siRNA molecules are coupled to carrier molecules, such as CpG oligonucleotides, various TLR-ligands (such as polyG or poly(I:C) or RNA aptamers, using the techniques known in the art or described herein.

In one aspect, DNA sequences encoding a sense strand and an antisense strand of a siRNA specific for a target sequence of a gene are introduced into mammalian cells for expression. To target more than one sequence in the gene (such as different promoter region sequences and/or coding region sequences), separate siRNA-encoding DNA sequences specific to each targeted gene sequence can be introduced simultaneously into the cell. In accordance with another embodiment, mammalian cells may be exposed to multiple siRNAs that target multiple sequences in the gene.

The siRNA molecules generally contain about 19 to about 30 base pairs, and may be designed to cause methylation of the targeted gene sequence. In one embodiment, the siRNA molecules contain about 19-23 base pairs, and preferably about 21 base pairs. In another embodiment, the siRNA molecules contain about 24-28 base pairs, and preferably about 26 base pairs. In a further embodiment, the dsRNA has an asymmetric structure, with the sense strand having a 25-base pair length, and the antisense strand having a 27-base pair length with a 2 base 3'-overhang. See, for example, U.S. published application Nos. 2005/0244858, 2005/0277610 and 2007/0265220, each incorporated herein by reference. In another embodiment, this dsRNA having an asymmetric structure further contains 2 deoxynucleotides at the 3' end of the sense strand in place of two of the ribonucleotides. Individual siRNA molecules also may be in the form of single strands, as well as paired double strands ("sense" and "antisense") and may include secondary structure such as a hairpin loop. Individual siRNA molecules could also be delivered as precursor molecules, which are subsequently altered to give rise to active molecules. Examples of siRNA molecules in the form of single strands include a single stranded anti-sense siRNA against a non-transcribed region of a DNA sequence (e.g. a promoter region).

The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3'end of antisense strand and are sufficiently complementary to a nucleotide sequence of the RNA produced from the target gene.

The RNAi molecule, may also have one or more of the following additional properties: (a) the antisense strand has a right shift from the typical 21mer and (b) the strands may not be completely complementary, i.e., the strands may contain simple mismatch pairings. A "typical" 21mer siRNA is designed using conventional techniques, such as described above. This 21mer is then used to design a right shift to include 1-7 additional nucleotides on the 5' end of the 21mer. The sequence of these additional nucleotides may have any sequence. Although the added ribonucleotides may be complementary to the target gene sequence, full complementarity between the target sequence and the siRNA is not required. That is, the resultant siRNA is sufficiently complementary with the target sequence. The first and second oligonucleotides are not required to be completely complementary. They only need to be substantially complementary to anneal under biological conditions and to provide a substrate for Dicer that produces a siRNA sufficiently complementary to the target sequence. In one embodiment, the dsRNA has an asymmetric structure, with the antisense strand having a 25-base pair length, and the sense strand having a 27-base pair length with a 2 base 3'-overhang. In another embodiment, this dsRNA having an asymmetric structure further contains 2 deoxynucleotides at the 3'end of the antisense strand.

Suitable dsRNA compositions that contain two separate oligonucleotides can be linked by a third structure. The third structure will not block Dicer activity on the dsRNA and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the dsRNA is a manner such that a hairpin structure is produced upon annealing of the two oligonucleotides making up the dsRNA composition. The hairpin structure will not block Dicer activity on the dsRNA and will not interfere with the directed destruction of the RNA transcribed from the target gene.

The sense and antisense sequences may be attached by a loop sequence. The loop sequence may comprise any sequence or length that allows expression of a functional siRNA expression cassette in accordance with the invention. In a preferred embodiment, the loop sequence contains higher amounts of uridines and guanines than other nucleotide bases. The preferred length of the loop sequence is about 4 to about 9 nucleotide bases, and most preferably about 8 or 9 nucleotide bases.

In another embodiment of the present invention, the dsRNA, i.e., the RNAi molecule, has several properties which enhances its processing by Dicer. According to this embodiment, the dsRNA has a length sufficient such that it is processed by Dicer to produce an siRNA and at least one of the following properties: (i) the dsRNA is asymmetric, e.g., has a 3' overhang on the sense strand and (ii) the dsRNA has a modified 3' end on the antisense strand to direct orientation of Dicer binding and processing of the dsRNA to an active siRNA. According to this embodiment, the longest strand in the dsRNA comprises 24-30 nucleotides. In one embodiment, the sense strand comprises 24-30 nucleotides and the antisense strand comprises 22-28 nucleotides. Thus, the resulting dsRNA has an overhang on the 3' end of the sense strand. The overhang is 1-3 nucleotides, such as 2 nucleotides. The antisense strand may also have a 5' phosphate.

Modifications can be included in the dsRNA, i.e., the RNAi molecule, so long as the modification does not prevent the dsRNA composition from serving as a substrate for Dicer. In one embodiment, one or more modifications are made that enhance Dicer processing of the dsRNA. In a second embodiment, one or more modifications are made that result in more effective RNAi generation. In a third embodiment, one or more modifications are made that support a greater RNAi effect. In a fourth embodiment, one or more modifications are made that result in greater potency per each dsRNA molecule to be delivered to the cell. Modifications can be incorporated in the 3'-terminal region, the 5'-terminal region, in both the 3'-terminal and 5'-terminal region or in some instances in various positions within the sequence. With the restrictions noted above in mind any number and combination of modifications can be incorporated into the dsRNA. Where multiple modifications are present, they may be the same or different. Modifications to bases, sugar moieties, the phosphate backbone, and their combinations are contemplated. Either 5'-terminus can be phosphorylated.

In another embodiment, the antisense strand is modified for Dicer processing by suitable modifiers located at the 3' end of the antisense strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is an asymmetric composition with DNA on the blunt end and RNA bases on the overhanging end.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988, 6,291,438 and 7,307,069 and in U.S. published patent application No. 2004/0203145, each incorporated herein by reference. Other modifications are disclosed in Herdewijn (2000), Eckstein (2000), Rusckowski et al. (2000), Stein et al. (2001) and Vorobjev et al. (2001), each incorporated herein by reference.

Additionally, the siRNA structure can be optimized to ensure that the oligonucleotide segment generated from Dicer's cleavage will be the portion of the oligonucleotide that is most effective in inhibiting gene expression. For example, in one embodiment of the invention a 27-bp oligonucleotide of the dsRNA structure is synthesized wherein the anticipated 21 to 22-bp segment that will inhibit gene expression is located on the 3'-end of the antisense strand. The remaining bases located on the 5'-end of the antisense strand will be cleaved by Dicer and will be discarded. This cleaved portion can be homologous (i.e., based on the sequence of the target sequence) or non-homologous and added to extend the nucleic acid strand.

Activating RNA molecules are similar in design as siRNA molecules. However, they can also be shorter than siRNA molecules. Thus, activating RNA molecules may be 12-30 nucleotides in length, although a length of 18-30 nucleotides is preferred. Activating RNA molecules are targeted to the promoter region of the gene of interest and are designed to induce transcriptional activation. In one embodiment, the region within the promoter of the gene is selected from a partially single-stranded structure, a non-B-DNA structure, an AT-rich sequence, a cruciform loop, a G-quadruplex, a nuclease hypersensitive elements (NHE), and a region located between nucleotides −100 to +25 relative to a transcription start site of the gene. See, for example, Li et al. (2006), Kuwabara et al. (2005), Janowski et al. (2007) and U.S. published application No. 2007/0111963, each incorporated herein by reference. A broad spectrum of chemical modifications can be made to duplex RNA, without negatively impacting the ability of the dsRNA to selectively increase synthesis of the target transcript. These chemical modifications included those described above for siRNA molecules as well as those described in U.S. published application No. 2007/0111963.

RNA for the siRNA or activating RNA component of the present invention may be produced enzymatically or by partial/total organic synthesis, and modified ribonucleotides can be introduced by in vitro enzymatic or organic synthesis. In one embodiment, each strand is prepared chemically. Methods of synthesizing RNA molecules are known in the art, in particular, the chemical synthesis methods as described in Verma and Eckstein (1998).

In another aspect, the active agents of the present invention are small molecule drugs or peptides. Examples of small molecule drugs include, but are not limited to, Stat3 inhibitors (such as those commercially available from Calbiochem), Imatinib (Bcr-Abl), Sunitib (VEGF receptor), Sorefenib (Raf) and DASATINIB (Src). Examples of peptides include, but are not limited to, Stat3 peptidomimetics, p53 peptidomimetics and Farnesyl Transferase inhibitors.

The present invention further provides active agents that are capable of acting in the Stat3 signaling pathway or affecting genes regulated by Stat3. These active agents, when taken up by the cells of interest, result in the treatment of cancer or other diseases. In one embodiment, the active agent is an siRNA molecule directed against Stat3 and results in the down regulation of Stat3. In another embodiment, the active agent is an siRNA molecule directed against SOCS3 which is an inhibitor of Stat3. In a further embodiment, the active agent is an activating RNA for tumor suppressor genes.

In addition, the present invention provides a method for treating diseases. The molecules of the present invention are administered to patients in need of treatment using conventional pharmaceutical practices. Suitable pharmaceutical practices are described in *Remington: The Science and Practice of Pharmacy*, 21$^{st}$ Ed., University of Sciences in Philadelphia, Ed., Philadelphia, 2005. In one embodiment, the present invention provides for the delivery of dsRNA, such as siRNA or activating RNA, for the treatment of cancer. In another embodiment, the present invention provides for the delivery of dsRNA for the treatment of infectious diseases. In a further embodiment, the present invention provides the delivery of dsRNA for the treatment of autoimmune diseases. The dsRNA can be specifically delivered to cells as described herein.

The present invention can also be used to deliver DNA or RNA that encode antigens to cells, e.g., DCs to stimulate an immune response, e.g., vaccine or immunomodulator. Suitable antigens could be tumor or infectious agents, including but not limited to, virus, fungus, bacteria, rikettsia, amoeba.

Thus, the present invention relates to the use of multifunctional molecules to modulate cancer and the immune system. The present invention relates delivery of RNA (siRNA and/or activating RNA) by TLR ligands as single molecule in vivo. The present invention is illustrated herein by a covalently linked siRNA and CpG molecule. In particular, we show the (mouse) CpG motif coupled to a 27mer siRNA against Stat-3. Other TLR ligands, including but not limited to polyI:C, polyG LPS, and peptidoglycan can also been linked to siRNAs for various target genes.

Stat3 is a 'master switch'—in both cancer and tumor cells and tumor-associated immune cells—that controls tumor survival, angiogenesis/metastasis and immune evasion. The challenge is to turn Stat3 off in the desired cells in cancer in patients. The present invention describes the development of optimal Stat3 siRNAs (Dicer) with antitumor effects in vivo, and shows that Stat3siRNA linked to CpG oligonucleotide efficiently enters dendritic cells. Targeting Stat3 drastically improves CpG-based cancer. The utility of the present invention has been demonstrated herein using melanoma as the model. However, it is understood that the present invention is not limited to melanoma but is equally applicable to all types of cancer.

Many promising immunotherapeutic approaches are in clinical trials for melanoma patients. However, these approaches face a major challenge: tumor-induced immune suppression. Since Stat3 is a key mediator of tumor-induced immunosuppression in melanoma, we reasoned that targeting Stat3—although not perfect with current drugs—will significantly improve the tumor immunologic microenvironment and thus enhance various immunotherapeutic approaches. As demonstrated herein, targeting Stat3 dramatically improves CpG ODN-based melanoma immunotherapy. We show that inhibiting Stat3 in myeloid cells, in conjunction with local CpG treatment, can eliminate large (1.5 cm in diameter) established B16 melanomas. We also demonstrate that targeting Stat3 systemically with a small-molecule Stat3 inhibitor not only dramatically improve the antitumor effects at primary tumor sites receiving CpG injection but also leads to concomitant antitumor effects on distal tumors without CpG treatment. In addition to the potent antitumor effects, our results indicate that blocking Stat3 in tumor-stromal immune cells activates Stat1 and NF-κB, leading to Th-1 immune responses of diverse immune subsets that are fundamental for numerous cancer immunotherapies. Consistent with the idea that targeting Stat3 can improve immunotherapeutic efficacies are the findings by Kirkwood and colleagues (Kirkwood et al., 1999), who demonstrated that high dose IFNα-based immunotherapy response inversely correlates with Stat3 activity in melanoma patients.

In another aspect, the present invention provides for a pharmaceutical composition comprising of molecules of the present invention, i.e., the molecules that contain a cell specific delivery moiety and one or more additional active agents. The cell specific delivery moiety and the additional active agent(s) may be directly linked together or they may be indirectly linked together through the use of a linker. As described herein, the active agent may be an siRNA, an activating RNA, a small molecule drug or a peptide. These molecules can be suitably formulated and introduced into the environment of the cell by any means that allows for a sufficient portion of the sample to enter the cell to induce gene silencing, if it is to occur. Many formulations for dsRNA are known in the art and can be used for delivery of the molecules of the present invention to mammalian cells so long as active agent gains entry to the target cells so that it can act. See, e.g., U.S. published patent application Nos. 2004/0203145 A1 and 2005/0054598 A1, each incorporated herein by reference. For example, siRNA can be formulated in buffer solutions such as phosphate buffered saline solutions, liposomes, micellar structures, and capsids. Formulations of siRNA with cationic lipids can be used to facilitate transfection of the dsRNA into cells. For example, cationic lipids, such as lipofectin (U.S. Pat. No. 5,705,188, incorporated herein by reference), cationic glycerol derivatives, and polycationic molecules, such as polylysine (published PCT International Application WO 97/30731, incorporated herein by reference), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

It can be appreciated that the method of introducing the molecules of the present invention into the environment of the cell will depend on the type of cell and the make up of its environment. For example, when the cells are found within a liquid, one preferable formulation is with a lipid formulation such as in lipofectamine and the molecules of the present invention can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate molecules of the present invention in a buffer or saline solution and directly inject the formulated dsRNA into cells, as in studies with oocytes. The direct injection of dsRNA duplexes may also be done. For suitable methods of introducing siRNA see U.S. published patent application No. 2004/0203145 A1, incorporated herein by reference.

Suitable amounts of molecules of the present invention must be introduced and these amounts can be empirically determined using standard methods. Typically, effective concentrations of individual dsRNA species in the environment of a cell will be about 50 nanomolar or less 10 nanomolar or less, or compositions in which concentrations of about 1 nanomolar or less can be used. In other embodiment, methods utilize a concentration of about 200 picomolar or less and even a concentration of about 50 picomolar or less can be used in many circumstances. Typically, effective doses of small molecule drugs or peptides can be lower than previously used in view of the cell specific delivery provided by the present invention.

The method can be carried out by addition of the compositions containing the molecules of the present invention to any extracellular matrix in which cells can live provided that the composition is formulated so that a sufficient amount of the active agent can enter the cell to exert its effect. For example, the method is amenable for use with cells present in a liquid such as a liquid culture or cell growth media, in tissue explants, or in whole organisms, including animals, such as mammals and especially humans.

Expression of a target gene can be determined by any suitable method now known in the art or that is later developed. It can be appreciated that the method used to measure the expression of a target gene will depend upon the nature of the target gene. For example, when the target gene encodes a protein the term "expression" can refer to a protein or transcript derived from the gene. In such instances the expression of a target gene can be determined by measuring the amount of mRNA corresponding to the target gene or by measuring the amount of that protein. Protein can be measured in protein assays such as by staining or immunoblotting or, if the protein catalyzes a reaction that can be measured, by measuring reaction rates. All such methods are known in the art and can be used. Where the gene product is an RNA species expression can be measured by determining the amount of RNA corresponding to the gene product. The measurements can be made on cells, cell extracts, tissues, tissue extracts or any other suitable source material.

The determination of whether the expression of a target gene has been reduced can be by any suitable method that can reliably detect changes in gene expression. Typically, the determination is made by introducing into the environment of a cell undigested siRNA such that at least a portion of that siRNA enters the cytoplasm and then measuring the expression of the target gene. The same measurement is made on identical untreated cells and the results obtained from each measurement are compared. Similarly the determination can be made by introducing into the environment of a cell undigested activating RNA such that at least a portion of that activating RNA enters the cytoplasm and then measuring the expression of the target gene.

The molecules of the present invention can be formulated as a pharmaceutical composition which comprises a pharmacologically effective amount of the molecules and pharmaceutically acceptable carrier. A pharmacologically or therapeutically effective amount refers to that amount of a molecule of the present invention effective to produce the intended pharmacological, therapeutic or preventive result. The phrases "pharmacologically effective amount" and "therapeutically effective amount" or simply "effective amount" refer to that amount of a dsRNA, small molecule drug or peptide effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA composition may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general a suitable dosage unit of active agent moiety of the molecules of the present invention will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the siRNA can be administered once daily. However, the therapeutic agent may also be dosed in dosage units containing two, three, four, five, six or more sub-doses administered at appropriate intervals throughout the day. In that case, the active agent, e.g., dsRNA, contained in each sub-dose must be correspondingly smaller in order to achieve the total daily dosage unit. The dosage unit can also be compounded for a single dose over several days, e.g., using a conventional sustained release formulation which provides sustained and consistent release of the active agent, e.g., dsRNA, over a several day period. Sustained release formulations are well known in the art. In this embodiment, the dosage unit contains a corresponding multiple of the daily dose. Regardless of the formulation, the pharmaceutical composition must contain active agent, e.g., dsRNA, in a quantity sufficient to inhibit expression of the target gene in the animal or human being treated. The composition can be compounded in such a way that the sum of the multiple units of active agent together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

In a further aspect, the present invention relates to a method for TGS in a mammalian, including human, cell. The method comprises introducing the siRNA containing molecules of the present invention into the appropriate cell. The term "introducing" encompasses a variety of methods of introducing the siRNA containing molecules into a cell, either in vitro or in vivo, such as described above.

In a further aspect, the present invention relates to a method for gene activation in a mammalian cell, including human cell. The method comprises introducing the activating RNA containing molecules of the present invention into the appropriate cell. The term "introducing" encompasses a variety of methods of introducing the siRNA containing molecules into a cell, either in vitro or in vivo, such as described above.

In a further aspect, the present invention relates to a method for treating a disease or physiological disorder or condition in a mammal, including a human. The method comprises introducing the small molecule drug or peptide containing molecules of the present invention into the appropriate cell. The term "introducing" encompasses a variety of methods of introducing the siRNA containing molecules into a cell, either in vitro or in vivo, such as described above.

TLR ligands, such as CpG, are known to stimulate innate immunity. The present invention illustrates that blocking Stat3, either genetically, or pharmacologically, results in drastically improved immune responses and antitumor effects.

A major challenge facing siRNA-based therapies is efficient uptake of siRNA by desired cells in vivo. The present studies demonstrate that a TLR ligand, e.g., a moiety consisting of oligonucleotides that can activate immune responses against cancer and infectious diseases when it is linked to siRNA, is able to mediate siRNA uptake and internalization by desired immune cells. They include myeloid cells, such as macrophages and dendritic cells, in cultured cells, and in animals through either intratumoral or intravenous injections of the chimeric constructs. This uptake occurs in the absence of any transfection agents. The DNA-RNA chimeric constructs can be processed by Dicer and is associated with Dicer in living cells. In vivo delivery of the chimeric constructs results in gene silencing in DCs and macrophages, including those reside in tumors and the tumor draining lymph nodes. Similar construct involving TLR ligand and siRNA can also be uptaken by human monocytes, leading to gene silencing.

In addition to macrophages, dendritic cells and monocytes, the present studies show that the CpG-siRNA chimeric constructs can be efficiently taken up by both human and mouse B cell malignant cells (B cell lymphoma and multiple myeloma).

Stat3 is a potent oncogenic transcriptional factor that is continuously activated in diverse human cancer (Yu and Jove, 2004). Activated Stat3 not only promotes tumor cell survival, proliferation and angiogenesis (Yu and Jove, 2004), it also mediates tumor immune suppression through its activation in both tumor cells and in immune cells in the tumor microenvironment (Wang et al., 2004; Kortylewski et al., 2005b; Yu et al., 2007). Effective targeting of Stat3 in tumor cells has been shown to induce tumor cell apoptosis, inhibit tumor cell proliferation, angiogenesis/metastasis (Yu and Jove, 2004). Inhibiting Stat3 in both tumor cells and/or immune cells also elicits multi-component antitumor immune responses (Wang et al., 2004; Kortylewski et al., 2005b). Although CpG is a potent immune stimulator, its effects in tumor-bearing hosts are dampened by the tumor microenvironment, which is, at least in part, mediated by Stat3 activation. Interestingly, CpG, like several other pathogen-associated immune stimulators, such as LPS, is an activator of Stat3 (through activating IL-10, which in turn activates Stat3), and Stat3 serves as feedback mechanism to limit their immunostimulatory effects (Benkhart et al., 2000; Samarasinghe et al., 2006). These findings suggest that triggering toll-like receptor through its ligand while blocking Stat3 should negate the inhibitory effects associated with CpG, thereby generating potent immune responses and improving CpG treatment for both cancer and infectious diseases. Our data generated with CpG treatment in conjunction with genetic knockout of Stat3 in myeloid cells prove this point. These data illustrate that blocking Stat3, by any means, are highly desirable for enhancing the efficacies of TLR ligand-based therapies. See data and Examples herein. See also U.S. Patent Application Publication No. 2008/02144356, PCT International Publication No. WO 2008/094254, and U.S. Patent Application Publication No. 2011/0071210, each incorporated herein in its entirety for all that it discloses.

Figure 2A:
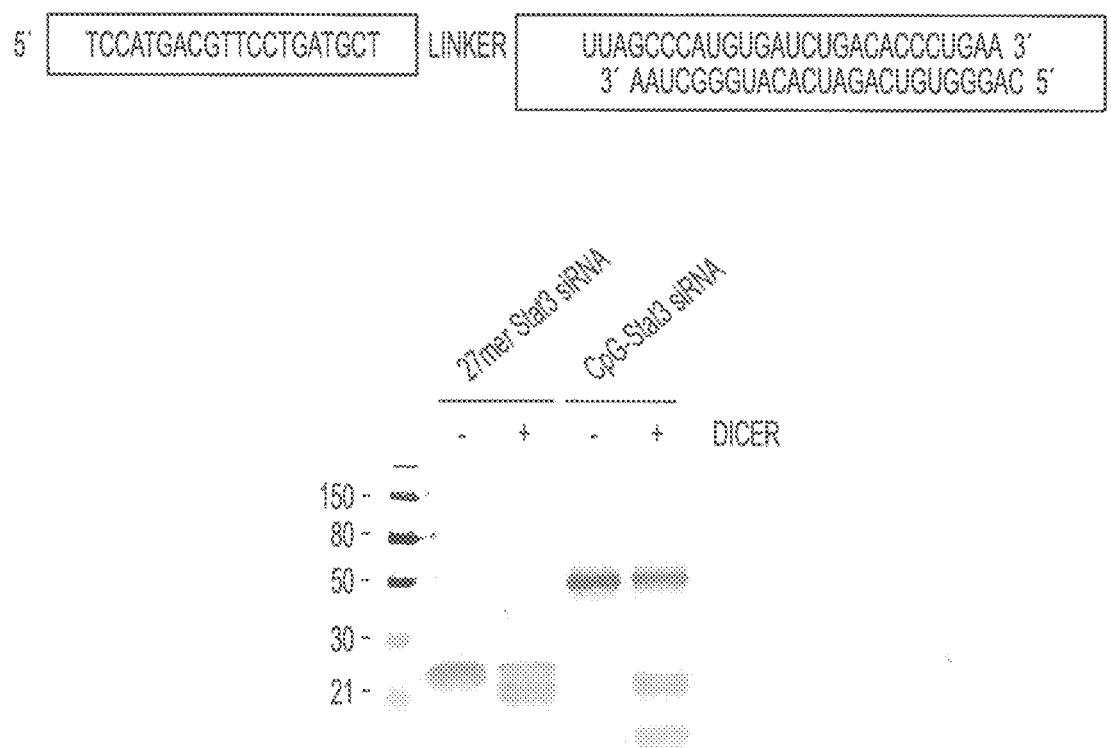
FIGS. 2a-2f show that Stat3 siRNA fusion construct mediates Stat3 silencing in TLR9$^+$ dendritic cells and macrophages.
Figure 2B:
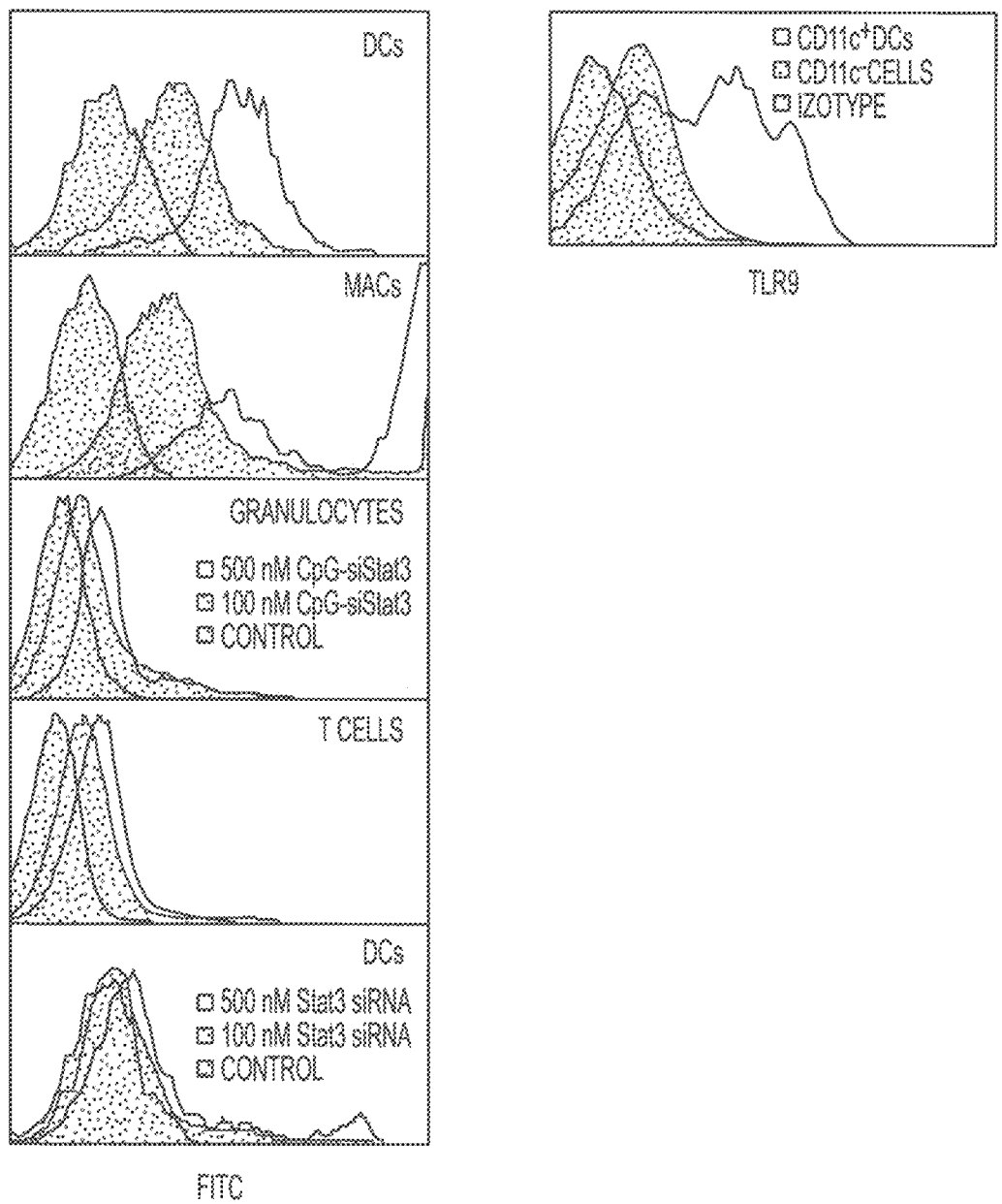
Figure 2C:
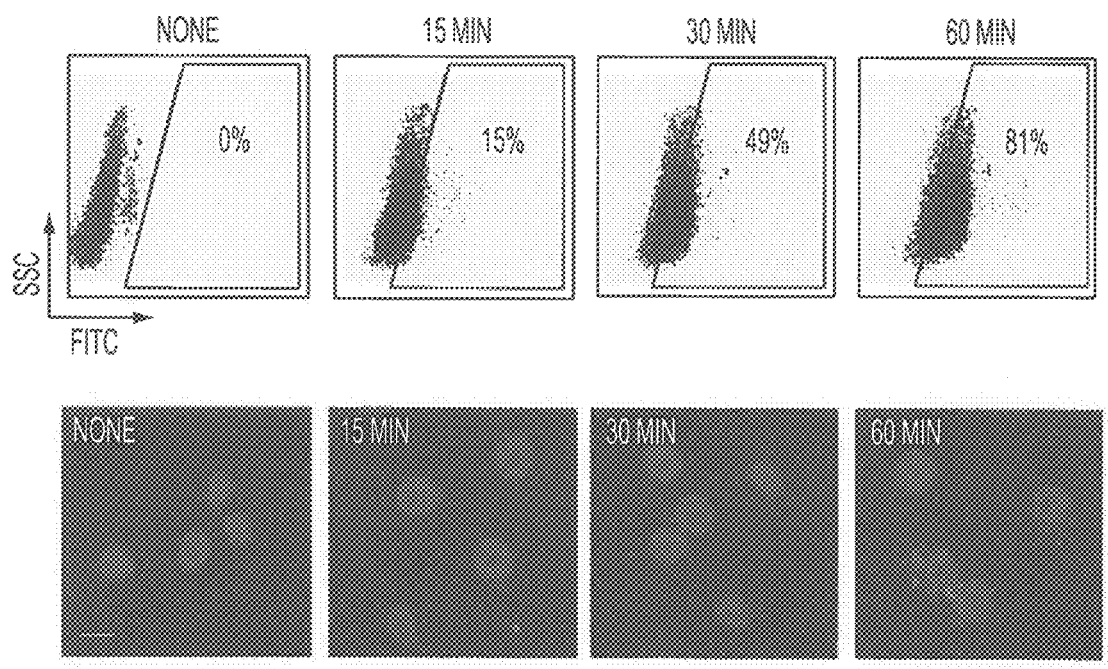
Figure 2D:
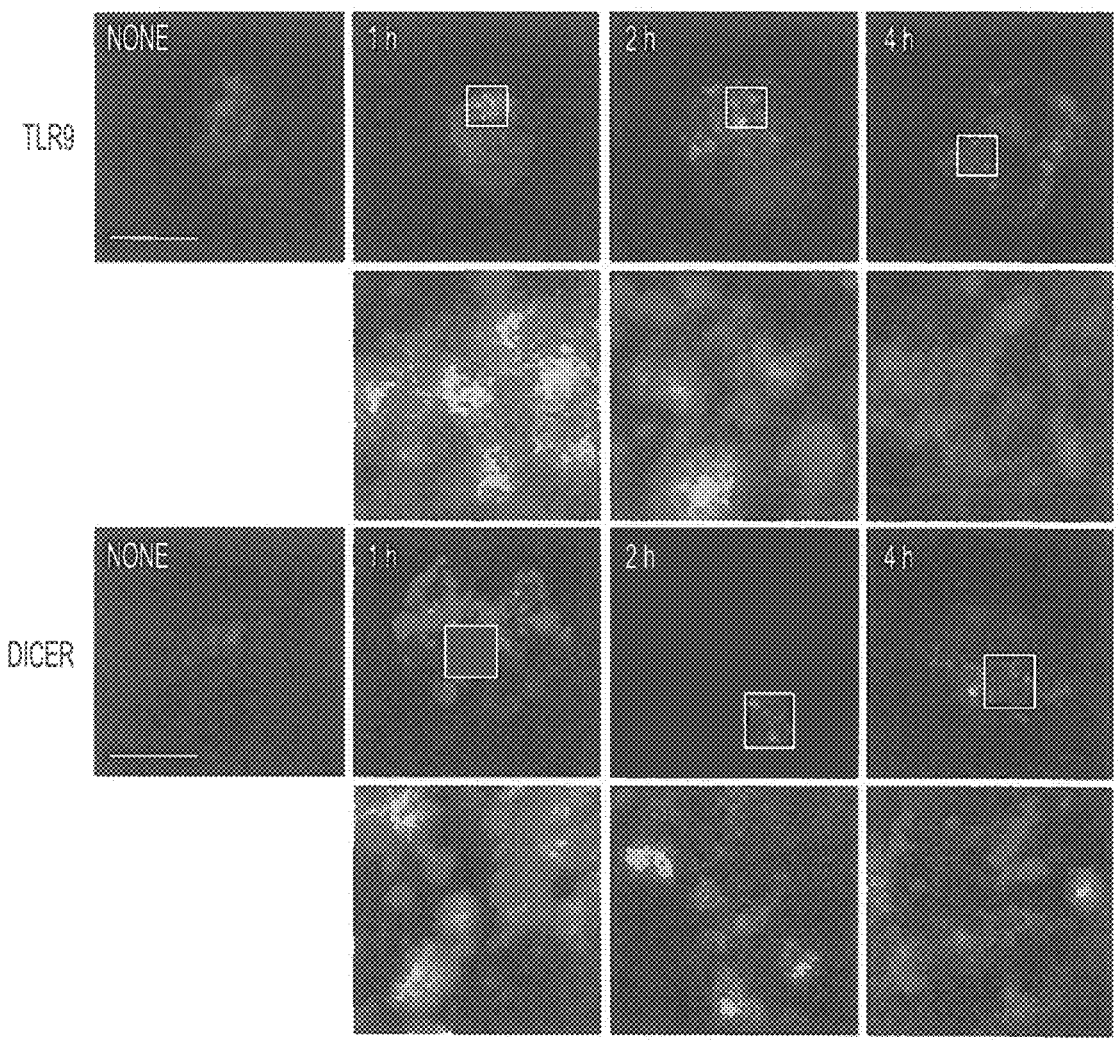
Figures 2E, 2F:
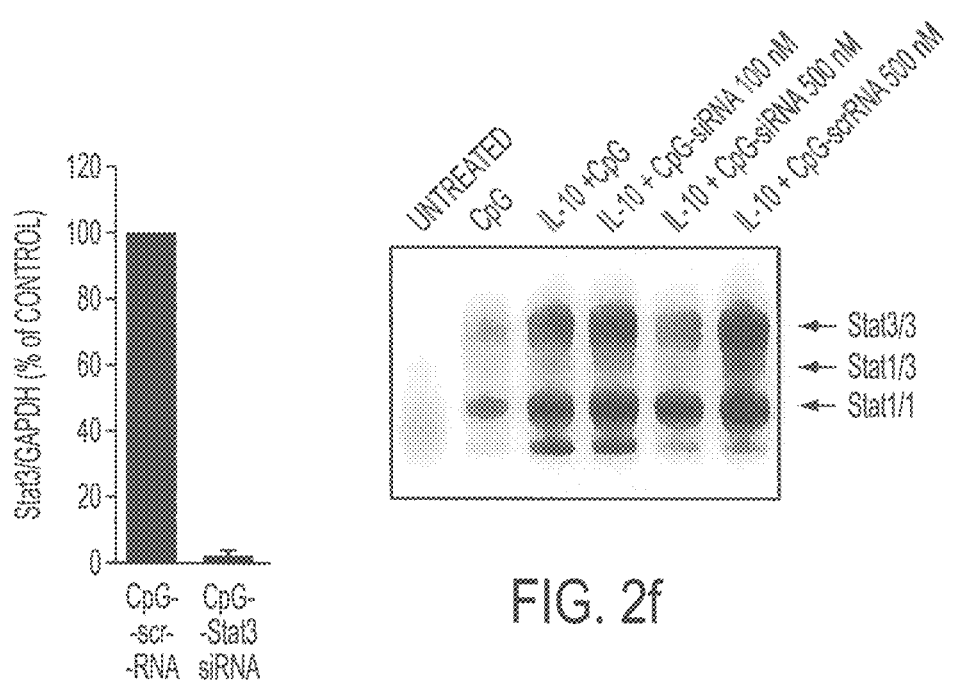
Figure 3A:
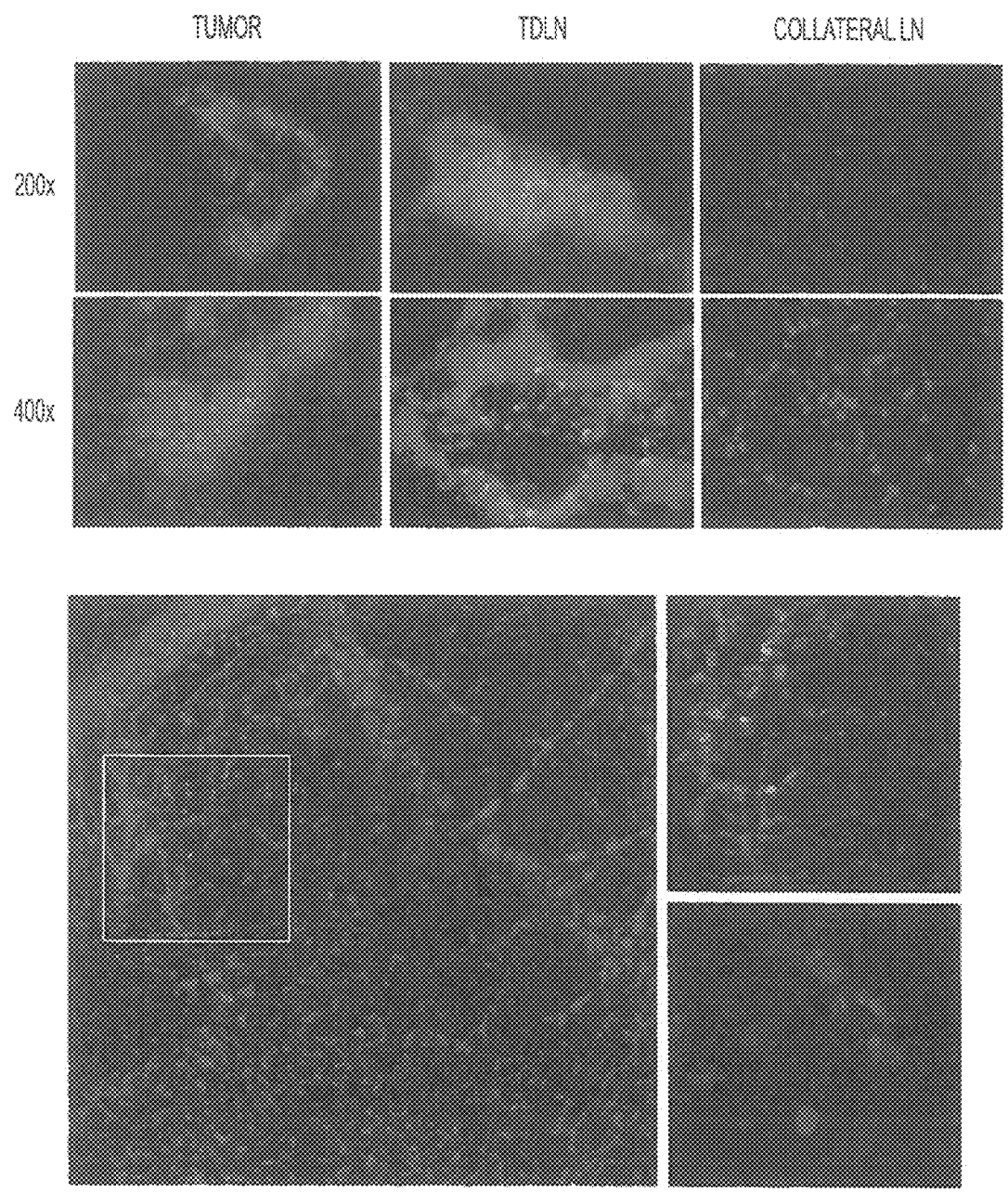
Figure 3F:
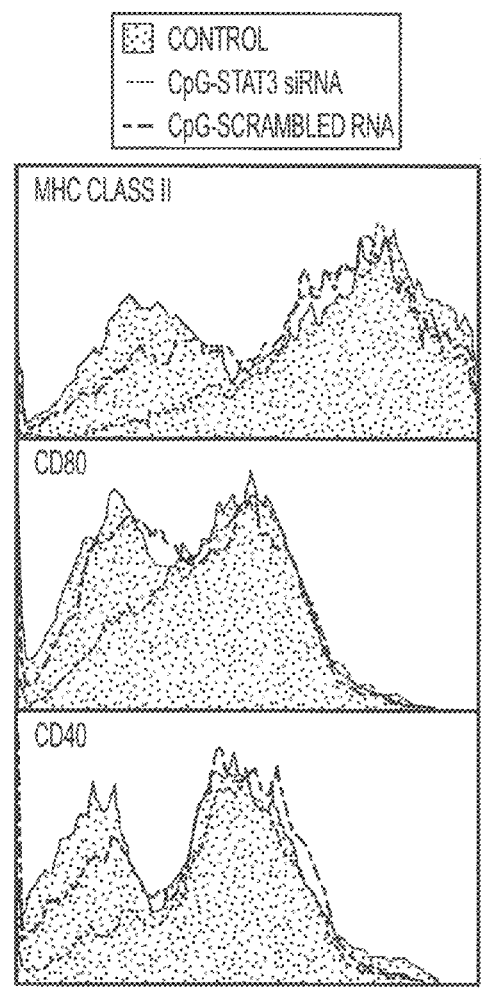
Figure 3G:
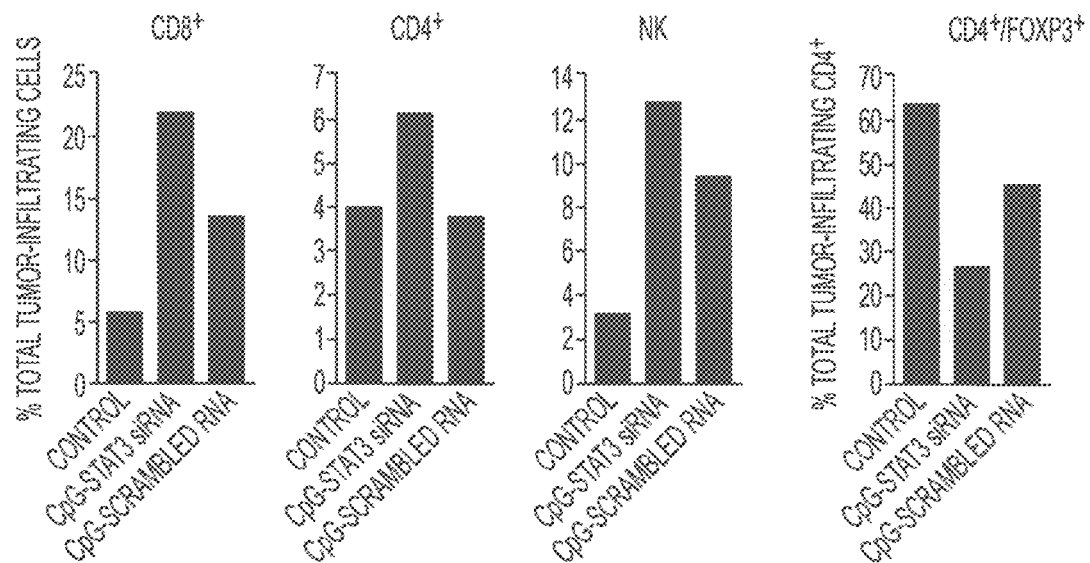
Figure 3H:
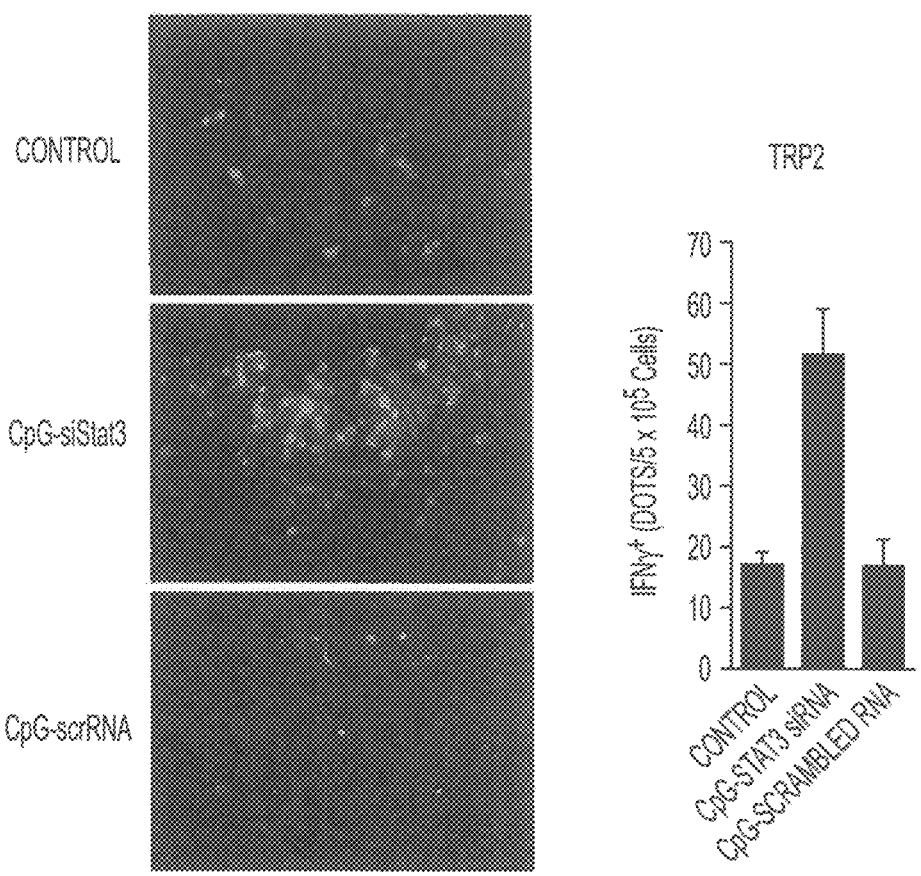

As an example of the TLR ligand-siRNA chimeric construct, siRNA against Stat3 (SEQ ID NO:3 for sense strand; SEQ ID NO:2 for antisense strand) is linked to toll-like receptor 9 ligand, CpG oligonucleotide (ODN) (SEQ ID NO:1) (FIG. 2a, top). Optimal sequences of both human and mouse Stat3 siRNA have been selected (FIG. 7), followed by linkage to CpG single stranded ODN (FIG. 2a, top), and other toll-like receptor ligands (FIG. 8). The construct can be processed by Dicer (FIG. 2a, lower), and is associated with Dicer in living cells (FIG. 2d), and causes gene silencing (FIGS. 2e, 2f). The chimeric constructs, when delivered in vivo in tumor bearing mice, are efficiently uptaken and internalized by targeted cells, such as macrophages and dendritic cells (FIG. 3a). These immune cells are able to traffic from tumor to tumor training lymph nodes, where they can interact with T cells (FIG. 3a). In vivo gene silencing is also detected in dendritic cells and macrophages in tumor draining lymph nodes (FIG. 3b). The immune modulation induced by the toll-like receptor 9 ligand-Stat3 siRNA leads to potent antitumor effects on well established B16 melanoma (FIGS. 3c-3e). Both local intratumoral injection and systemic intravenous injection routes are tested, demonstrating the usefulness of the ODN-siRNAs as therapeutic agents (FIGS. 3c-3e). CpG alone, Stat3siRNA alone, or CpG-linked to a scrambled siRNA are not able to induce significant antitumor effects, testifying the superior efficacies of linking two active moieties: TLR9 ligand and Stat3 siRNA (FIG. 3c-e). Tumor bearing mice treated with the CpG-Stat3siRNA constructs display activation of dendritic cells (FIG. 3f), increased CD8+T cells, NK cells and reduced number of T regulatory cells in the tumor and/or tumor draining lymph nodes (FIG. 3g). Treating tumor-bearing mice with CpG-Stat3siRNA also increases tumor infiltrating tumor antigen-specific CD8+T cells (FIG. 3h).

Similarly, TLR ligand-siRNA chimeric constructs can also be taken up by human monocytes, leading to gene silencing (FIG. 4).

Figure 5A:
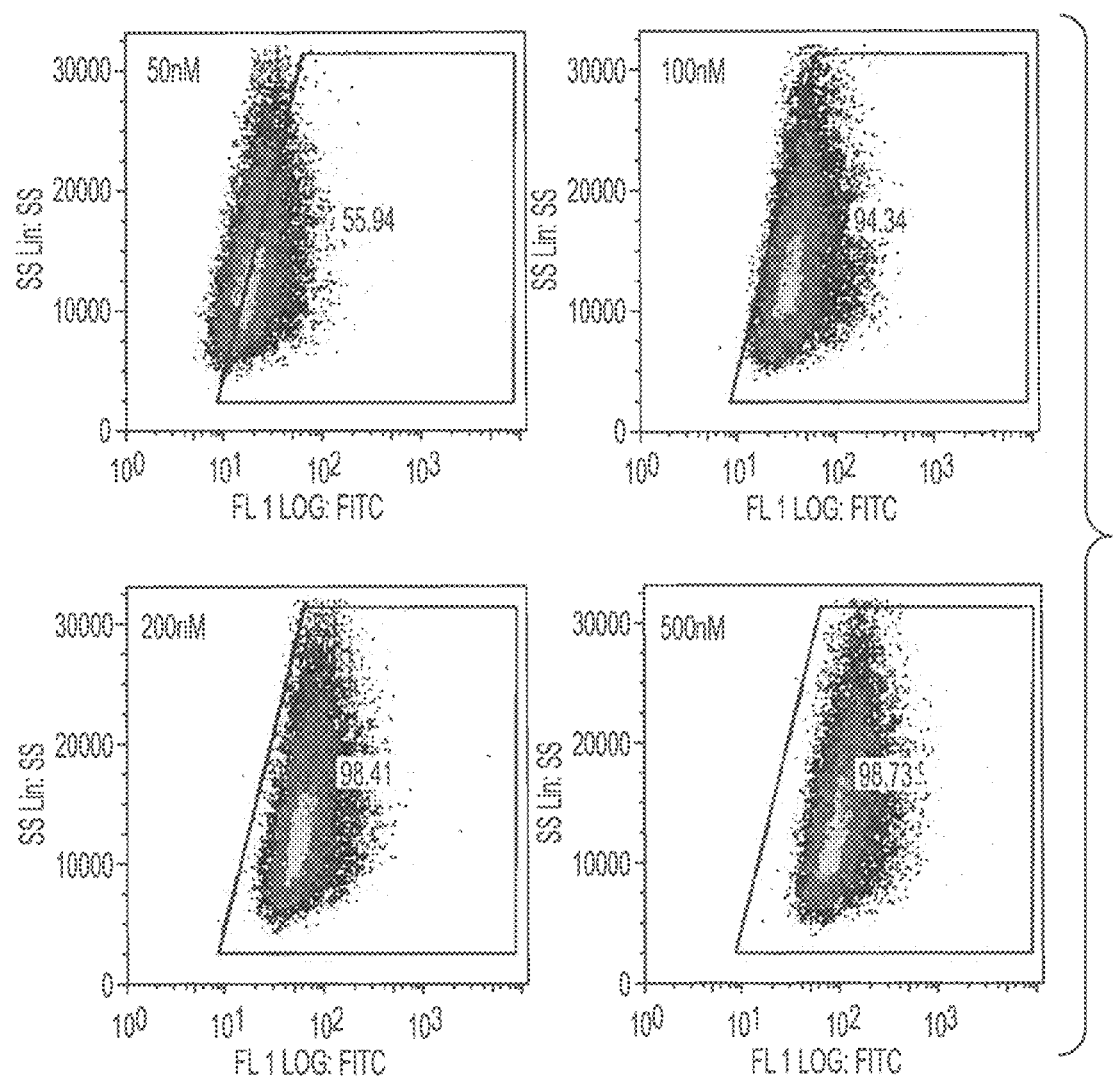

We have further shown that the CpG-Stat3siRNA is easily uptaken by both murine and human B malignant cells, including both lymphoma and multiple myeloma cells (FIG. 5), many of which also express TLR (Bourke et al., 2003; Reid et al., 2005; Jahrsdorfer et al., 2005). We show that uptake and internalization of the CpG-Stat3siRNA leads to gene silencing of Stat3 (FIG. 5d), which is accompanied by increased cell cycle arrest of the myeloma cells relative to those treated with CpG-scrambled siRNA in cell culture (FIG. 5e). Furthermore, in vivo treatment with the CpG-Stat3siRNA construct leads to significant growth inhibition of well-established murine myeloma tumors (FIG. 6a). Tumor growth inhibition due to CpG-Stat3siRNA in vivo treatment is associated with upregulation of co-stimulatory molecules on tumor-infiltrating dendritic cells (FIG. 6b, c).

The DNA (or RNA)-RNA constructs are synthesized chemically without involvement of enzymes. The success of CpG-Stat3siRNA chimeric molecule for inducing immune responses and antitumor effects, through blocking Stat3 in immune cells and/or in tumor cells, demonstrates a novel general approach: using TLR ligand oligonucleotides, which include CpG, polyI:C (TLR3 ligand), polyG (TLR8 ligand), to deliver short RNA, which include both siRNA and activating RNA, to desired cells in vitro and in vivo, to stimulate innate immunity, to negate undesired effects and/or elicit desired effects through siRNA and/or activating RNA.

As a result, creating chimeric molecule consisting of TLR ligand and siRNA and/or activating RNA, has great versatility and can be easily adapted for various gene targets. It also has flexibility: similar design can be adapted for different cell types capable of ODN/ORN uptake and internalization.

Using a linker, modification of such approach to include multiple active moieties, such as multiple siRNA, with TLR ligand as a single agent for treating cancer and infectious disease is feasible. This approach can also be modified to enable small molecule drug delivery.

More specifically, the present invention relates to specific chimeric molecules that are useful for the treatment of diseases. Thus, in one aspect, the present invention provides a standard conjugate for use in preclinical and phase I studies. In accordance with this aspect, the chimeric molecule comprises the components:

A. Human STAT3 SS siRNA (sense strand; underlined are deoxyribonucleotides):

(SEQ ID NO: 4)
GGA AGC UGC AGA AAG AUA CGA CUG A;

B. Human CpG(D19)-STAT3 AS siRNA (antisense strand; asterisks indicate phosphorothioated sites, X indicates single C3 carbon chain linker/propanediol linker):

(SEQ ID NO: 16 XXXXX SEQ ID NO: 5)
G*GT GCA TCG ATG CAG G*G*G* G*G XXXXX UCA GUC GUA

UCU UUC UGC AGC UUC CGU.

In a second aspect, the present invention provides a chimeric molecule that is prepared to include modification sites for the sense strand sequence to produce a conjugate with increased serum stability. In accordance with this aspect, the modified sense strand comprises:

A. Human STAT3 SS siRNA (sense strand; underlined are deoxyribonucleotides; bold are chemically modified for increased nuclease resistance, e.g. 2'F-, 2'OMe-, LNA, nucleotides or other modifications described herein):

(SEQ ID NO: 17)
GGA AGC UGC AGA AAG AUA CGA CUG A.

In one embodiment, this sense strand is combined with the human CpG(D19)-STAT3 AS siRNA described above.

In a third aspect, the present invention provides an alternative three-component conjugate with complementary "sticky ends" instead of fixed propanediol linker between CpG and siRNA moieties (to simplify synthesis). In accordance with this aspect, the chimeric molecule comprises the components:

A. Human STAT3 SS siRNA-overhang (sense strand; X indicates single C3 carbon chain linker/propanediol linker; bold are chemically modified 2'F- or 2'OMe-nucleotides or other modifications as described herein):

(SEQ ID NO: 18 XXXXX SEQ ID NO: 19)
GGA AGC UGC AGA AAG AUA CGA CUG A XXXXX ACG UGG CCG ACU UCC U;

B. Human CpG(D19)-overhang (asterisks indicate phosphorothioated sites; X indicates single C3 carbon chain linker/propanediol linker; bold are chemically modified 2'F- or 2'OMe-nucleotides or other modifications as described herein):

(SEQ ID NO: 5 XXXXX SEQ ID NO: 20)
G*GT GCA TCG ATG CAG G*G*G* G*G XXXXX AGG AAG UCG GCC ACG U;

C. Human STAT3 AS siRNA (antisense strand):

(SEQ ID NO: 5)
UCA GUC GUA UCU UUC UGC AGC UUC CGU.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley—VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods for Examples 1-10

Cells Lines: Mouse B16 melanoma cells were purchased from American Type Culture Collection. Human peripheral blood mononuclear cells (PBMC) from healthy donors were collected by apheresis and mononuclear cells were isolated over a Ficoll gradient.

Oligonucleotide Design and Synthesis: The phosphothioated oligodeoxynucleotide (ODN) and antisense strands (AS) of siRNAs were linked using 6 units of C3 spacer (Glen Research, San Diego, Calif.). The resulting constructs were hybridized with complementary sense strands (SS) of siRNAs to create chimeric ODN-siRNA constructs used in the study (deoxynucleotides are shown underlined). Sequences of single stranded constructs are listed below. See also FIG. 8.

```
Mouse Stat3 siRNA (SS)
                                                 (SEQ ID NO: 3)
5' CAGGGUGUCAGAUCACAUGGGCUAA 3'

CpG1668-mouse Stat3 siRNA (AS)
                                 (SEQ ID NO: 1-linker-SEQ ID NO: 2)
5' TCCATGACGTTCCTGATGCT-linker-UUAGCCCAUGUGAUCUGACACCCUGAA 3'

GpC-mouse Stat3 siRNA (AS)
                                 (SEQ ID NO: 6-linker-SEQ ID NO: 2)
5' TCCATGAGCTTCCTGATGCT-linker-UUAGCCCAUGUGAUCUGACACCCUGAA 3'

Human STAT3 siRNA (SS)
                                                 (SEQ ID NO: 4)
5' GGAAGCUGCAGAAAGAUACGACUGA 3'

CpG(D19)-human STAT3 siRNA (AS)
                                 (SEQ ID NO: 1-linker-SEQ ID NO: 5)
5' GGTGCATCGATGCAGGGGGG-linker-UCAGUCGUAUCUUUCUGCAGCUUCCGU 3'

Scrambled RNA (SS)
                                                 (SEQ ID NO: 8
5' UCCAAGUAGAUUCGACGGCGAAGTG 3'

CpG1668-scrambled RNA (AS)
                                 (SEQ ID NO: 1-linker-SEQ ID NO: 9)
5' TCCATGACGTTCCTGATGCT-linker-CACUUCGCCGUCGAAUCUACUUGGAUU 3'
```

The correct formation of siRNA duplex was confirmed by in vitro Dicer cleavage assays. 0.5 µg of each ODN-siRNA construct was subjected to processing by 1 U of Dicer (Ambion) in 37° C. for 1.5 hr, resolved with 15% polyacrylamide/7.5M urea gel and results of the dicing reaction were visualized with SYBR Gold staining (Invitrogen).

Quantitative Real-Time PCR: Total RNA was extracted from cultured or primary cells using RNeasy kit (Qiagen). After cDNA synthesis using iScript cDNA Synthesis kit (Bio-Rad), samples were analyzed using pairs of primers specific for Stat3, GAPDH mRNAs or 18S rRNA (SuperArray Bioscience Corporation). Sequence-specific amplification was detected by fluorescent signal of SYBR Green (Bio-Rad) by using Chromo4 Real-time PCR Detector (Bio-Rad).

Electromobility Shift Assay (EMSA) and Western Blot: EMSA and western blot analyses to detect Stat3 DNA-binding and protein expression were performed as described previously (Wang et al., 2004).

In Vivo Experiments: Mouse care and experimental procedures were performed under pathogen-free conditions in accordance with established institutional guidance and approved protocols from Research Animal Care Committees of the City of Hope. We obtained Mx1-Cre mice from the Jackson Laboratory and Stat3$^{flox/flox}$ mice from S. Akira and K. Takeda. Generation of mice with Stat3$^{-/-}$ hematopoietic cells by inducible Mx1-Cre recombinase system has been reported (Kortylewski et al., 2005b; Lee et al., 2002). For s.c. tumor challenge, we injected 1×10$^5$ B16 tumor cells into 7-8 weeks old transgenic mice 4 d after poly(I:C)-treatment to induce Stat3 ablation. After tumors reached average size of ca. 1 cm, mice were injected peritumorally with 0.78 nmole of phosphothioated CpG ODN (CpG1668; SEQ ID NO:1) or control GpG ODN (GpC; SEQ ID NO:6)) in some experiments, and tumor growth was monitored three times a week. For the analysis of cellular and molecular mechanisms of CpG ODN effect, mice were sacrificed at 1, 2 or 3 d post-CpG treatment, and spleens, lymph nodes as well as tumor specimens were harvested. For cell depletion experiments in vivo, mice were pretreated with anti-CD8 and anti-CD4 antibodies (clone 2.43 and GK1.5, respectively) or anti-asialo-GM1 serum (Wako) before tumor inoculation and then were injected at weekly intervals during the course of the experiment. In experiments on CpG-mediated siRNA delivery, mice were challenged with B16 tumors 6 days or 2 days before starting intratumoral or intravenous injections of 0.78 nmole ODN-RNA fusion constructs, respectively. Treatment continued every second day for 2-3 weeks, mice were sacrificed and immune effects of treatments were analyzed.

Flow cytometry and ELISA: We prepared single cell suspensions of spleen, lymph node or tumor tissues by mechanic dispersion followed by collagenase D/DNase I treatment as described before (Kortylewski et al., 2005b). For extracellular staining of mouse immune markers 1×10$^6$ of freshly prepared cells suspended in PBS/2% FCS/0.1% w/v sodium azide was preincubated with FcγIII/IIR-specific antibody to block non-specific binding and stained with different combinations of fluorochrome-coupled antibodies to CD11c, I-A$^b$ (MHCII), CD40, CD80, CD86, CD11b, Gr1, CD49b, CD3, CD8, CD4, CD69, B220 or Foxp3 (BD Biosciences). Human monocytes were stained with fluorochrome-coupled antibodies to CD14 and CD3 (eBioscience). Fluorescence data were collected on FACScalibur (Beckton Dickinson) and analyzed using FlowJo software (Tree Star). For IL-12/p70 measurement by ELISA (eBioscience), splenic DCs isolated as described above were cultured with or without CpG ODN for 18 h before collecting supernatants.

ELISPOT Assay: 5×10$^5$ cells isolated form tumor-draining lymph nodes of CpG- or ODN-siRNAs-treated mice, were seeded into each well of 96-well filtration plate in the presence or absence of 10 μg/ml of p15E or TRP2 peptide. After 24 h of incubation at 37° C., peptide-specific IFNγ-positive spots were detected according to manufacturer's procedure (Cell Sciences), scanned and quantified using Immunospot Analyzer from Cellular Technology Ltd.

Immunofluorescent and Intravital Two Photon Microscopy: For immunofluorescent stanings, we fixed the flash-frozen tumor specimens in formaldehyde, permeabilized with methanol and stained with antibodies to CD8, CD11b (BD Biosciences), TLR9 (eBiosciences), Dicer (Santa Cruz) and detected with Alexa488- or Alexa555-coupled secondary antibodies from Invitrogen. After staining the nuclei with Hoechst 33342 (Invitrogen), slides were mounted and analyzed by fluorescent microscopy. For intravital two-photon imaging, B16 tumor-bearing mice received single intratumoral injection of 0.78 nmole FITC-labeled CpG-Stat3 siRNA, followed by retroorbital injection of dextran-rhodamine (Invitrogen) and Hoechst 33342 prior to imaging 2 h later. Mice were anesthesized and intravital two-photon microscopy was carried out using equipment and software from Ultima Multiphoton Microscopy Systems.

Statistical Analysis: To compare tumor size or surface marker expression between multiple test groups in animal experiments, we performed a one-way ANOVA followed by Newman-Keuls test. Unpaired t test was used to calculate two-tailed p value to estimate statistical significance of differences between two treatment groups. Statistically significant p values were labeled as follows: *; p<0.001; , p<0.01 and *, p<0.05. Data were analyzed using Prism software (GraphPad).

Example 2

Figure 1B:
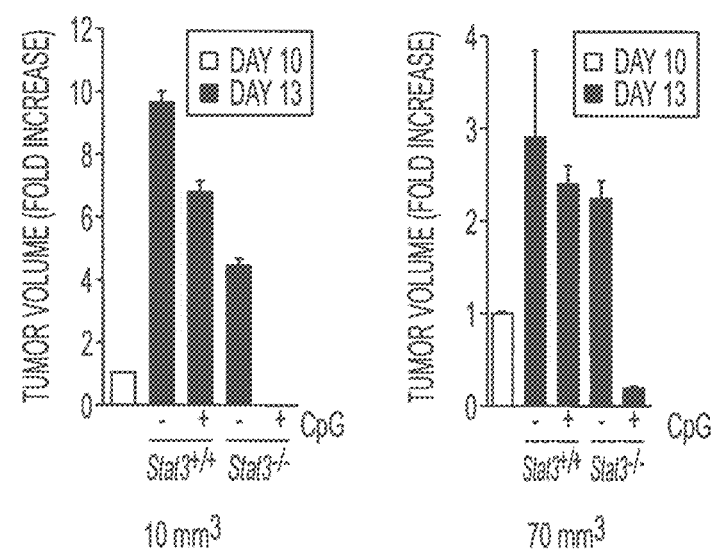
Figure 1C:
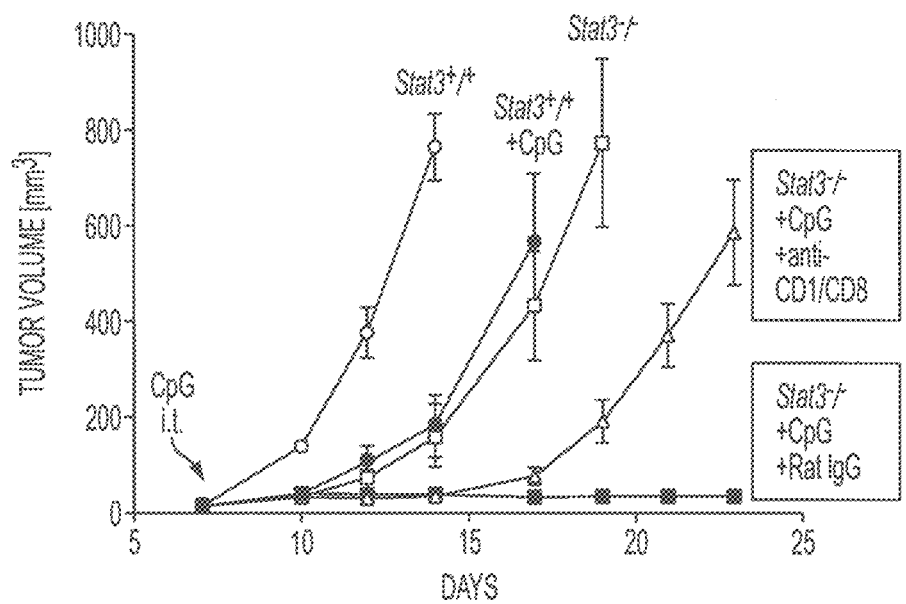
Figure 1D:
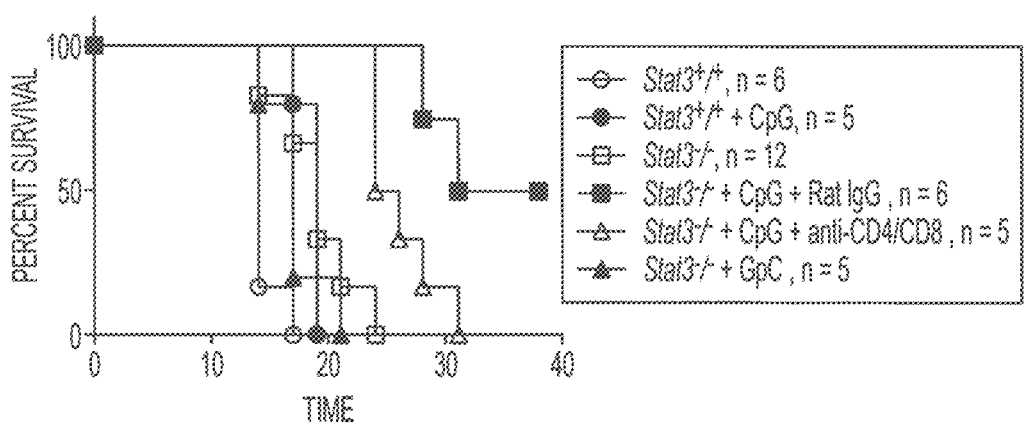

Stat3 Ablation in Hematopoietic Cells Drastically Improves TLR9 Triggering-Induced Antitumor Effects To provide proof-of-principle evidence that targeting Stat3 can markedly enhance CpG-ODN-based immunotherapy, we induced Stat3 allele truncation in the hematopoietic cells of adult mice using the Mx1-Cre-loxP system as described previously (Kuhn et al., 1995). We employed PCR-based genotyping assay to confirm the truncation of loxP-flanked Stat3 alleles induced by repeated injections of poly(I:C) in hematopoietic cells in Mx1-Cre expressing mice. To avoid any interference from poly(I:C) treatment, subcutaneous B16(F10) tumor challenge was performed five days after last poly(I:C) administration. Established B16 tumors (day 10 post 10$^6$ tumor cell challenge, >10 mm diameter) were treated with a single peritumoral injection of 5 μg CpG1668-oligonucleotide. Although CpG-ODN treatment did not show significant antitumor activity in control mice (Stat3+/+) with heavy tumor load (FIG. 1b—right panel), the same treatment resulted in eradication of large B16 tumors (some of them reaching 1.5 cm in diameter) in mice lacking intact alleles within 3 days after injection (FIGS. 1a and 1b). Similarly, whereas CpG-ODN injection showed only weak inhibition of tumor growth in mice with smaller initial B16 tumors (4-6 mm diameter) (FIG. 1b—left panel), peritumoral treatment of with CpG-ODN in mice with truncated Stat3 alleles in the hematopoietic cells resulted in regression of rapidly growing B16 tumors (FIG. 1c) and prevented their reoccurrence over the period of at least 3 weeks (FIG. 1d). In contrast, treatment with control GpC oligonucleotide lacking CpG motif recognized by TLR9 did not significantly inhibit tumor progression.

To assess whether the dramatically increased antitumor effects contributed by Stat3 inhibition in the hematopoietic cells was mediated by T cells, we used CD8 and CD4 antibodies to deplete T cells. The enhanced antitumor immunity due to Stat3 allele truncation in hematopoietic cells was abrogated in mice depleted of CD4 and CD8 T cells (FIGS. 1c and 1d). However, lack of both lymphocyte populations did not prevent the initial robust tumor regression, strongly suggesting the involvement of innate immunity in eliminating the established tumors. Indeed, NK cell depletion experiments indicated a partial role of NK cells for the observed antitumor effect.

Example 3

Ablating Stat3 in Hematopoietic Cells Further Activates DCs Primed by CpG

Figure 1E:
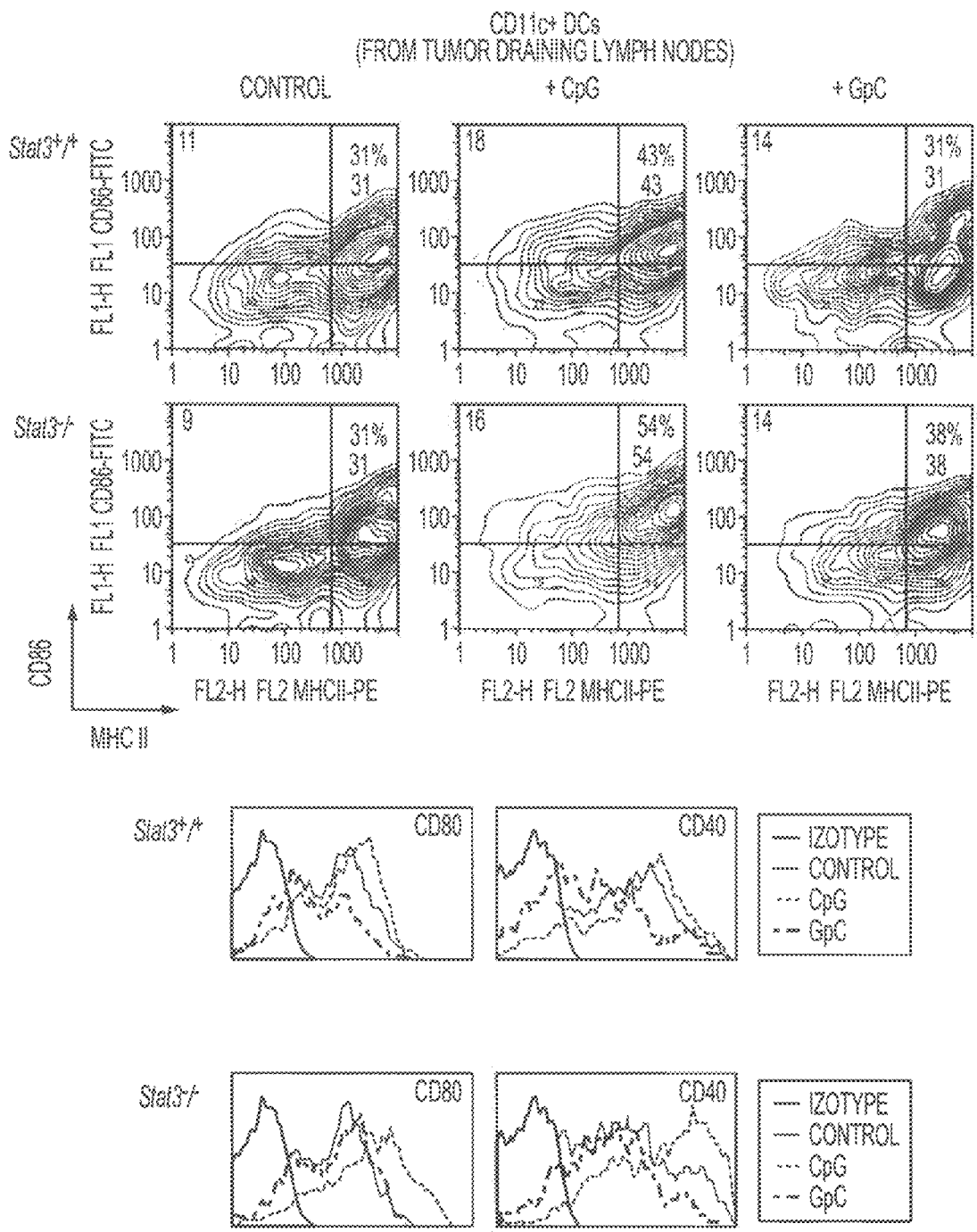
Figure 1I:
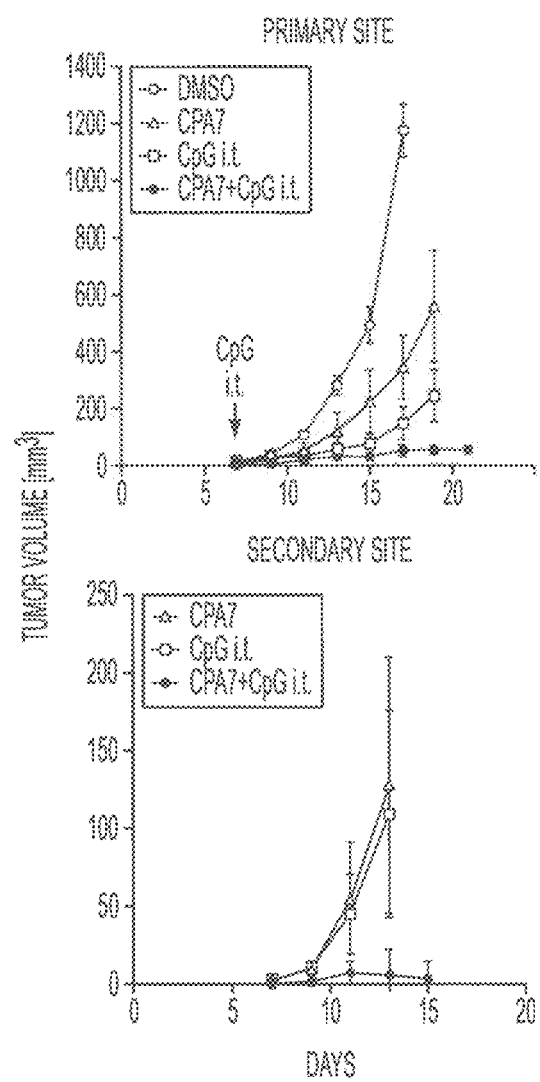

We next assessed if Stat3 inhibition affects CpG-induced DC activation in tumor-bearing mice. Flow cytometric analysis of CD11c+DCs isolated from tumor-draining lymph nodes of mice with truncated Stat3 in hematopoietic cells showed enhanced DCs activation as measured by increased expression of major histocompatibility complex (MHC) class II, CD86, CD80 and CD40 molecules two days after peritumoral injection of CpG-ODN but not control GpC-ODN (FIG. 1e—upper and lower panels). We further assessed the expression of several immunostimulatory cytokines like IL-12 (p35 and p40 subunits), RANTES and IL-6 in DCs freshly isolated from tumor microenvironment following local treatment with CpG-ODN. As shown in FIG. 1f, CpG-ODN induced high levels of all tested proinflammatory mediators in Stat3-deficient but not in wild-type DCs within 18 hrs after treatment.

To evaluate the effect of Stat3 blocking on CpG-induced effector lymphocyte activity, we analyzed CD8 T cells within tumor-draining lymph nodes of Stat3-positive and Stat3-negative mice after CpG-ODN treatment. CD8+ lymphocytes in tumor-draining lymph nodes of Stat3-ablated mice showed very high levels of CD69 immediate early activation marker, shortly after peritumoral injection of CpG-ODN (FIG. 1g, left panel). Moreover, 10 days after CpG-treatment Stat3-deficient mice had increased ability to mount tumor antigen-specific responses. The number of IFN-γ-secreting T cells was strongly enhanced by CpG-treatment in the tumor-draining lymph nodes of Stat3−/− mice, as indicated by ELISPOT assay following ex vivo exposure to B16 tumor-specific p15E antigen (FIG. 1g, right panel).

Example 4

Targeting Stat3 in Myeloid Cells (Dendritic Cells and Macrophages) by a Chimeric ssDNA-siRNA Construct Results shown in FIG. 1 provide proof-of-principle evidence that blocking Stat3 signaling in the hematopoietic cells removes a key negative regulator of DC activation, thereby drastically improving TLR-9-mediated DC activation and antitumor immunity. However, previous studies indicated that prolonged, and effective blockade of Stat3 signaling through gene ablation/truncation in the whole hematopoietic compartment can lead to autoimmunity (Alonzi et al., 2004; Kobayashi et al., 2003; Welte et al., 2003). In order to minimize the side-effects of Stat3 blocking and yet achieve Stat3 inhibition-mediated enhancement of antitumor immunity induced by TLR triggering, it would be ideal to specifically and efficiently block Stat3 in antigen presenting cells while simultaneously activating TLR9 pathway. To achieve this goal, we tested the possibility to generate an ssDNA-dsRNA chimeric construct that contains both CpG and Stat3 siRNA. The 20 by long single-stranded CpG1668 ODN sequence was fused to a double-stranded 25/27-mer Stat3siRNA (FIG. 2a). The selection of optimized 25/27 Stat3siRNA (both human and mouse) is based on the report that Dicer-processed siRNA has enhanced silencing effects of target genes (Kim et al., 2005) (FIG. 7). In vitro cleavage assay confirmed that the chimeric CpG-Stat3 siRNA construct is processed by recombinant Dicer enzyme, just like the 25/27-mer Stat3 siRNA without CpG (FIG. 2a, lower panel).

To test cell specific uptake of chimeric ssDNA-dsRNA oligonucleotide constructs, freshly isolated splenocytes from wild-type C57BL/6 mice were incubated overnight with the fluorescein-labeled CpG-Stat3-siRNA construct. Such incubation in the absence of any transfection agents resulted in dose-dependent uptake of the DNA-RNA chimeric construct by splenic DCs and macrophages but not granulocytes or T cells (FIG. 2b). Under the same conditions the uptake of fluorescently-labeled naked Stat3-siRNA was insignificant. Further analysis of CpG-Stat3-siRNA uptake by confocal microscopy indicated rapid internalization of the chimeric construct with kinetics similar to the one previously reported for the CpG-ODN alone (Latz et al., 2004) (FIG. 2c). In stable DC cell line (DC2.4), the CpG-Stat3-siRNA can be detectable as early as 15 min, with high uptake after 1 h of incubation. At this time point CpG-Stat3-siRNA construct was found to colocalize with TLR9 within perinuclear endocytic vesicles (FIG. 2d—two top rows). Previous studies indicated that binding of the Dicer nuclease to the siRNA oligonucleotide is required for its further processing into shorter 21-mer fragments before interacting with RISC complex, which is responsible for the final gene silencing effect (Chendrimada et al., 2005; Haase et al., 2005). We observed transient colocalization of the CpG-Stat3-siRNA with Dicer within 2 h after adding the oligonucleotide chimeric construct to cultured DCs. The association between the CpG-Stat3-siRNA and Dicer became weaker by 4 h and undetectable after 24 h (FIG. 2d—bottom two panels). These data suggest a sequential mode of CpG-Stat3-siRNA construct action, which starts with the uptake into cytoplasmic endocytic vesicles, followed by binding to TLR9 and subsequent interaction with Dicer. Quantitative real-time PCR analysis of the Stat3 mRNA expression in cultured primary DCs and in DC2.4 cells indicated a dose-dependent downregulation of the Stat3 expression after 24 h incubation with CpG-Stat3-siRNA, while the CpG-scrambled-RNA control had negligible effect (FIG. 2e). These results indicate that chimeric CpG-siRNA molecules are efficiently internalized by TLR9-positive cells, undergo processing by Dicer and induce gene silencing. Of note, we observed that CpG treatment itself can upregulate Stat3 activity and also gene expression (FIG. 2f).

Example 5

In Vivo Characterization of the Chimeric CpG-siRNA

To evaluate the feasibility of using chimeric CpG-siRNA in vivo, we estimated first the uptake of the CpG-Stat3 siRNA in tumor-bearing mice. C57BL/6 mice with B16 tumors (6-10 mm in diameter) were injected peritumorally with FITC-labeled CpG-Stat3 siRNA at 0.78 nmol (20 µg)/injection. We detected large numbers of FITC-positive CD11b+ myeloid cells in tumor-draining nodes but not in collateral lymph nodes, 6 h after injection (FIG. 3a—top panel). More sensitive detection by two-photon microscopy confirmed the presence of FITC-positive cells in tumor-draining lymph node as early as 1 h after injecting the labeled construct (FIG. 3a—lower panel). Further studies have shown that repeated peritumoral and to lesser extent intravenous injections of 0.78 nmole CpG-Stat3-siRNA, but not CpG-scrambled-RNA, silence Stat3 expression in DCs and/or macrophages within tumor-draining lymph nodes (FIGS. 3b and 3d).

Example 6

Antitumor Effects of the CpG-Stat3 siRNA Chimeric Construct

Both macrophages and DCs in the tumor microenvironment are known to promote immune tolerance. We next assessed if the CpG-Stat3-siRNA chimeric constructs would negate immunosuppressive effects imposed by the tumor-microenvironment and at the same time allow effective antitumor immunity induced by TLR9 triggering. Local treatment with CpG-Stat3-siRNA oligonucleotides inhibited growth of subcutaneously growing B16 melanoma. In contrast, treatment with CpG-ODN alone or the CpG-scrambled-RNA construct had relatively weak antitumor effects (FIG. 3c). The ability of CpG-Stat3-siRNA to inhibit metastatic tumor growth was further demonstrated in the model of established B16 lung metastasis. We assessed the effect of 2-week systemic treatment with CpG-Stat3-siRNA, using relatively small amount of the oligonucleotide (1 mg/kg). Systemic injection of 0.78 nmole CpG-Stat3-siRNA led to significant reduction in the number of lung metastasis with lesser effect of CpG-scrambled-RNA and CpG-ODN alone (FIG. 3e), which is accompanied by upregulation of MHC class II, CD80 and CD40 molecules on tumor infiltrating DCs (FIG. 3f).

The ratio of effector to negative regulatory T cells within tumor microenvironment is considered an important indicator of the effect of adaptive immune responses against tumor. We investigated the numbers of tumor infiltrating T cell populations in subcutaneously growing B16 tumors treated locally for 2 weeks with CpG-Stat3-siRNA, CpG-scrambled-RNA control or left untreated (FIG. 3g). We observed an increase in the infiltration of CD8+T cells in the tumor stroma from 5 to more than 20%, and an increase in tumor antigen, TRP2, positive CD8+T cells in the tumor (FIG. 3h). In addition to CD8+T cells, the numbers of tumor-infiltrating NK cells and neutrophils are higher in mice treated with CpG-Stat3-siRNA (FIG. 3g). Concomitant with an increase in tumor infiltrating CD8+, NK and neutrophils that are important killing tumor cells, the percentage of CD4+/FoxP3+T reg cells within all CD4+T cells dropped from approximately 60 to 25% after repeated peritumoral injections of CpG-Stat3-siRNA (FIG. 3g).

Example 7

Silencing STAT3 in Human Monocyte-Derived DCs to Prevent Immunosuppression

Figure 4A:
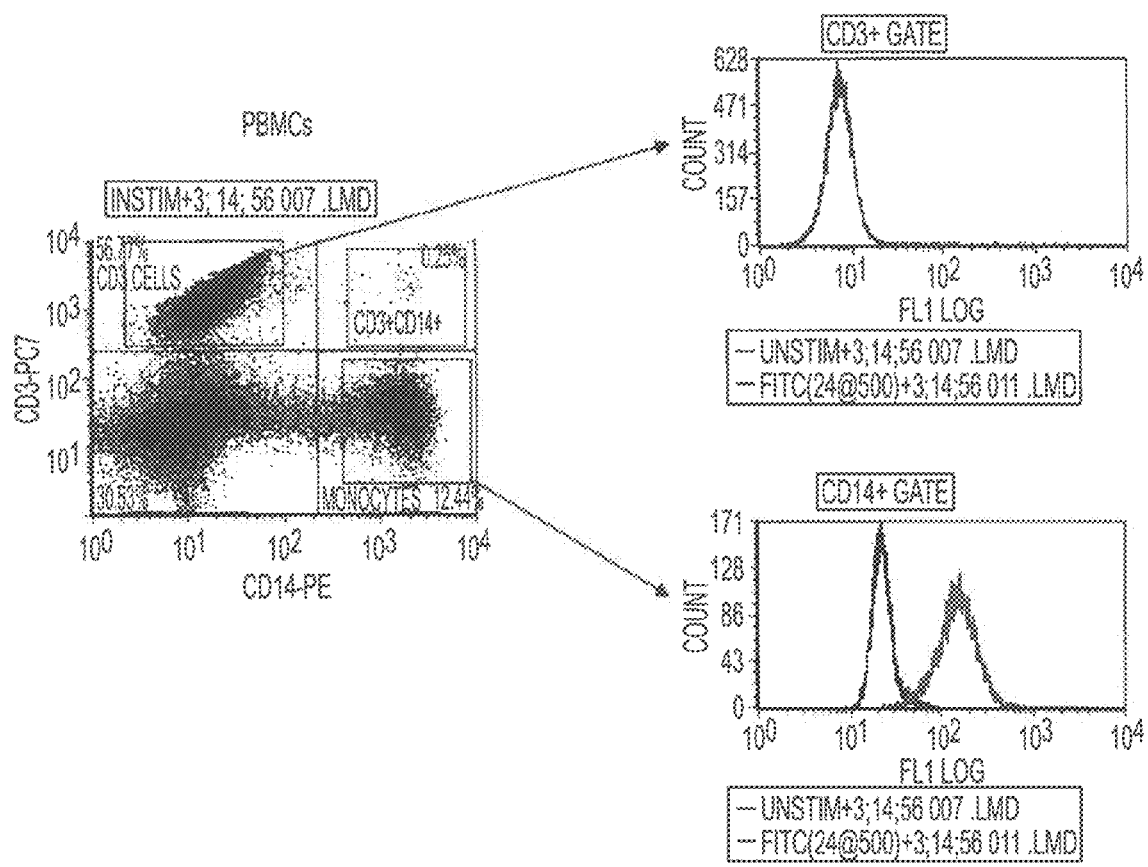
FIGS. 4a-4d show that CpG(D19)-STAT3 siRNA allows for targeting STAT3 in human monocytes and monocyte-derived DCs. CpG(D19)-STAT3siRNA is internalized specifically by $CD14^+$ monocytes from human PBMCs (FIG. 4a) and cultured monocyte-derived DCs in dose—(FIG. 4b) and time-dependent manner (FIG. 4c) as measured by flow cytometry.
Figure 4B:
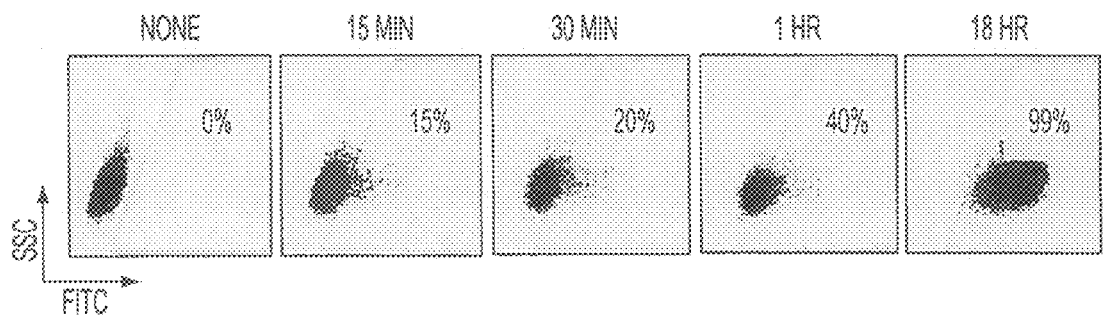
Figure 4C:
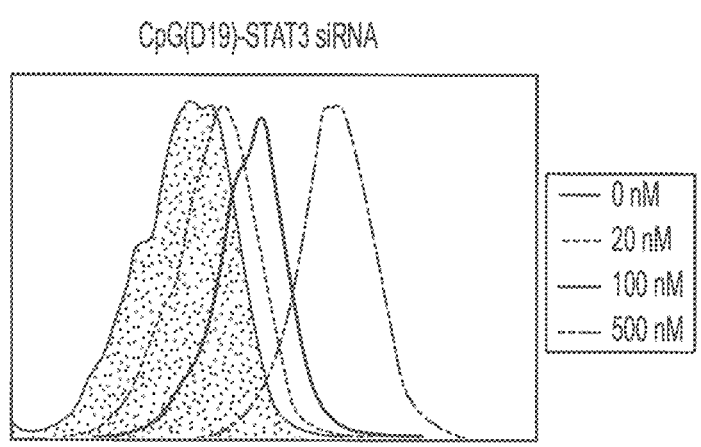
Figure 4D:
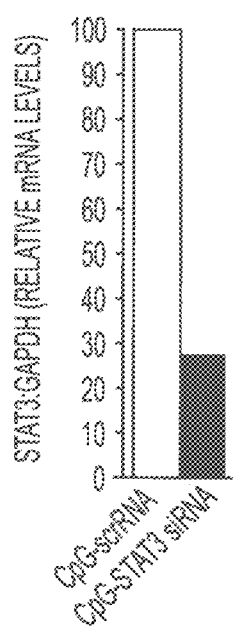

The expression of TLR9 as well as the ability to take up CpG-based oligonucleotides is reportedly restricted to relatively rare population of plasmacytoid DCs in humans. However, moderate levels of TLR9 expression have recently been found also in more common monocyte-derived DCs (MoDCs) isolated or expanded from peripheral blood mononuclear cells (PBMCs). We created an analogue chimeric oligonucleotide by fusion of CpG(D19) sequence optimized for activation of human TLR9-positive cells with the STAT3-specific siRNA selected for the highest silencing effect in human cells. Next, we incubated fluorescein-labeled CpG (D19)-STAT3-siRNA with human PBMCs to determine the level and specificity of oligonucleotide uptake (FIG. 4a). Flow cytometric analysis revealed the internalization of fusion oligonucleotide by CD14+ monocytes but not by other PBMCs including CD3+ lymphocytes. Similarly to the mouse DCs, CpG(D19)-STAT3-siRNA uptake is detectable after short incubation time. Chimeric oligonucleotide internalization is dose dependent within the range of 20 to 500 nM, with maximal near 100% uptake at the highest concentration after 24 h (FIGS. 4b and 4c). Under these conditions, CpG (D19)-STAT3-siRNA reduced STAT3 expression by almost 75% comparing to CpG-scrambled-RNA control as measured by real-time PCR analysis (FIG. 4d).

Example 8

Targeting Stat3 in Malignant B Cells by CpG-Stat3 siRNA

Not only Stat3 is activated in immune cells in the tumor microenvironment, promoting tumor immunosuppression, Stat3 is constitutively activated in tumor cells of diverse origin (Yu and Jove, 2004; Yu et al., 2007). Stat3 activity intrinsic to the tumor cells upregulate a large range of genes critical for tumor growth, survival, angiogenesis/metastasis and immunosuppression. It is therefore highly desirable for any Stat3 inhibitor to be able to block Stat3 in the tumor cells. Because many malignant cells of B cell origin, including multiple myeloma and B cell lymphoma express TLR9 (Bourke et al., 2003, Reid et al., 2005; Jahrsdorfer et al., 2005), we test the possibility that CpG-Stat3siRNA can be internalized by these tumor cells, leading to gene silencing and tumor growth inhibition. To directly test these possibilities, we incubated several human B lymphoma cell lines with CpG-Stat3siRNA for uptake and internalization. The data shown in FIGS. 5a-5e shows that CpG-STAT3 siRNA allows for siRNA delivery into various types of human B lymphoma cells, in a dose-dependent manner. We then assess the uptake and the effects of CpG-Stat3siRNA in a mouse myeloma model. The results shown in FIGS. 6a-6c indicate that mouse myeloma cells, MCP11, internalize FITC-labeled CpG-Stat3 siRNA in a dose-dependent manner, as shown by flow cytometry after 24 h incubation. Furthermore, CpG-Stat3siRNA can lead to Stat3 silencing in MPC 11 cells treated with 100 nM CpG-Stat3 siRNA for 24 h, as measured by real-time PCR. Importantly, MCP11 cells treated with CpG-Stat3siRNA leads to accumulation in the $G_2M$ phase of cell cycle as measured by flow cytometry after propidium iodide staining.

We next determined whether targeting Stat3 by CpG-Stat3 siRNA causes antitumor effects against MPC11 multiple myeloma. Mice bearing large MCP11 tumors (10-13 mm in diameter) are injected intratumorally with 0.78 nmole of CpG-siStat3 or CpG-scrRNA and two more times every second day. MPC11 tumor is very aggressive, but in vivo treatment with CpG-Stat3siRNA results in significant tumor growth inhibition (FIG. 6a). Analysis of the tumor samples indicate that CpG-Stat3siRNA increases tumor cell apoptosis. An increased percentage of DCs in tumor-draining lymph-nodes after CpG-Stat3 siRNA treatment is also detected (FIG. 6b). Moreover, there is an increase in CD40 and CD86 expression in tumor-draining lymph node DCs (FIG. 6c), suggesting that CpG-Stat3siRNA treatment can lead to activation of DCs in the tumor milieu. These results demonstrate that CpG-siRNA approach can target tumor cells of B cell origin, leading to antitumor effects through direct effects on the tumor cells.

Example 8

Use of Activating RNAs to Promote Specific Gene Expression In Vitro and In Vivo

Recently, it has been shown in several cases that double stranded small RNA against targets at the promoter regions positively regulate gene transcription. For example, transcriptional activation of E-cadherin and VEGF is achieved by 21-nt double stranded RNAs targeting the promoter region of these genes in human prostate cancer cells. We employed the same method to activate mouse Edg1 gene, which is important for angiogenesis and immunosuppression. The small double strand RNA (21mer) sequences we identified for the mouse Edg1 gene are:

```
Sense:
                                    (SEQ ID NO: 10)
5' UGUCCUCUGUCCUCUAAGAUU-TT 3'

Antisense:
                                    (SEQ ID NO: 11)
5' AAUCUUAGAGGACAGAGGACA-TT 3'
```

Figure 9:
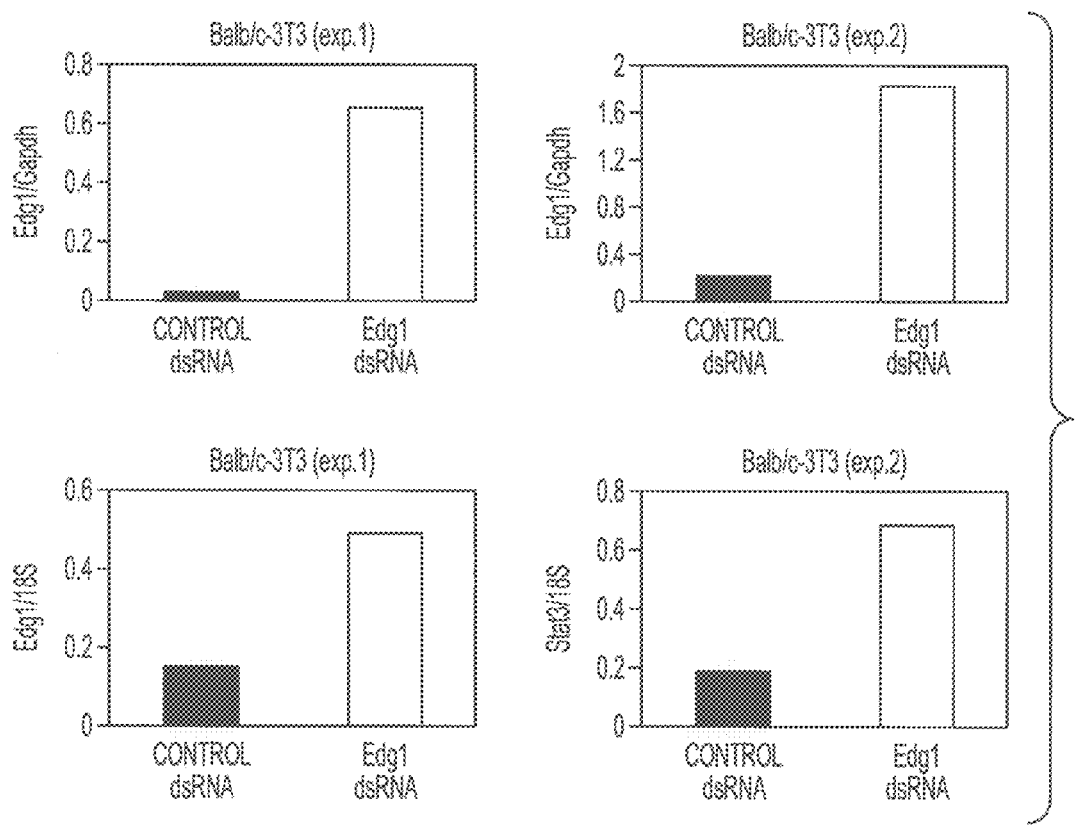
FIG. 9 shows that a double stranded RNA with sequences complimentary to sequences of the mouse Edg1 gene promoter region are able to activate Edg1 expression in vitro. The Edg1 double stranded RNA when transfected into cells (both 3T3 fibroblasts and B 16 tumor cells) induces strong transcription of the Edg1 gene, as determined by real-time PCR.

This Edg1 double stranded RNA when transfected into cells (both 3T3 fibroblasts and B16 melanoma tumor cells) can induce strong transcription of the Edg1 gene (FIG. 9).

Figure 10:
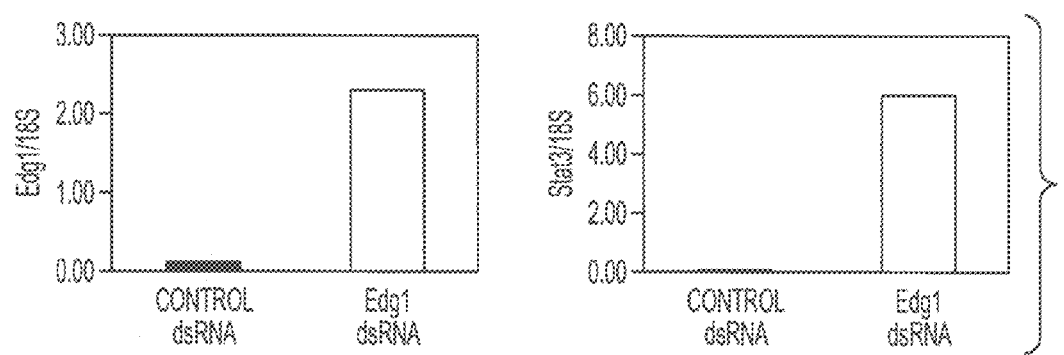
FIG. 10 shows that the activating RNA is active for at least three weeks in living animals. Tumor cells transfected with the activating RNA for Edg1 promoter, when implanted into mice, maintain high levels of Edg1 expression for at least 3 weeks, as determined by analyzing tumors for Edg1 expression using real-time PCR at three weeks after tumor implantation.

Example 9 dsRNA Against Promoter Region of Edg1 Activates Edg1 Transcription 3T3 Fibroblasts or B16 Melanoma Cells Tumor cells transfected with the dsRNA against promoter region of Edg1, when implanted into mice, maintain high levels of Edg1 expression for at least 3 weeks, as determined by analyzing tumors using real-time PCR (FIG. 10) at three weeks after tumor implantation.

The upregulation of Edg1 due to its own activating RNA leads to angiogenesis, immunosuppression and drastic tumor growth.

Examples 8 and 9 illustrate the use of short (21mer) double stranded RNAs to activate specific genes in vivo to modulate biological responses, thereby leading to therapeutic outcomes. Linking CpG and other toll-like receptor ligand(s) with short siRNA illustrated in the previous Examples is useful for targeted delivery of activating RNA, which like siRNA, is short double stranded RNA.

Example 10

Chemical Synthesis of Constructs Containing a Targeting Molecule and siRNA

The constructs that were synthesized consisted of the RNA sequence, CpG sequence, and of the linker connecting those two. Synthesis was conducted on Perseptive Biosystems DNA Synthesizer Expedite 8909 in the trityl-off mode.

Reagents: 5'-dimethoxytrityl-N-benzoyl-adenosine, 2'-O-TBDMS-3'-[(2-cyanoethyl)-(N,N-diisopropyl)]-phosphoramidite; 5'-dimethoxytrityl-N-acetyl-cytidine, 2'-O-TBDMS-3'-[(2-cyanoethyl)-(N,N-diisopropyl)]-phosphoramidite; 5'-dimethoxytrityl-N-isobutyryl-guanosine, 2'-O-TBDMS-3'-[(2-cyanoethyl)-(N,N-diisopropyl)]-phosphoramidite; 5'-dimethoxytrityl-uridine, 2'-O-TBDMS-3'-[(2-cyanoethyl)-(N,N-diisopropyl)]-phosphoramidite; 5'-dimethoxytrityl-N-benzoyl-deoxyadenosine-3'-[(2-cyanoethyl)-(N,N-diisopropyl)]-phosphoramidite; 5'-dimethoxytrityl-N-acetyl-deoxycytidine-3'-[(2-cyanoethyl)-(N,N-diisopropyl)]-phosphoramidite; 5'-dimethoxytrityl-N-p-tert-butylphenoxyacetyl-deoxyguanosine-3'-[(2-cyanoethyl)-(N,N-diisopropyl)]-phosphoramidite; and, 5'-dimethoxytrityl-thymidine-3'-[(2-cyanoethyl)-(N,N-diisopropyl)]-phosphoramidite were purchased from Azco Biotech, Inc. (San Diego, Calif., USA).

C3 spacer (3-(4,4'-dimethoxytrityloxy)propyl-1-[(2-cyanoethyl)-(N,N-diisopropyl)]-phosphoramidite) was synthesized in-house (Seela and Kaiser, 1987) or purchased from Glen Research (Sterling, Va. USA). Ethylthiotetrazole (AIC) was used as activator. Fluorescein phosphoramadite (1-dimethoxytrityloxy-2-(N-thiourea-(di-O-pivaloyl-fluorescein)-4-amino-butyl)-propyl-3-O-(2-cyanoethyl)-(N,N-diisopropyl)-phosphoramidite) (Glen Research, Sterling, Va., USA) was used for the introduction of fluorescein into the oligomers.

Beaucage Reagent from American International Chemical, Inc. (AIC; Framingham, Mass., USA) was used for thioation of the phosphates of the CpG part of the construct.

The oligonucleotides were deprotected after synthesis with 10 M methylamine in ethanol-water 1:1, 55° C. for 30 min.

The deprotected constructs were purified by Polystyrene Reverse Phase Ion-Pair Chromatography (PRP-IPC). (Swiderski et al., 1994). Combined fractions containing the pure product were concentrated under the reduced pressure to the volume of 1 ml. Ammonium acetate (100 mg) and 2.5 ml of ethanol were added. Samples were kept at −20° C. for 4 hrs and then centrifuged for 5 min. Supernatant did not have absorption at 260 nm. Precipitate was resuspended in 1 ml of sterile water and re-precipitated as above. Preparative purification of oligonucleotides was carried out on a Gilson Gradient HPLC System equipped in UniPoint System Software. Purification was performed by Ion-Paired HPLC on polystyrene resign PRP-1 (Hamilton) (4.6×250 mm); buffer A, 10 mM tetrabutylammonium acetate, water-acetonitrile 9:1 (pH 7.2); buffer B, 10 mM tetrabutylammonium acetate, water-acetonitrile, 1:9, gradient 0-65% of B in 30 min.

Analytical polyacrylamide gel electrophoresis (PAGE) was carried out using 20% crosslinked gels (1 mm thick, 19:1 acrylamide: bis-acrylamide). Buffer: 100 mM Tris-borate, 1 mM EDTA, 7 M urea, pH 8.3 (25). Gels were visualized by UV (254 nm) shadowing followed by methylene blue staining. Large scale synthesis of very pure, long (40-mers and longer) and complex oligonucleotides has its limitations. Due to the presence of RNA component yields are lower and purification process more difficult.

TLR Agonist-Stat3 siRNA Conjugates: Cell-Specific Gene Silencing and Enhanced Antitumor Immune Responses Efficient delivery of siRNA to specific cell populations in vivo is important to its successful therapeutic application. Described in Examples 11-15 is a novel siRNA-based approach—synthetically linking siRNA to an oligonucleotide TLR9 agonist—that targets and silences genes in TLR9$^+$ myeloid cells and B cells, both of which are key components of the tumor microenvironment is described. Because Stat3 in tumor-associated immune cells suppresses antitumor immune responses and hinders TLR9 signaling, we tested CpG-Stat3siRNA conjugates for anti-tumor effects. When injected locally at the tumor site or systemically through an intravenous route, the CpG-Stat3siRNA conjugates access tumor-associated dendritic cells, macrophages and B cells, inhibit Stat3 expression, leading to activation of diverse tumor-associated immune cells, and ultimately potent anti-tumor immune responses. The findings described herein demonstrate the potential of TLR agonist-siRNA conjugates for targeted gene silencing coupled with TLR stimulation and immune activation in the tumor microenvironment.

Because Stat3 also restrains TLR-mediated Th1 immune responses (Kortylewski et al., 2005b; Kortylewski et al., 2009b; Yu et al., 2007), we reasoned that simultaneously silencing Stat3 by siRNA and triggering TLRs by their agonists could effectively shift the tumor microenvironment from pro-carcinogenic to anti-carcinogenic, potentially resulting in systemic tumor-specific immunity that could further inhibit tumor metastases. A recent study using polymer-mediated in vivo transfection of 5'-triphophate-Bcl2 siRNA has demonstrated the power of simultaneously inducing antitumor immunity and silencing an oncogenic gene (Poeck et al., 2008).

In this study, we explored a strategy of linking siRNAs to synthetic oligonucleotide agonists for endosomal TLRs, which include TLR3, TLR7, TLR8 and TLR9 (Iwasaki and Medzhitov, 2004; Kanzler et al., 2007; Barchet et al., 2008), for targeted delivery of siRNA into the endosomal compartment of immune cells, such as myeloid cells and B cells, together with TLR-dependent activation of antitumor immune responses. The endosomal location of the oligonucleotide-binding TLRs, such as TLR9, might be advantageous in facilitating ultimate uptake of the siRNA component to the cytosol of targeted cells for more efficient gene silencing in cells selectively expressing the cognate TLR. In order to model this concept, we chose TLR9-specific oligodeoxynucleotides containing an unmethylated CpG-motif (CpG ODN), because they are already in clinical testing (Krieg, 2008). Additionally, CpG ODN are efficiently internalized by various antigen-presenting cells, such as dendritic cells, macrophages and B cells, and their binding to TLR9 can initiate a cascade of innate and adaptive immune responses (Klimman et al., 2004; Barchet et al., 2008; Krieg, 2008). These immune cells are also critical components of the tumor microenvironment that actively promote oncogenesis (Kujawski et al., 2008; Yu et al., 2007; Kortylewski et al., 2008; Bollrath et al., 2009; Grivennikov et al., 2009). By linking the single-stranded CpG ODN with double-stranded siRNA, we have created a single synthetic molecule capable of delivering siRNA into myeloid and B cells, silencing an immune checkpoint and/or oncogenic gene, and activating TLR, leading to therapeutic antitumor immune responses.

Example 11

Materials and Methods for Examples 11-15

Cells: Murine B16 melanoma, CT26 colon carcinoma and A20 B cell lymphoma lines were purchased from American Type Culture Collection. Mouse dendritic DC2.4 cells were originally received from Dr. Kenneth Rock (University of Massachusetts Medical School, Mass.). Highly metastatic clone of K1735 melanoma (C4) was obtained from Drs. S. Huang and J. Fidler of M. D. Anderson Cancer Center (Houston, Tex.). The stably transduced A20-Luc cell line was kindly provided by Dr. Defu Zheng (City of Hope, Duarte, Calif.). The generation of transgenic C57BL/6.CEA mice and MC-38.CEA cell line was previously described (Tan and Coussens, 2007).

Oligonucleotide Design and Synthesis: The phosphothioated oligodeoxyribonucleotide (ODN) and antisense strands (AS) of siRNAs were linked using 6 units of C3 carbon chain linker, $(CH_2)_3$ (Glen Research, Sterling, Va.). The resulting constructs were hybridized with complementary sense strands (SS) of siRNAs to create chimeric ODN-siRNA constructs used in the study (deoxynucleotides are shown underlined). Sequences of single stranded constructs are listed below.

```
Mouse Stat3 siRNA (SS)
                                          (SEQ ID NO: 3)
5' CAGGGUGUCAGAUCACAUGGGCUAA 3'

CpG1668-mouse Stat3 siRNA (AS)
                       (SEQ ID NO: 1-linker-SEQ ID NO: 2)
5' TCCATGACGTTCCTGATGCT-linker-UUAGCCCAUGUGAUCUGACACCCUGAA 3'

GpC-mouse Stat3 siRNA (AS)
                       (SEQ ID NO: 6-linker-SEQ ID NO: 2)
5' TCCATGAGCTTCCTGATGCT-linker-UUAGCCCAUGUGAUCUGACACCCUGAA 3'

Scrambled RNA (SS)
                                          (SEQ ID NO: 8)
5' UCCAAGUAGAUUCGACGGCGAAGTG 3'

CpG1668-scrambled RNA (AS)
                       (SEQ ID NO: 1-linker-SEQ ID NO: 9)
5' TCCATGACGTTCCTGATGCT-linker-CACUUCGCCGUCGAAUCUACUUGGAUU 3'
```

The sequence of firefly luciferase-specific 25/27mer siRNA (Luc1 R 25D/27), used for the CpG1668-Luc siRNA conjugate molecule, was published before (Rose et al., 2005). The correct formation of siRNA duplex was confirmed by in vitro Dicer cleavage assays. 0.5 µg of each ODN-siRNA construct was subjected to processing by 1 U of Dicer (Ambion) in 37° C. for 1.5 hr, resolved with 15% polyacrylamide/7.5M urea gel and results of the dicing reaction were visualized with SYBR Gold staining (Invitrogen).

Quantitative Real-Time PCR: Total RNA was extracted from cultured or primary cells using RNeasy kit (Qiagen). After cDNA synthesis using iScript cDNA Synthesis kit (Bio-Rad), samples were analyzed using pairs of primers specific for Stat3, TNF, IL-6, IP-10, RANTES, p35/IL-12, p40/IL-12 and GAPDH mRNAs (SuperArray Bioscience Corporation). Sequence-specific amplification was detected by fluorescent signal of SYBR Green (Bio-Rad) by using Chromo4 Real-time PCR Detector (Bio-Rad).

Transient Transfections: B16 cells were transiently transfected with 15 nM CpG-linked or uncoupled Stat3 siRNA and scrambled RNA using Lipofectamine 2000 reagent (Invitrogen). 48 h later cells were lysed and used for western blot.

Electromobility Shift Assay (EMSA) and Western Blot: EMSA and western blot analyses to detect Stat3 DNA-binding and protein expression were performed as described previously (Wang et al., 2004). The protein levels of Stat3 detected by western blotting were later quantified by densitometry using AlphaEase FC software (Alpha Innotech).

Luciferase Reporter Gene Assay: A20-Luc cells incubated with CpG-RNAs for 48 h or primary cells isolated from tumor-draining lymph nodes of Luc[+] mice treated with CpG-Luc siRNA were lysed and luciferase activities were determined using the Luciferase Assay System (Promega) after normalization to the protein content of the sample.

In Vivo Experiments: Mouse care and experimental procedures were performed under pathogen-free conditions in accordance with established institutional guidance and approved protocols from Research Animal Care Committees of the City of Hope. For s.c. tumor challenge, we injected $1\times10^5$ B16, C4 or CT26 tumor cells into 7-8 weeks C57BL/6, C57BL/6.CEA, C3H or Balb/C mice, respectively. After tumors reached average size of ca. 5 mm, mice were injected peritumorally with 0.78 nmol of CpG1668 ODN alone, in combination with Stat3 siRNA or CpG/GpC ODN linked to various double stranded RNA (dsRNA) sequences described above. Tumor growth was monitored every other day. For the analysis of cellular and molecular mechanisms of CpG/GpC-dsRNAs effects, mice were killed after 2-3 weeks of treatment. For experiments on silencing of luciferase activity in vivo, $Luc^+$ mice (originally kindly provided by Dr. Christopher H. Contag, Stanford University School of Medicine, Calif.) were challenged with tumor and treated with 3 daily injections of CpG-Luc siRNA or CpG-scrambled RNA. Lymph nodes as well as tumor specimens were harvested. In experiments on B16 lung metastasis model, mice received intravenous injection of $0.5\times10^5$ B16 tumor cells and two days later, after tumors were established, started to be treated systemically with 0.78 nmol (ca. 1 mg/kg) of CpG1668 ODN alone or various CpG-dsRNAs. Intravenous injections were repeated every other day for two weeks. Lungs were harvested, fixed and the number of B16 colonies was manually counted. The level of Stat3 silencing was assessed by real-time PCR in DCs isolated from tumor-draining inguinal (for s.c. tumor model) or cervical (for metastasis model) lymph nodes. For immune cell depletion, mice were pretreated with anti-CD8 plus anti-CD4 antibodies (clone 2.43 and GK1.5, respectively, depleting 99% and 98% of CD8 and CD4 cells, respectively) or anti-asialo-GM1 antibodies (Wako, depleting min. 79% of NK cells) before tumor inoculation then injected weekly.

Flow Cytometry and ELISA: We prepared single cell suspensions of spleen, lymph node or tumor tissues by mechanic dispersion followed by collagenase D/DNase I treatment as described before (Kortylewski et al. 2005b). For extracellular staining of immune markers $1\times10^6$ of freshly prepared cells suspended in PBS/2% FCS/0.1% w/v sodium azide were pre-incubated with FcγIII/IIR-specific antibody to block non-specific binding and stained with different combinations of fluorochrome-coupled antibodies to CD11c, I-A$^b$ (MHCII), CD40, CD80, B220, CD11b, Gr1, CD3, CD8 or CD4 (BD Biosciences). Prior to intracellular staining with antibodies to TLR9 (eBioscience), Dicer (Santa Cruz) or FoxP3 (eBioscience), various immune cell subsets were fixed in paraformaldehyde and permeated in methanol. Fluorescence data were collected on FACScalibur (Beckton Dickinson) and analyzed using FlowJo software (Tree Star).

ELISPOT Assay: $5\times10^5$ cells isolated form tumor-draining lymph nodes of CpG- or CpG-siRNAs-treated mice, were seeded into each well of 96-well filtration plate in the presence or absence of 10 μg/ml of TRP2 peptide. After 24 h of incubation at 37° C., peptide-specific IFNγ-positive spots were detected according to manufacturer's procedure (Cell Sciences), scanned and quantified using Immunospot Analyzer from Cellular Technology Ltd.

Fluorescent, Confocal and Intravital Two Photon Microscopy: For immunofluorescent stanings, we fixed the flash-frozen tumor specimens in formaldehyde and permeabilized with methanol before antibody staining. For confocal microscopy, cultured cells were fixed with 2% paraformadehyde for 20 min, permeabilized in PBS/0.1% Triton X-100/1 mM $MgCl_2$, and 0.1 mM $CaCl_2$ for 5 min and quenched in 50 mM $NH_4Cl$ for 5 min before blocking in 1% BSA for 1 hr. Samples were stained with antibodies to CD11b (BD Biosciences), neutrophils (7/4, Cedarlane), active caspase-3 (Cell Signaling), TLR9 (eBiosciences), Dicer (Santa Cruz) and detected with Alexa488- or Alexa555-coupled secondary antibodies (Invitrogen). After staining the nuclei with DAPI (Vector) or Hoechst 33342, slides were mounted and analyzed by fluorescent or confocal microscopy. The confocal imaging was carried out using a 63x water immersion objective on cLSM510Meta confocal microscope (Zeiss). For intravital two-photon imaging, B16 tumor-bearing mice received single intratumoral injection of 0.78 nmol FITC-labeled CpG-Stat3 siRNA, followed by retroorbital injection of dextran-rhodamine (Invitrogen) and Hoechst 33342 prior to imaging 1 h later. Mice were anesthetized and intravital two-photon microscopy was carried out using equipment and software from Ultima Multiphoton Microscopy Systems.

Statistical Analysis: Unpaired t-test with equal or unequal variance (specifically for the analysis of cytokine expression in FIG. 26a) was used to calculate two-tailed P value to estimate statistical significance of differences between two treatment groups in the whole study. One-way ANOVA followed by Newman-Keuls test was applied for comparison of multiple treatment groups. Two-way ANOVA plus Bonferroni posttest were applied to assess statistical significance of differences in tumor growth kinetics between multiple treatment groups. Statistically significant P values were indicated in figures and/or legends and labeled as follows: *; $P<0.001$; , $P<0.01$ and *, $P<0.05$. Data were analyzed using GraphPad Prism vs. 4.0 software (GraphPad).

Example 12

Construction and In Vitro Characterization of the Cpg-Stat3 siRNA Conjugate Molecule Synthesis of the antisense strand of the siRNA (27mer) was followed by CpG1668 ODN synthesis (Klinman et al., 1999b; Krieg et al., 1995), producing a single stranded oligonucleotide connected through a carbon chain linker. The sense strand sequence of the Stat3 siRNA (25mer) is also shown (FIG. 11a). A 25/27mer form of siRNA was chosen over the conventional 21mer duplex to allow uncoupling of the siRNA from the CpG sequence by the Dicer enzyme once inside the cell. The asymmetric 25/27mer siRNA was optimized for specific processing by Dicer and was more potent in silencing of target genes (Kim et al., 2005; Rose et al., 2005). We first evaluated whether attaching siRNA to CpG ODN through the linker would interfere with TLR9 activation. Adding either CpG1688 alone or CpG-Stat3 siRNA conjugate to cultured DC2.4 dendritic cells resulted in a similar increase in expression of co-stimulatory CD40 and CD80 molecules, suggesting that CpG-Stat3 siRNA retains its capacity to activate TLR9 (FIG. 11b). In addition, we verified that the immunostimulatory properties of CpG-siRNA conjugates do not differ from the effect of CpG alone as measured by production of inflammatory cytokines in primary cells and NF-κB/AP1 activation in a stable macrophage cell line designed for such test (FIGS. 12a-12d). To assess whether the conjugation of siRNA with CpG moiety would still allow Dicer processing, we compared in vitro Dicer activity on CpG-Stat3 siRNA substrate versus 25/27mer Stat3 siRNA alone. The CpG-Stat3 siRNA and Stat3 siRNA were incubated with 1 U of recombinant Dicer for 1 h at 37° C. and then visualized on polyacrylamide gel through SYBRGold staining. Both the CpG-Stat3 siRNA and Stat3 siRNA were processed to 21mer siRNA by recombinant Dicer (FIG. 11c). Finally, to determine whether the CpG-Stat3 siRNA retains gene silencing function, the chimeric molecule was transfected into cells using Lipofectamine transfection reagent. Results from this experiment indicated that linking CpG ODN to siRNA did not interfere with Stat3 gene silencing (FIG. 11d). Both CpG-Stat3 siRNA and Stat3 siRNA alone reduced the total protein levels of Stat3 by 55% and 49%, respectively, as measured by densitometry.

Example 13

Figure 13A:
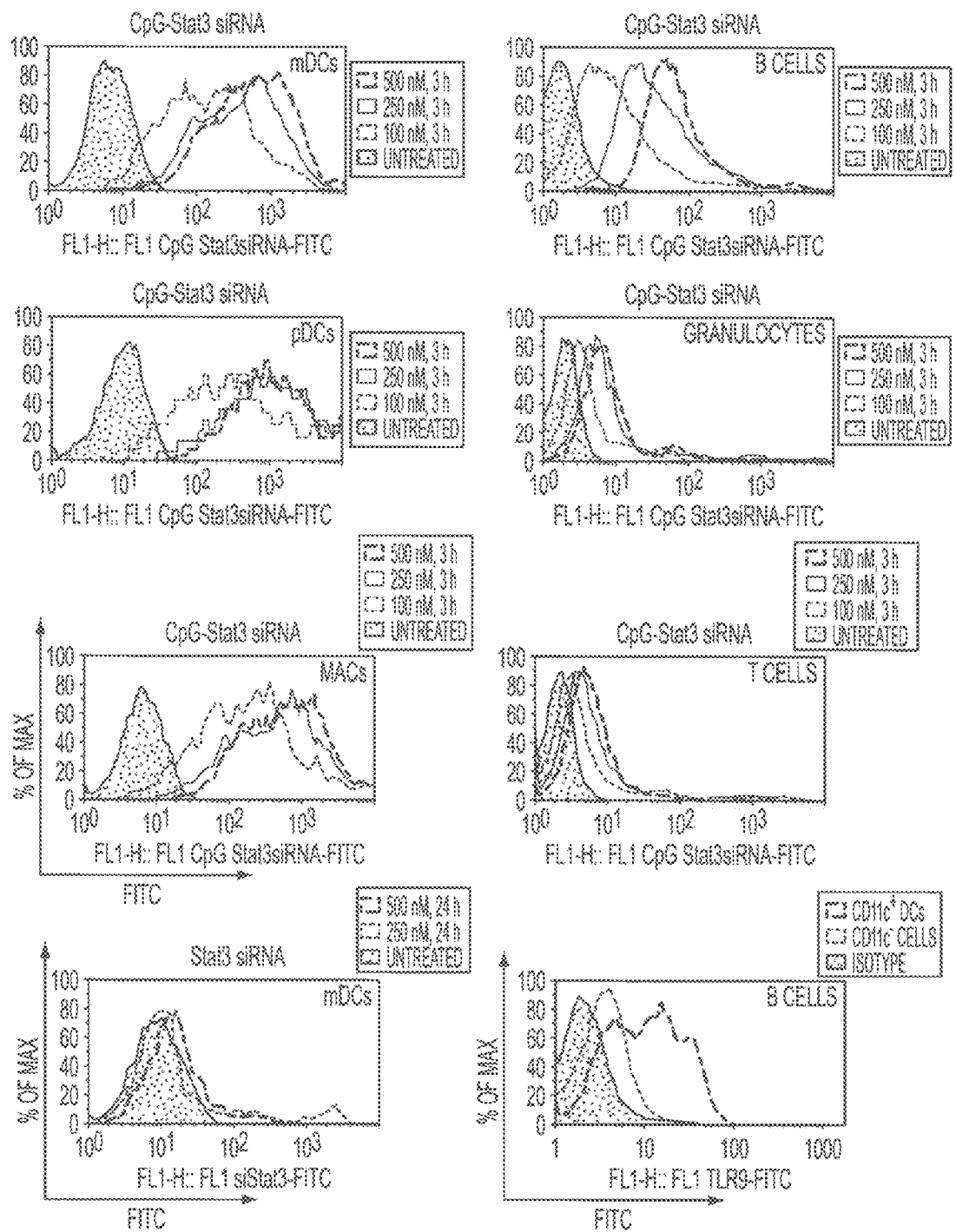
Figure 14:
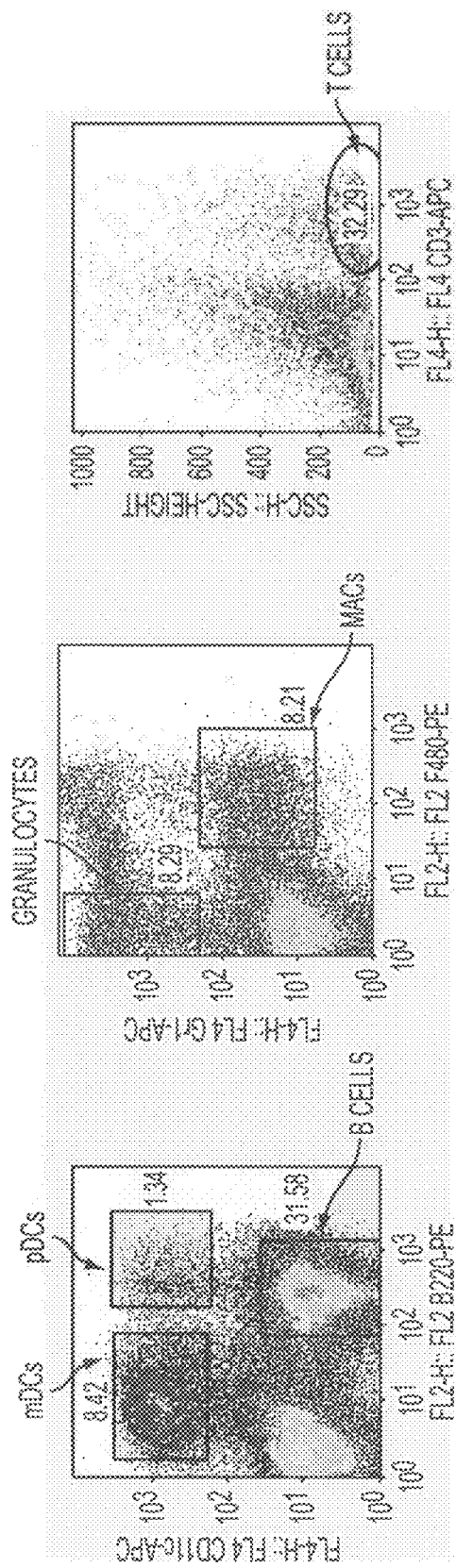
FIG. 14 shows the gating of various immune cell subsets for the analysis of in vitro CpG-Stat3 siRNA uptake. FACS analysis was performed on single-cell suspensions of splenocytes prepared as described in the legend to FIG. 13b. The percentages of FITC-positive cells shown in FIG. 13b and Table 1 were assessed in immune cell subtypes gated as indicated.

Cell Specific Uptake and Gene Silencing Effects by the CpG-siRNA Conjugate Molecules To determine the specificity and efficiency of CpG-siRNA uptake, freshly prepared mouse splenocytes were incubated for 3 h with two concentrations of CpG-linked Stat3 siRNA or an unconjugated Stat3 siRNA, in the absence of any transfection reagent(s). Both the CpG-Stat3 siRNA and unconjugated Stat3 siRNA were labeled with fluorescein. Fluorescein-positive DCs, macrophages, B cells, granulocytes and T cells were assessed by FACS analysis. Results from the flow cytometric analyses indicated that the chimeric CpG-Stat3 siRNA was efficiently taken up by both plasmacytoid (CD11c$^+$B220$^+$) and conventional (CD11c$^+$B220$^-$) splenic DCs, macrophages (F4/80$^+$Gr1$^-$) and B cells (B220$^+$CD11c$^-$), whereas uptake by splenic granulocytes (Gr1$^+$F4/80$^-$) or T cells (CD3$^+$) was minimal (FIG. 13a, FIG. 14 and Table 1). This uptake pattern reflects the known distribution of TLR9 expression in murine leukocyte subsets (Hemmi et al., 2000; Iwasaki and Medzhitov, 2004). CD11c$^+$ DCs were confirmed to express TLR9, as shown by intracellular staining of TLR9 in fixed splenocytes by flow cytometry (FIG. 13a, bottom right). Unconjugated Stat3 siRNA was not efficiently incorporated into DCs even after 24 h incubation, demonstrating that linkage to the TLR9 ligand facilitates siRNA uptake (FIG. 13a, bottom left).

TABLE 1

| | Untreated | 100 nM | 250 nM | 500 nM |
|---|---|---|---|---|
| mDCs | 0% | 75% | 94% | 97% |
| pDCs | 0% | 83% | 96% | 98% |
| MCs | 0% | 75% | 91% | 96% |
| B cells | 0% | 22% | 64% | 94% |
| Granulocytes | 0% | 16% | 28% | 29% |
| T cells | 0% | 9% | 16% | 16% |

Figure 13B:
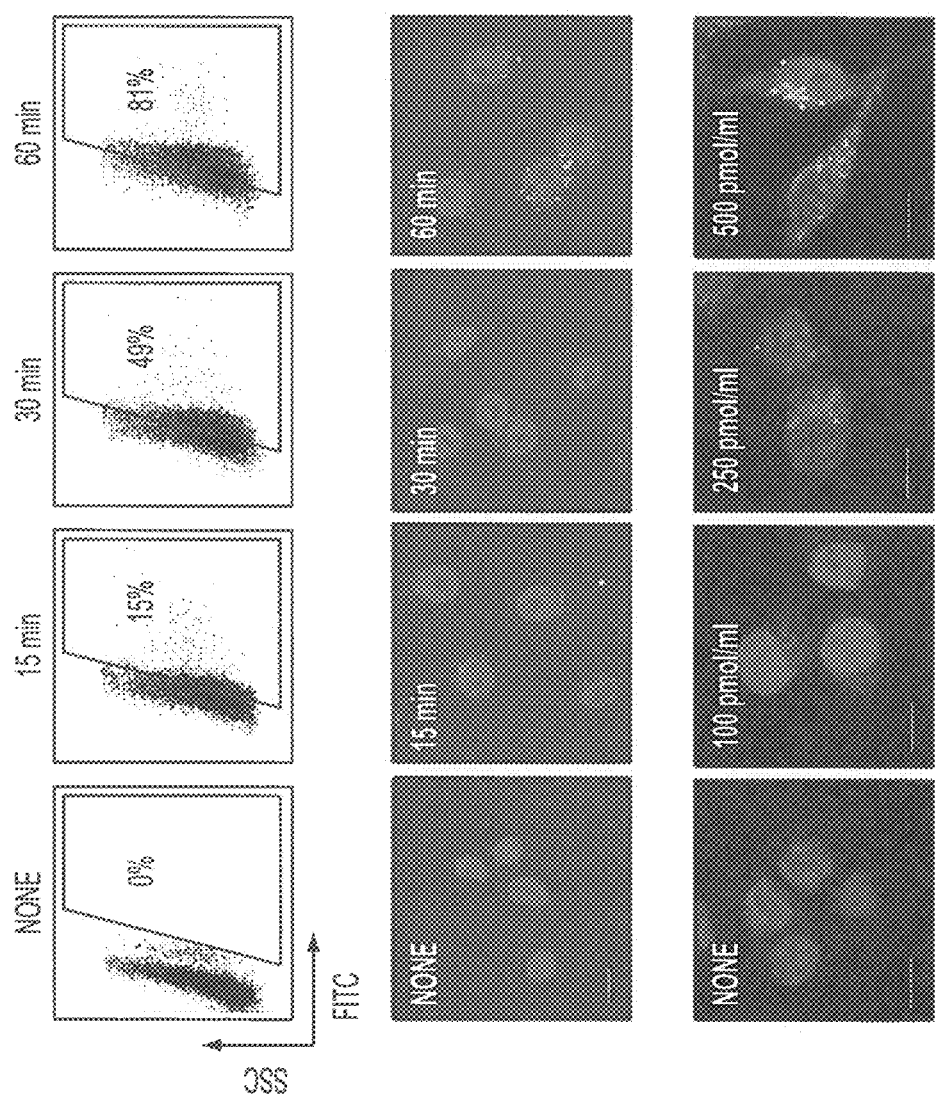
Figure 15:
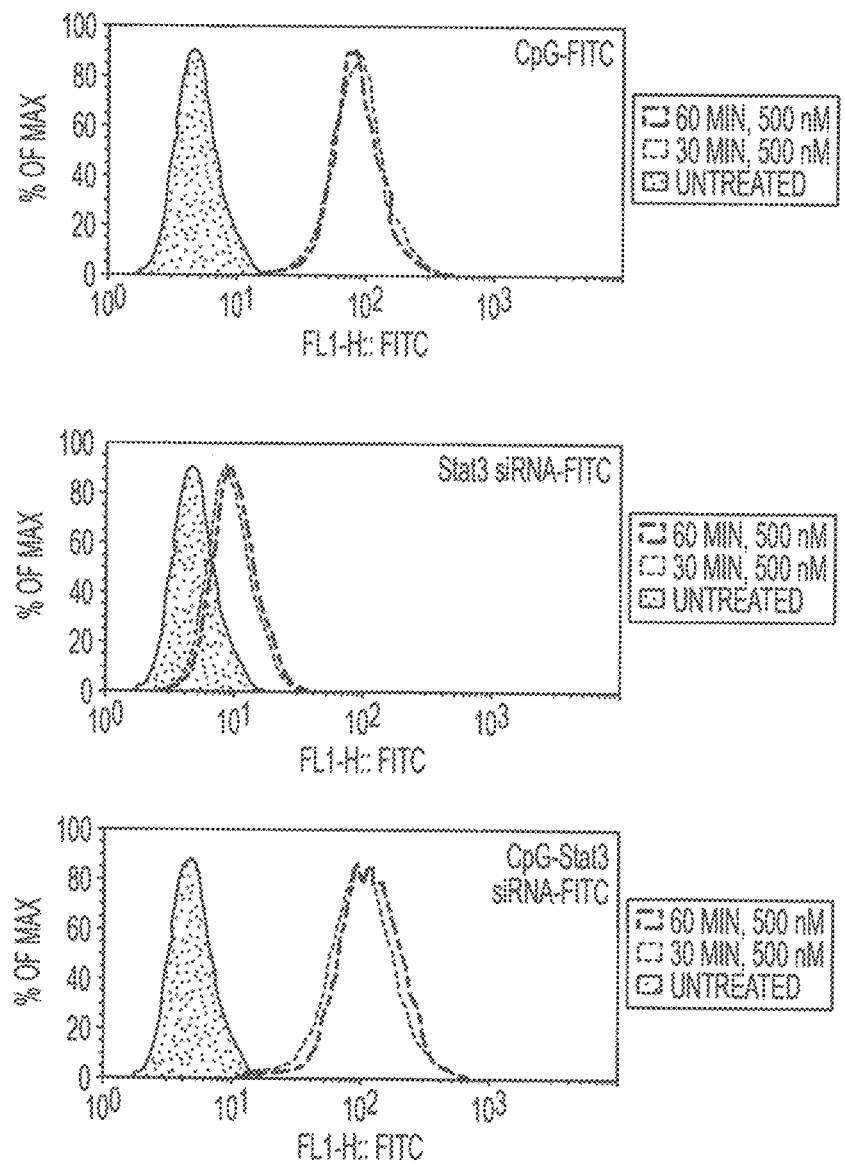
FIG. 15 shows a comparison of internalization kinetics of CpG ODN, siRNA and CpG-siRNA conjugate. The uptake of FITC-labeled molecules by DC2.4 cells was analyzed by flow cytometry after incubation at 500 nM for indicated times.

We further evaluated CpG-Stat3 siRNA-FITC uptake by DC 2.4 mouse dendritic cells. FACS analyses and fluorescent microscopy indicated that without transfection reagents, the CpG-Stat3 siRNA-FITC was internalized by DC 2.4 cells, with kinetics similar to that CpG-ODN alone and reported previously (Latz et al., 2004) (FIG. 13b—two top rows and FIG. 15). By 60 min, greater than 80% DC 2.4 cells were positive for uptake of the conjugate, which was confirmed by confocal microscopic analysis. The uptake of the CpG-Stat3 siRNA-FITC was dose dependent, observable at the concentration of 100 nM and reaching maximum at 500 nM (FIG. 13b, bottom row).

Figure 13C:
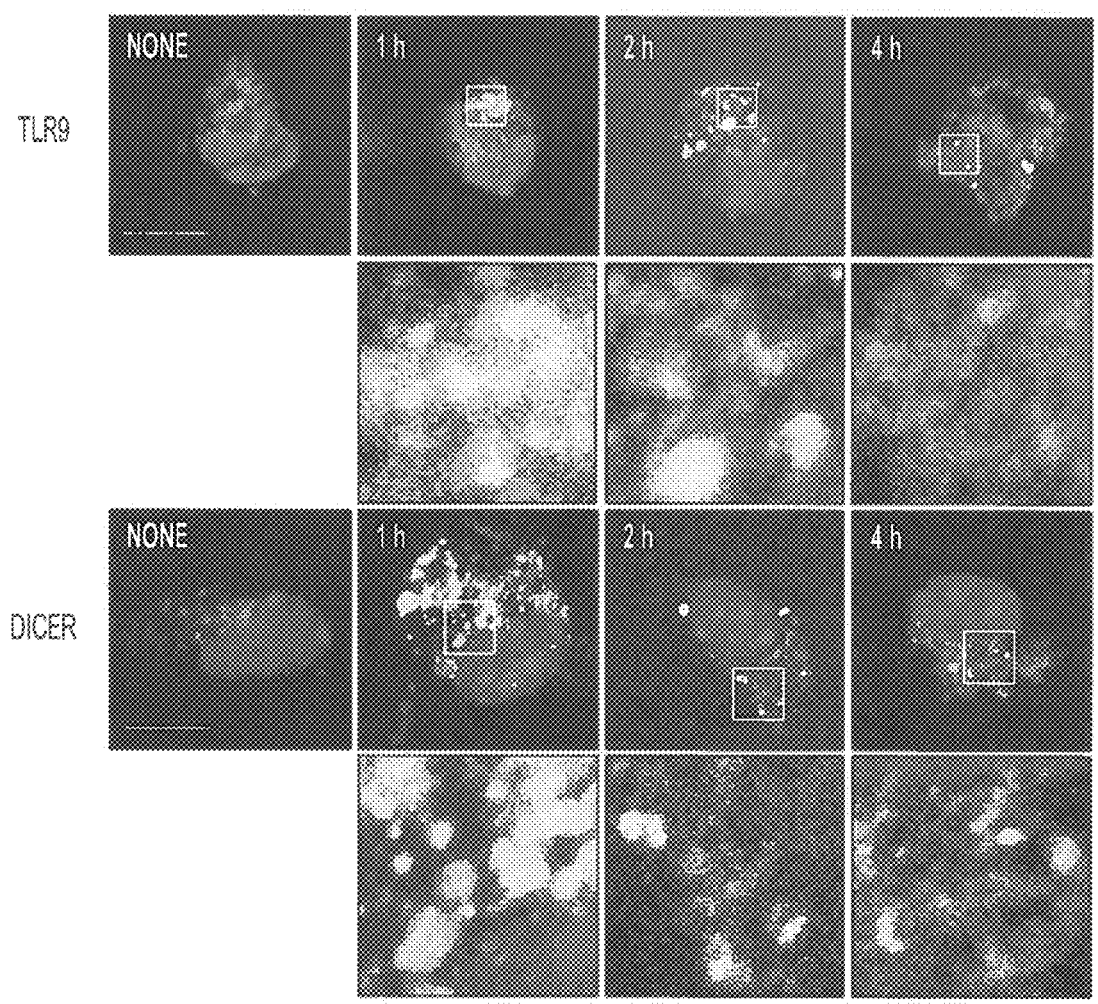
Figure 16:
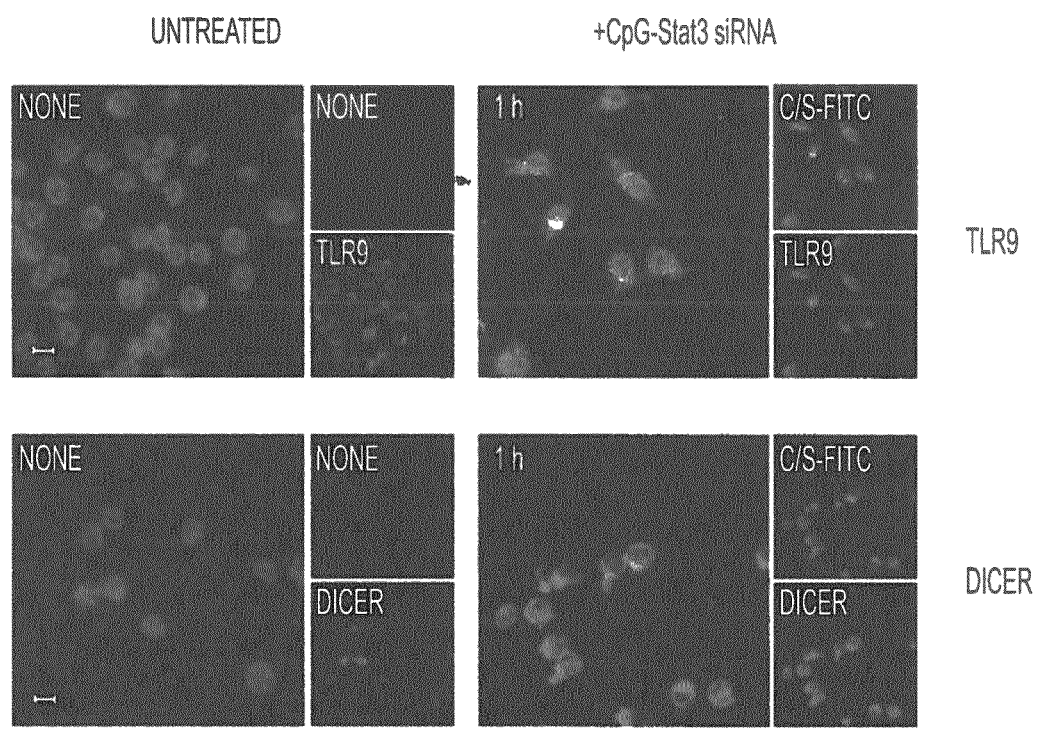
FIG. 16 shows colocalization of FITC-labeled CpG-Stat3 siRNA with TLR9 (top panels) and with Dicer (bottom panels) as shown by confocal microscopy. DC2.4 cells were incubated with 500 nM of CpG-Stat3 siRNA for 1 h. Shown are confocal microscopy images at lower magnification to visualize similar colocalization pattern in the majority of analyzed cells; green—CpG-Stat3 siRNA-FITC (C/S-FITC), red—immunofluorescent detection of endogenous TLR9 or Dicer, blue—nuclear staining with Hoechst. All confocal imaging studies were performed at least twice with similar results. Scale bar=10 μm.

Confocal microscopy analyses further showed that at one hour after incubation, the CpG-Stat3 siRNA colocalized with TLR9 within perinuclear endocytic vesicles (FIG. 13c, two top rows; and FIG. 16). This colocalization diminished at 2 and 4 h after CpG-siRNA treatment (FIG. 13c, two top rows.

Previous studies have demonstrated that binding of the Dicer nuclease to the siRNA oligonucleotide is required for further siRNA processing to shorter 21mer fragments that can mediate RISC complex-dependent mRNA degradation (Chendrimada et al., 2005). We observed transient colocalization of the CpG-Stat3 siRNA with Dicer within 2 h after adding the oligonucleotide to cultured dendritic cells (FIG. 13c, two bottom rows and FIG. 16). The colocalization of CpG-Stat3-siRNA and Dicer became weaker by 4 h (FIG. 13c) and undetectable after 24 h (data not shown).

Figure 17:
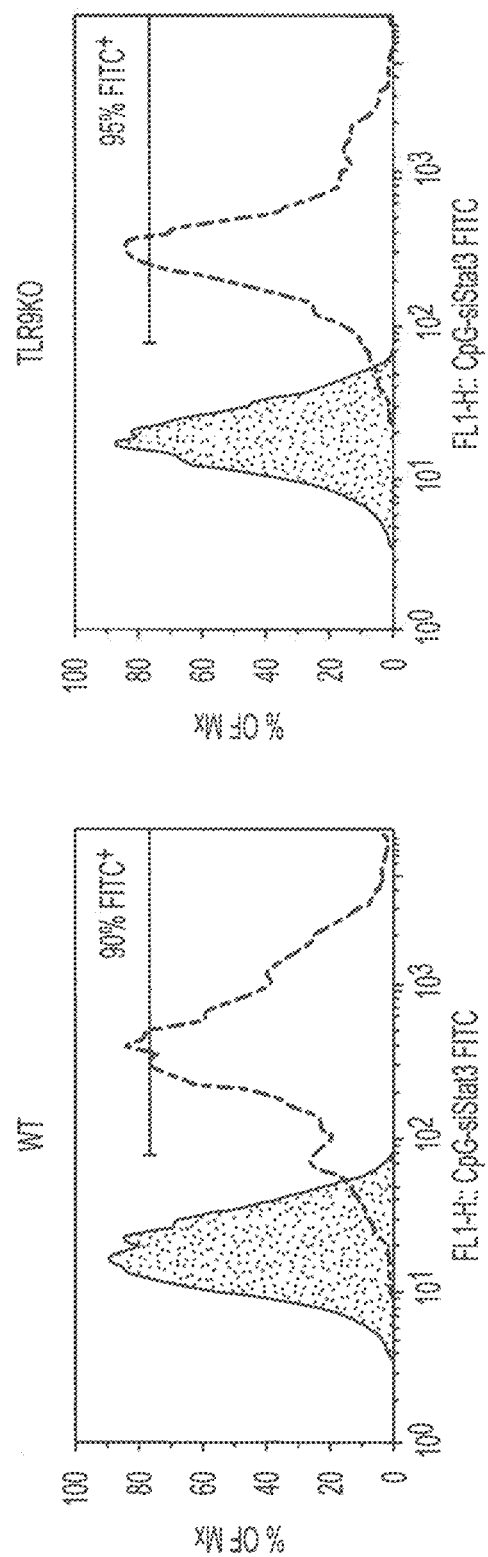
FIG. 17 shows that TLR9 is not required for uptake of FITC-labeled CpG-Stat3 siRNA. Cultured bone marrow-derived DCs (day 9) were incubated for 1 h with 500 nM CpG-Stat3siRNA labeled with FITC. Shown are percentages of fluorescein-positive $CD11c^+$ cells as assessed by FACS.

To determine gene silencing effects of the CpG-Stat3 siRNA, DC2.4 cells were incubated with CpG-Stat3 siRNA, CpG-scrambled RNA or GpC-conjugated Stat3 siRNA. Quantitative real-time PCR analysis of the Stat3 mRNA expression in DC2.4 cells indicated a dose-dependent down-regulation of Stat3 expression by CpG-Stat3 siRNA, compared to CpG-scrambled RNA (FIG. 13d). Maximum effect on Stat3 silencing (ca. 80% reduction) was observed at relatively high 1 µM concentration of CpG-Stat3 siRNA in serum-containing cell culture medium. GpC-conjugated Stat3 siRNA, which binds but does not activate TLR9 (Latz et al. 2004), failed to silence Stat3, suggesting a possible requirement of TLR9 activation for the CpG-siRNA to be further processed. Further experiments demonstrated that in TLR9$^{-/-}$ myeloid cells and DCs, while cellular uptake of CpG-Stat3 siRNA was normal (FIG. 17), the gene silencing effect of CpG-siRNA was completely impaired (FIG. 13e). We further confirmed the gene silencing effects using electrophoretic mobility shift assays (EMSA) to detect Stat3 DNA-binding activity in DC2.4 cells, which was induced by IL-10 stimulation (FIG. 13f). Note that, as indicated above, stimulation using CpG itself also resulted in Stat3 activation, which serves as a negative feedback mechanism (Kortylewski et al., 2009b; Samarasinghe et al., 2006) (FIG. 13O, thereby complicating the EMSA analysis for detection of Stat3 silencing. None-the-less, the higher concentrations of CpG-Stat3 siRNA diminished Stat3 DNA binding activity relative to the conjugate scrambled RNA controls.

Figure 18B:
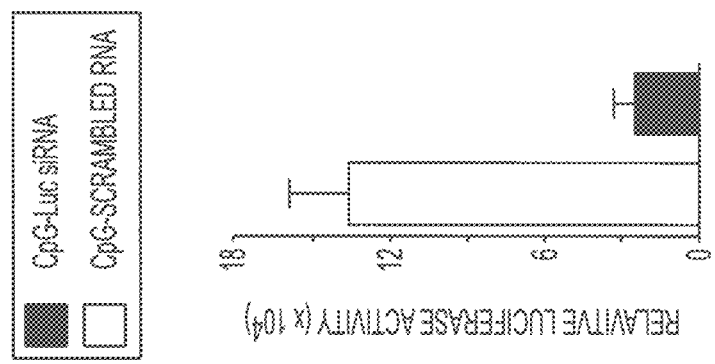
FIGS. 18a-18b show CpG-siRNA uptake and gene silencing effects in A20 B cell lymphoma cells.
Figure 18A:
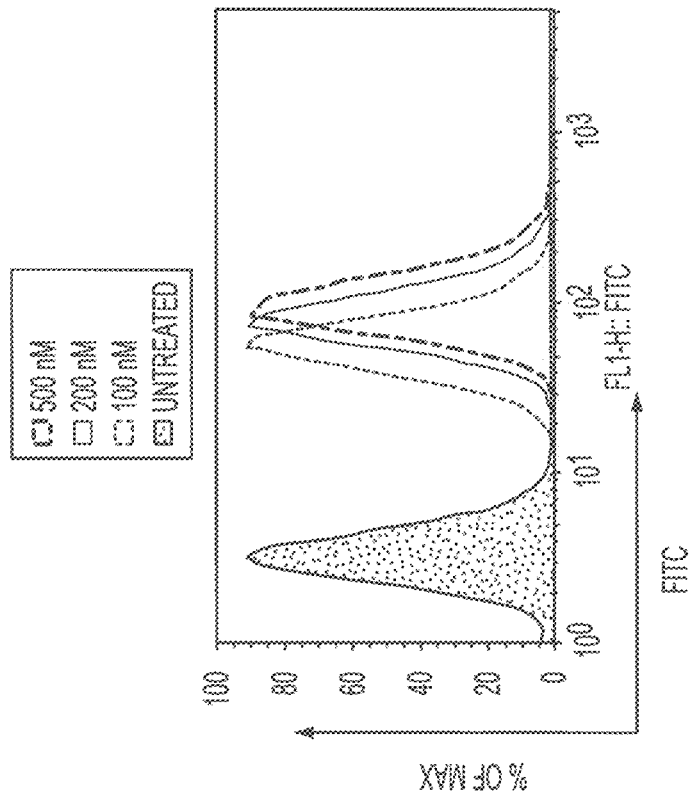

To demonstrate the generality of this approach to gene silencing, we used another system to verify the gene silencing effects of the CpG-siRNA constructs. Mouse A20 B cell lymphoma cells, which are TLR9-positive, could internalize CpG-siRNA (FIG. 18a). A chimeric conjugate linking a Dicer substrate siRNA specific for firefly luciferase (Luc) conjugated to the 20 deoxyribonucleotides CpG1668 ODN (CpG-Luc siRNA) inhibited luciferase overexpression in A20-Luc cells, which was determined by measuring luciferase activity (FIG. 18b).

Example 14

Antitumor Effects of the CpG-Stat3siRNA Conjugate Molecule

Figure 19:
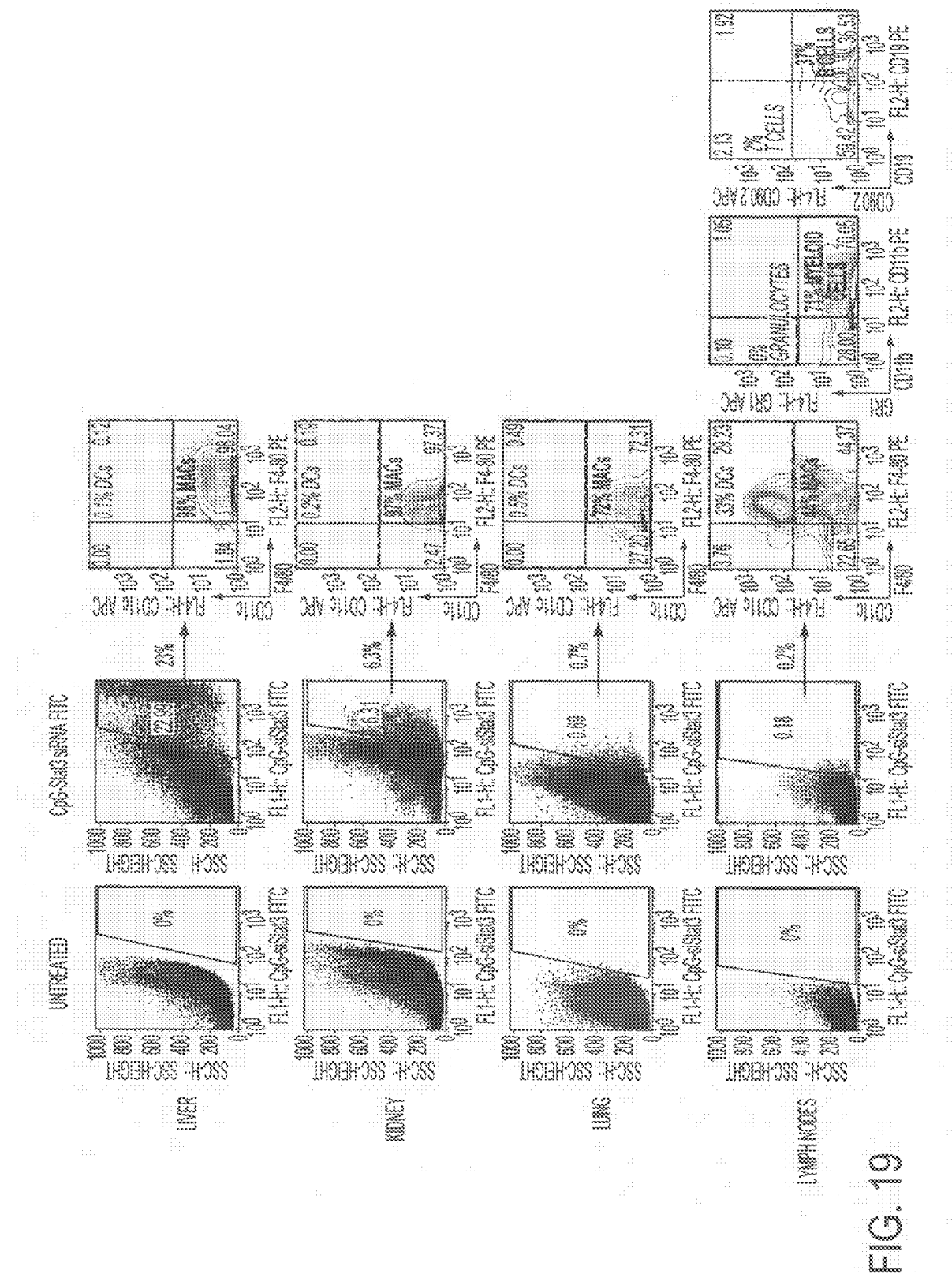
FIG. 19 shows the biodistribution of systemically injected CpG-Stat3 siRNA. Mice were sacrificed 3 h after retroorbital venous injection of 100 μg FITC-labeled CpG-Stat3 siRNA. Harvested tissues were enzymatically dispersed into single cell suspension, enriched for mononuclear cells and analyzed by FACS for the presence of various immune cell subsets as indicated. Shown are representative results of two independent experiments using 2-3 mice analyzed individually. This figure shows that the systemic delivery of siRNA by CpG-siRNA construct efficiently targets myeloid cells in liver, kidney and lung.
Figure 20A:
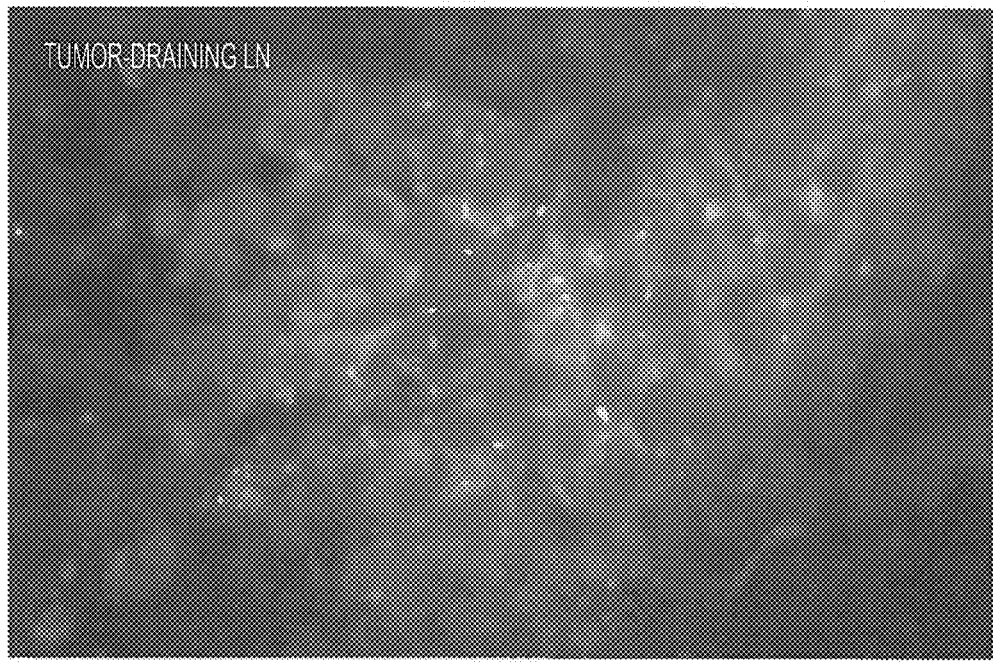
FIGS. 20a-20e show that treatment with CpG-Stat3 siRNA leads to cell-specific gene silencing in vivo.
Figure 20B:
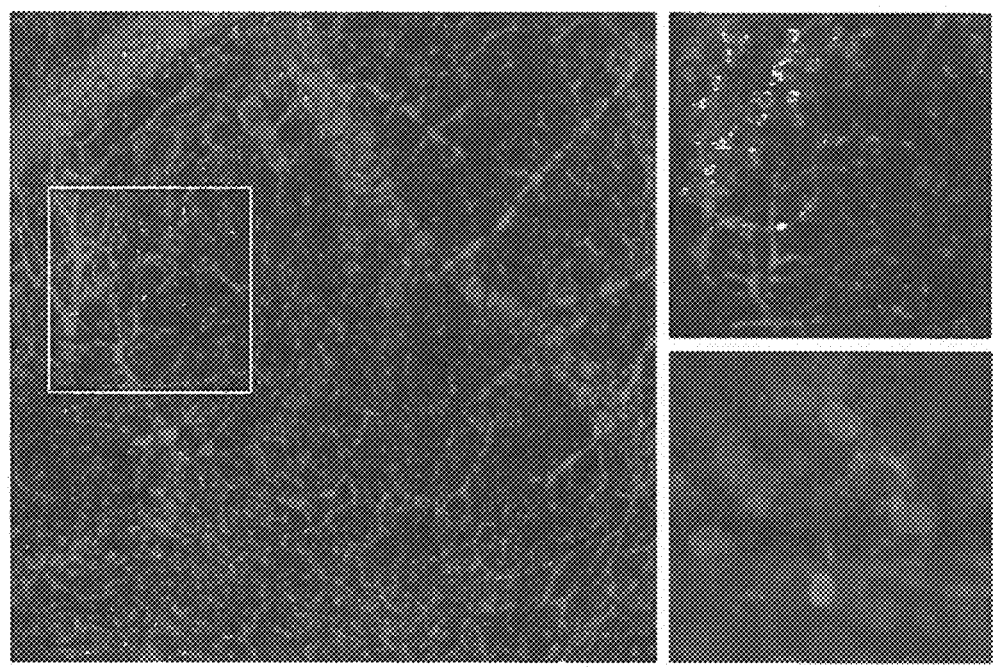
Figures 21A, 21B:
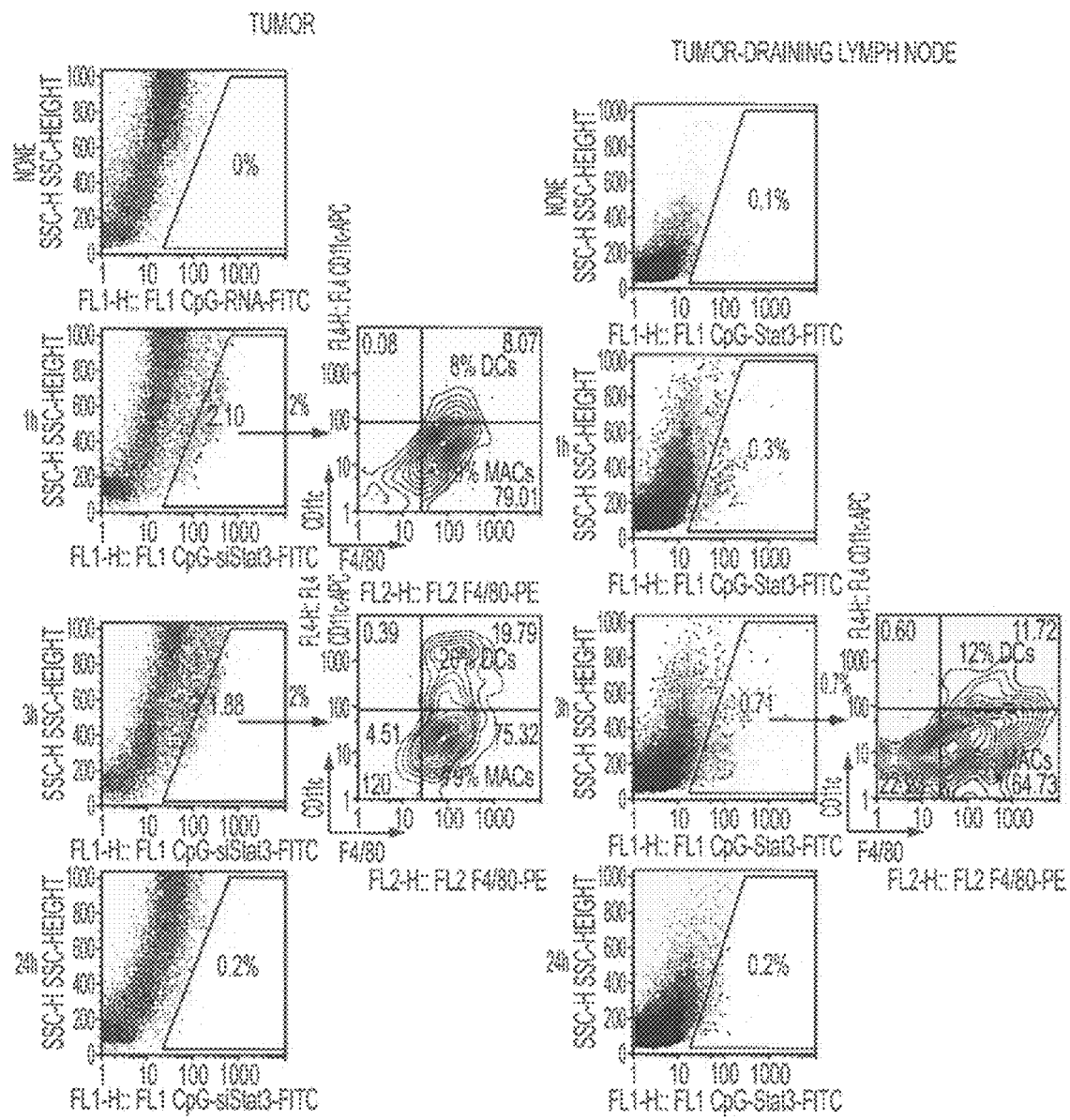
FIGS. 21a-21b show the kinetics of CpG-Stat3 siRNA uptake in vivo following intratumoral injection. Mice were sacrificed after i.t. injection of 20 µg FITC-labeled CpG-Stat3 siRNA at indicated times. Single-cell suspensions of tumors (FIG. 21a) and tumor-draining lymph nodes (FIG. 21b) were enriched for viable mononuclear cells and analyzed by FACS for the presence of F4/80$^+$CD11c$^-$ macrophages and CD11c$^+$ DCs. Shown are representative results of two independent experiments using 2-3 mice analyzed individually. This figure shows that local tumor treatment allows CpG-siRNA to enter macrophages and dendritic cells.
Figure 22:
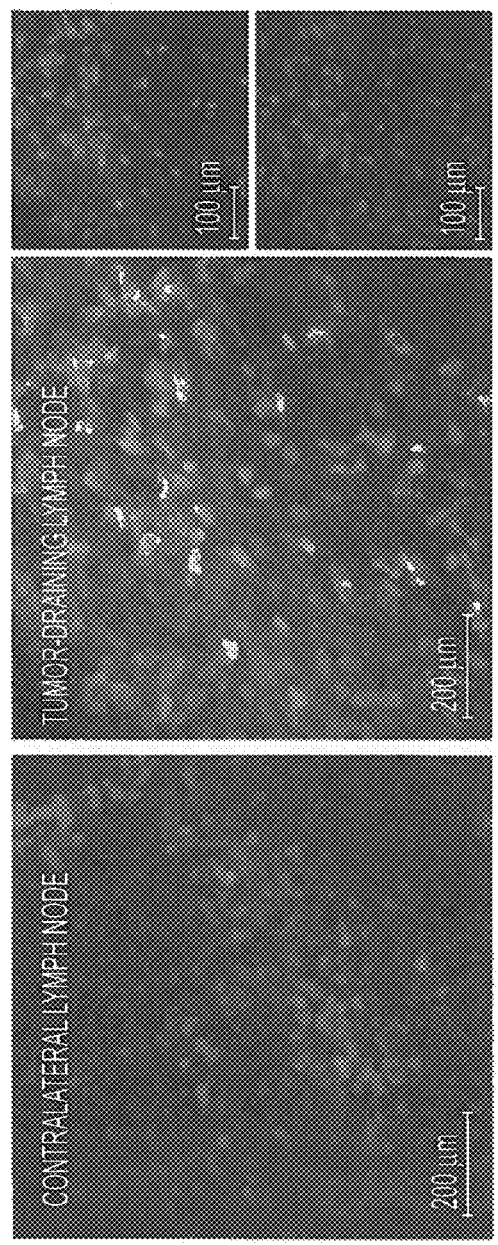
FIG. 22 shows the in vivo uptake of intratumorally injected CpG-Stat3 siRNA by myeloid cells. Intravital two-photon microscopy on tumor-draining and contra-lateral lymph nodes at 1 h after single intratumoral injection of 20 µg FITC-labeled CpG-Stat3siRNA (green) together with intravenously injected Hoechst 33342 for nuclear staining (blue). For tumor-draining lymph node, the overlay image was split into green (upper right panel) and blue (lower right panel) channels to visualize better cellular localization of the injected CpG-Stat3siRNA.

To evaluate the feasibility of using the CpG-siRNA conjugates in vivo for therapeutic purposes, we focused on potential immunologically mediated anti-tumor effects of the CpG-Stat3 siRNA conjugates. The initial biodistribution experiments in naive tumor-free mice confirmed that CpG-Stat3 siRNA is specifically internalized by resident macrophages in different tissues as well as DCs and B cells in lymph nodes (FIG. 19). Next, we estimated the uptake of the CpG-Stat3 siRNA by macrophages and dendritic cells in tumor-bearing mice. C57BL/6 mice with aggressive poorly immunogenic B16 tumors (6-10 mm in diameter) were injected peritumorally with FITC-labeled CpG-Stat3 siRNA at 0.78 nmol (20 mg)/injection. As shown by immunofluorescent staining and FACS analysis, numerous myeloid cells accumulated at the site of CpG-Stat3 siRNA injection already 1 h later (FIG. 20a and FIG. 21a). Furthermore, in vivo intravital two-photon microscopy indicated the presence of FITC-positive cells in tumor-draining lymph node, as early as 1 h after injection of the labeled construct (FIG. 20b, FIG. 21b and FIG. 22), but not in the contralateral lymph nodes (FIG. 22). Additionally, high resolution imaging by intravital two-photon microscopy revealed not only an increased number of FITC-positive cells in tumor draining lymph nodes, but also an accumulation of FITC-labeled CpG-Stat3 siRNAs in perinuclear endocytic vesicles (FIG. 20b, bottom right), which was also observed in cultured dendritic cells (FIG. 13c).

Figure 20E:
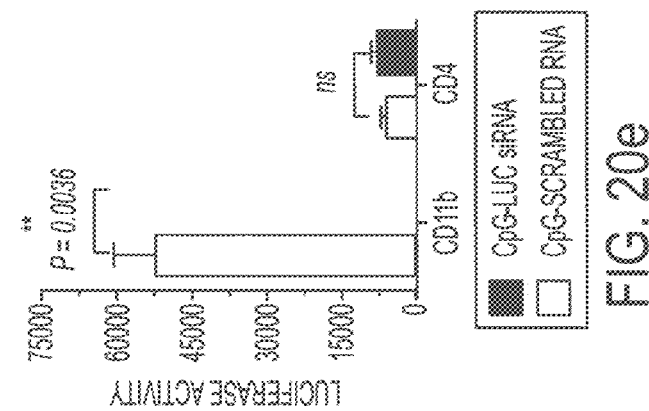
Figure 20D:
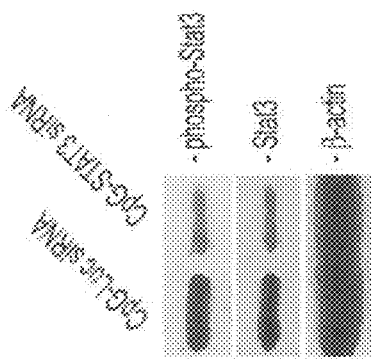
Figure 20C:
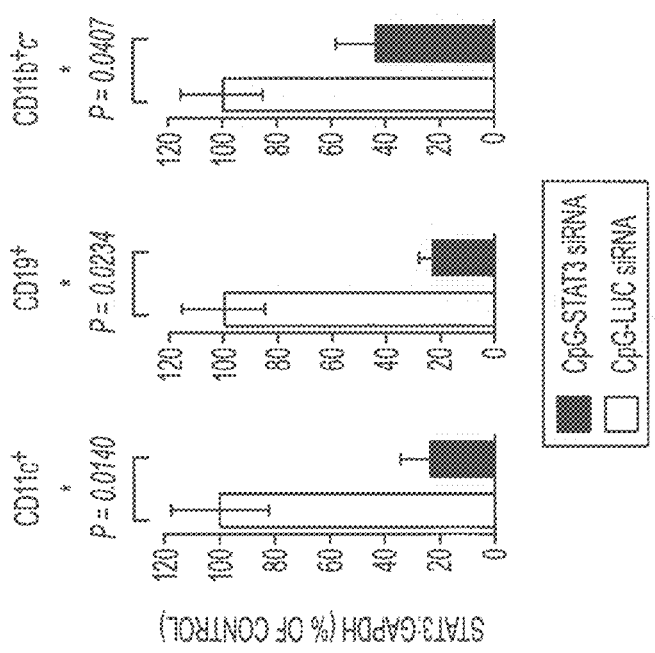
Figure 23A:
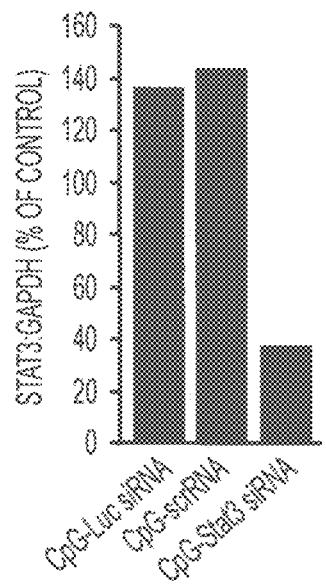
FIGS. 23a and 23b show the local treatment with CpG-Stat3 siRNA reduces Stat3 expression within total tumor-draining lymph nodes. Mice with subcutaneous B16 tumors were treated by repeated peritumoral injections using various CpG-RNAs or PBS alone as indicated, every second day, starting six days after challenge with 1×10$^5$ B16 cells using 7 mice/group. Single cell suspensions prepared from pooled tumor-draining lymph nodes were used for further analyses of Stat3 expression.
Figure 23B:
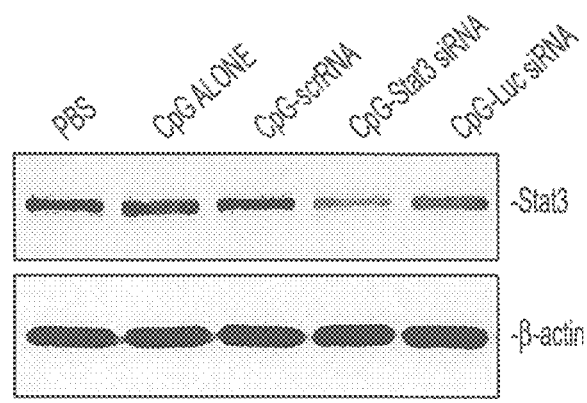

We next evaluated the gene silencing and antitumor effects of CpG-Stat3 siRNAs in vivo. Peritumoral injections of the CpG-Stat3 siRNA resulted in relatively effective gene silencing in dendritic cells, macrophages and B cells accumulated in tumor draining lymph nodes, compared to control CpG-Luc siRNA, as measured by quantitative real-time PCR (FIG. 20c). Stat3 inactivation in CD11c+ dendritic cells isolated from tumor draining lymph nodes was confirmed at protein level (FIG. 20d). Furthermore, quantitative real-time PCR and Western blotting indicate Stat3 silencing in the total tumor draining lymph nodes as well (FIG. 23). We also used CpG-Luc siRNA conjugate to confirm that CpG-siRNA conjugates are able to reduce protein expression specifically within myeloid cells in vivo. Mice over-expressing firefly luciferase under control of the β-actin promoter (Cao et al., 2004) were challenged with tumor cells, followed by repeated peritumoral injections of CpG-Luc siRNA. Results from these experiments indicated effective inhibition of luciferase activity in CD11b+ myeloid cells but not in CD4+ lymphocytes within tumor-draining lymph nodes (FIG. 20e).

Figure 24A:
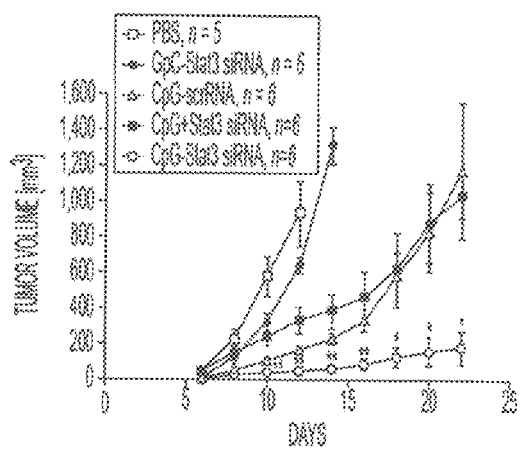
FIGS. 24a-24g show that local treatment with CpG-Stat3 siRNA inhibits tumor growth.
Figure 24B:
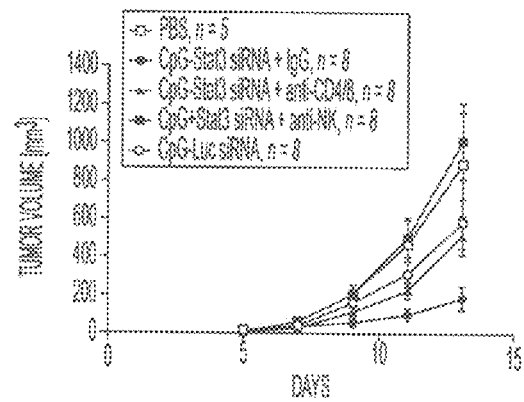

Both dendritic cells and macrophages in the tumor microenvironment are known to promote immune tolerance (Dhodapkar et al., 2008; Vicari et al., 2002; Zou et al. 2005). Our previous work demonstrated that Stat3 is constitutively-activated in myeloid cells in the tumor milieu and that genetic ablation of Stat3 in the myeloid compartment elicits potent antitumor immunity (Kortylewski et al., 2005b). Furthermore, both CpG and LPS treatment activates Stat3 (Samarasinghe et al., 2006; Kortylewski et al., 2009b; Benkhart et al., 2000), which acts as a negative feedback mechanism to constrain Th1 immune responses. Therefore, we assessed whether the CpG-Stat3-siRNA conjugates could reverse the immunosuppressive effects imposed by the tumor-microenvironment and at the same time allow effective antitumor immunity induced by TLR9 triggering. Local treatment with CpG-Stat3 siRNA oligonucleotides inhibited growth of subcutaneously growing B16 melanoma (3-5 mm in diameter at the initial treatment). In contrast, treatment with unconjugated CpG-ODN plus Stat3 siRNA, or CpG-scrambled RNA construct, or GpC-Stat3 siRNA had significantly less antitumor effects (FIG. 24a). This finding was confirmed by using two additional CpG-Stat3 siRNA conjugates containing alternative Stat3 siRNA sequences (data not shown). To confirm that the antitumor effects induced by CpG-Stat3 siRNA were mainly mediated by immune cells, we performed in vivo experiments with antibody-mediated depletion of CD8/CD4 T cells and NK cells. As shown in FIG. 24b, in the absence of CD8+ and CD4+ immune cell populations (including possibly also the cross priming CD11c+CD8+ DCs), the effects of CpG-Stat3 siRNA treatment were partially reduced and comparable to the moderate antitumor effect of the control CpG-Luc siRNA, and lack of NK cells abrogated therapeutic effect of CpG-Stat3 siRNA.

Figure 24C:
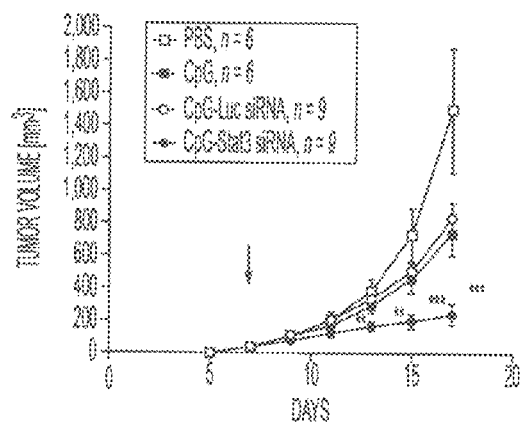
Figure 24D:
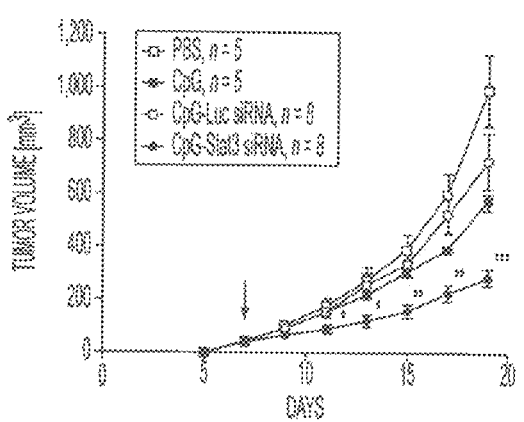
Figure 24E:
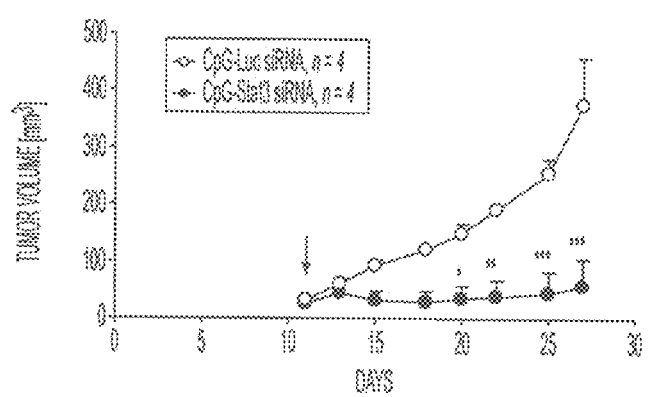
Figure 25:
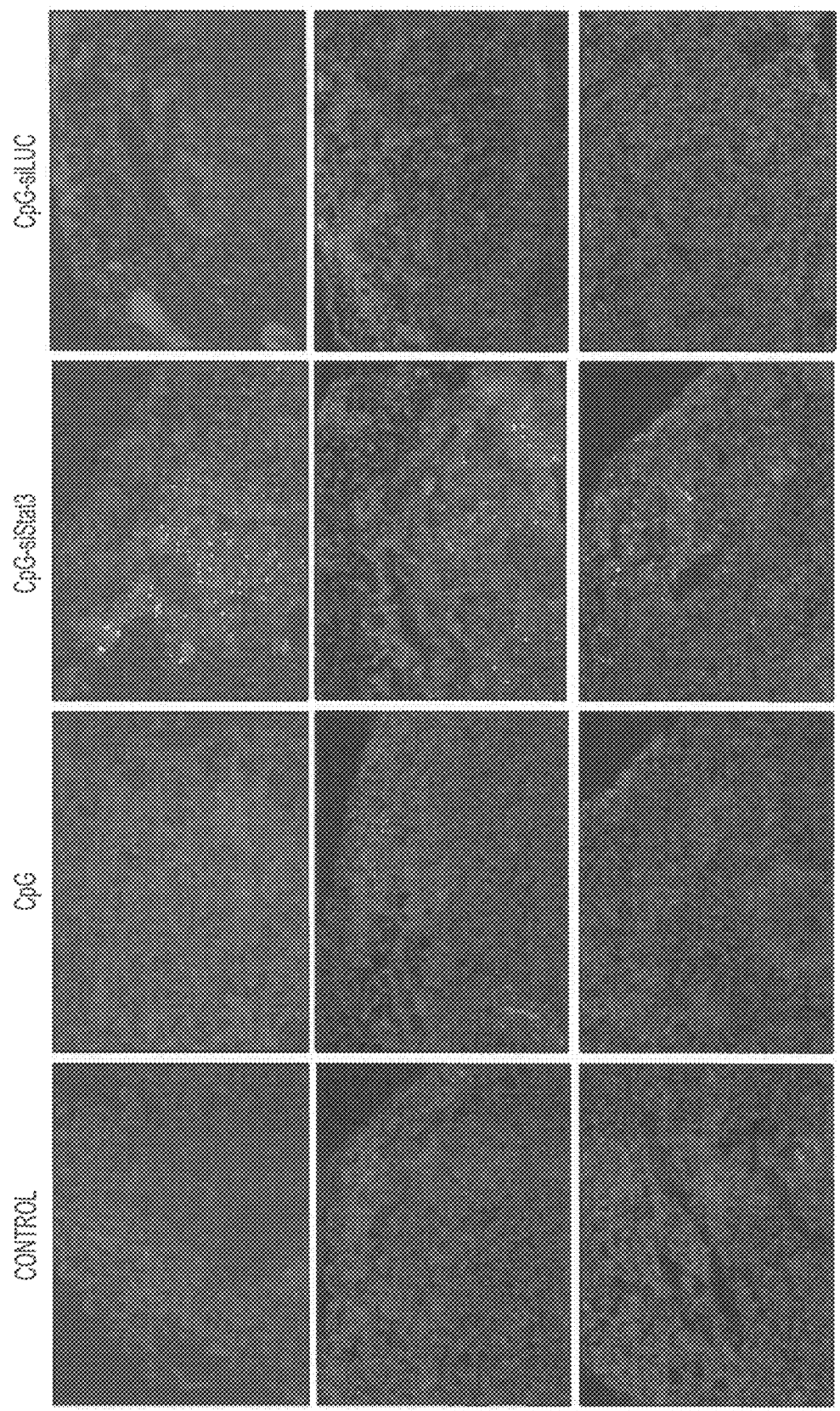
FIG. 25 shows augmented cell apoptosis within B16 tumors following peritumoral treatment with CpG-Stat3siRNA. Frozen sections prepared from B16 tumors injected 3 times using PBS, CpG, or CpG-siRNA conjugates, were analyzed by immunofluorescence using antibodies specific to active caspase-3 to detect apoptosis (red) and counterstained with Hoechst (blue) for visualization of nuclei. Shown are representative results from two independent experiments using samples isolated from 4 individual mice; original magnification, ×100.

We confirmed that local treatment with CpG-Stat3 siRNA can reduce growth of other tumors independently of their genetic background. CpG-Stat3 siRNA oligonucleotides inhibited growth of both a poorly immunogenic variant of K1735 melanoma, C4 (Xie et al., 2004), and CT26 colon carcinomas in C3H and BALB/c mice, respectively (FIGS. 24c, 24d). Furthermore, CpG-Stat3 siRNA treatment of the carcinoembryonic antigen (CEA) transgenic C57BL/6 mice bearing MC38 colon carcinomas expressing CEA led to tumor regression (FIG. 24e). To assess in vivo effects of the CpG-Stat3 siRNA on tumor cells, we stained B16 tumor tissues with fluorescent antibody specific to activated caspase-3. Data from these analysis showed that B16 tumors received CpG-Stat3 siRNA had undergone more extensive apoptosis relative to the other three treatment groups (FIG. 25).

Figure 24F:
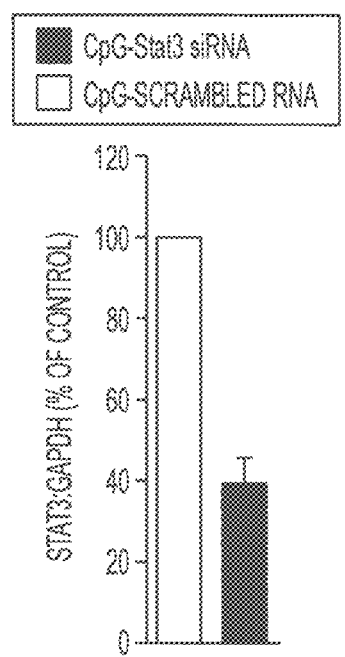
Figure 24G:
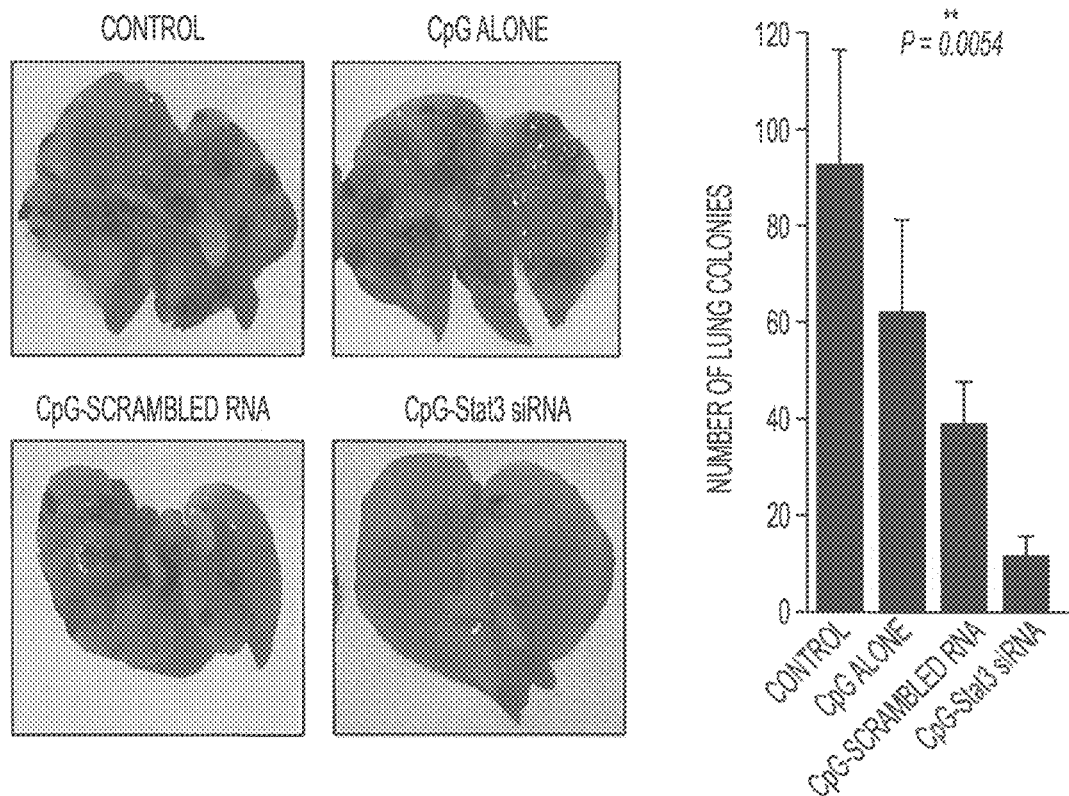

We further investigated the possibility that intravenous injections of CpG-Stat3 siRNA can lead to gene silencing and antitumor effects. Intravenous injection of CpG-Stat3 siRNA (0.78 nmol) reduced Stat3 expression in dendritic cells within tumor-draining lymph nodes relative to CpG-scrambled RNA (FIG. 24f). We also tested the ability of systemic delivery of CpG-Stat3 siRNA to inhibit metastatic tumor growth in an established B16 lung metastasis model. Mice with disseminated B16 tumor cells were treated systemically with CpG-Stat3 siRNA thrice weekly for two weeks. Relatively small amounts of the oligonucleotide (<1 mg/kg) were used for the systemic injection, which led to significant reduction in the number of lung metastasis (FIG. 24g). A significantly lower antitumor effect due to CpG-scrambled RNA and CpG ODN alone was also observed. Thus, maximal antitumor effects required conjugation of the CpG TLR9 ligand with a functional Stat3 siRNA.

Example 15

Figure 26A:
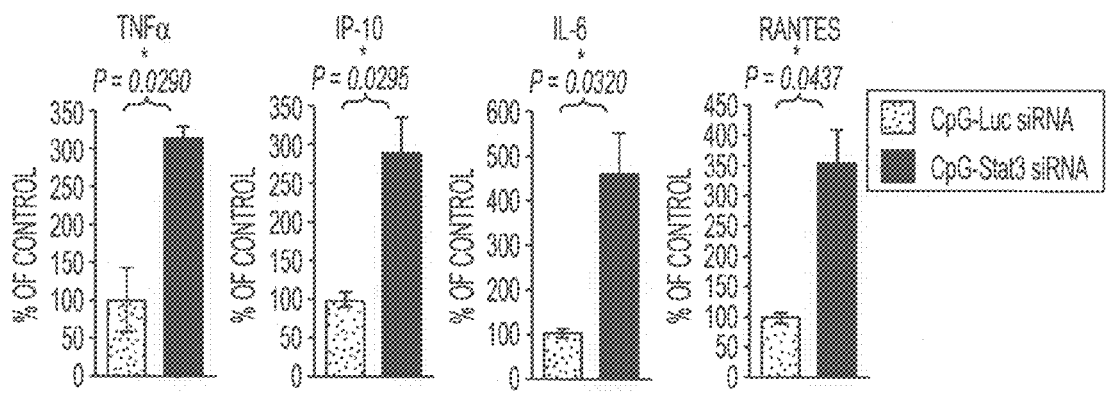
FIGS. 26a-26c show in vivo administration of CpG-Stat3 siRNA induces proinflammatory cytokine expression and activates innate immunity.
Figure 26B:
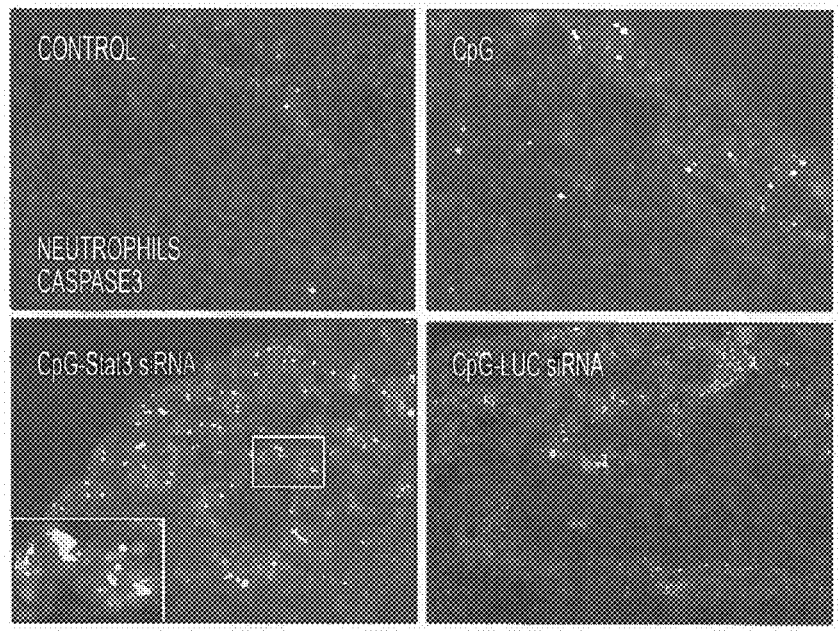
Figure 26C:
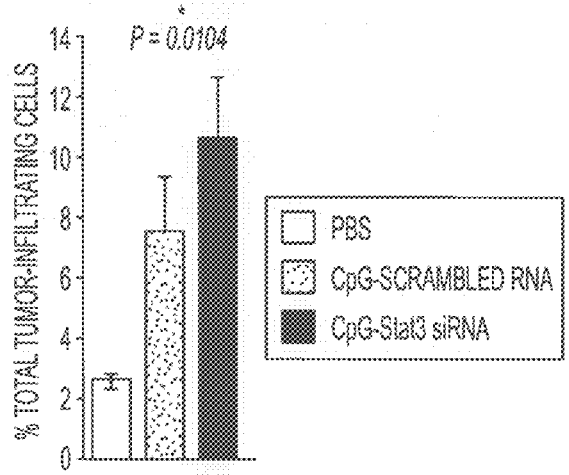
Figure 27:
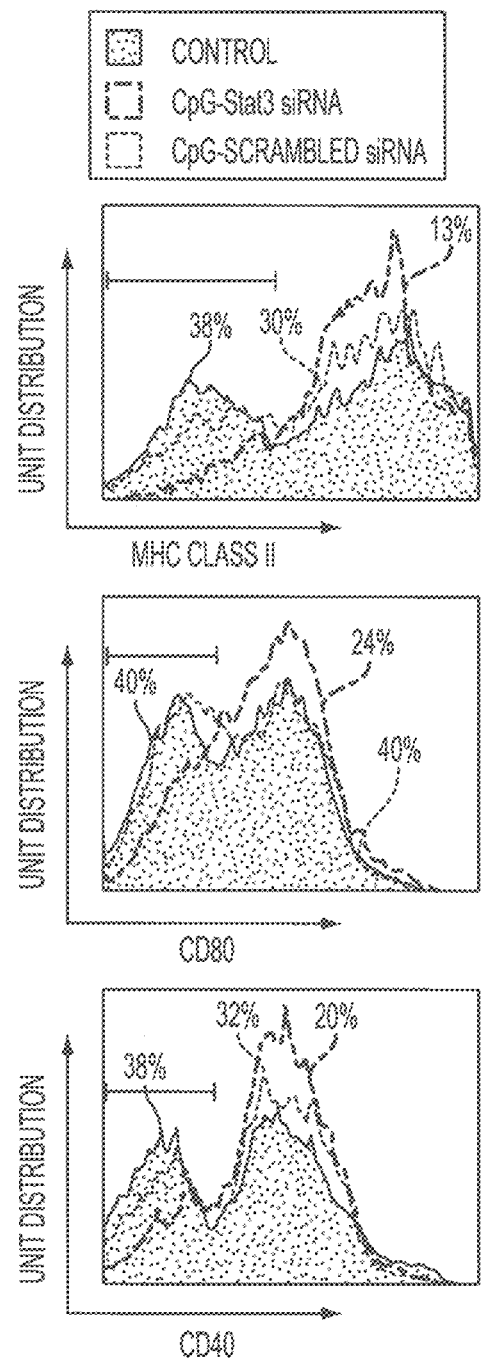
FIG. 27 shows reduction of immature DCs in the tumor draining lymph nodes. B16 tumor bearing mice were treated peritumorally with CpG-Stat3siRNA or CpG-scrambled RNA as described in FIG. 20d. Shown are results of flow cytometric analyses performed on single cell suspensions prepared from tumor-draining lymph nodes pooled from 5-6 mice; the percentages of DCs with low expression of MHC class II or co-stimulatory molecules are indicated.

Modulation of the Tumor Immunologic Milieu by the CpG-Stat3 siRNA Conjugate Molecule To further assess the role of immune modulation in the observed antitumor effects mediated by CpG-Stat3 siRNA conjugate treatment, we analyzed changes in Th1 cytokine/chemokines and co-stimulatory molecule expression by dendritic cells in the tumor draining lymph nodes. Lack of Stat3 in DCs has been shown to upregulate expression of Th1 cytokines/chemokines (Kortylewski et al., 2005b; Kortylewski et al., 2009a; Takeda et al., 1999; Welte et al., 2003), which can be greatly amplified by CpG treatment (Kortylewski et al., 2009b;). As shown in FIG. 26a, local tumor site injection of the CpG-Stat3 siRNA resulted in upregulation of several Th1 cytokines and chemokines, which were shown to be upregulated by Stat3 ablation (Kortylewski et al., 2005b; Kortylewski et al., 2009a; Takeda et al., 1999; Welte et al., 2003). It has also been documented that dendritic cells with low expression levels of co-stimulatory molecules mediate immune tolerance (Dhodapkar et al., 2001), which is one of the proposed mechanisms for tumor immune evasion induced by Stat3 activation in tumor-associated dendritic cells (Kortylewski et al., 2005b). We therefore analyzed expression of co-stimulatory molecules by dendritic cells enriched from tumor draining lymph nodes. Results from these analyses indicated that CpG-Stat3 siRNA reduced the number of the dendritic cells with low expression of co-stimulatory molecules, including MHC class II, CD80 and CD40, which was accompanied by a modest increase in expression of these co-stimulatory molecules (FIG. 27). Stat3 ablation in myeloid cells followed by local treatment has been shown to induce potent antitumor innate immune responses that involve neutrophils (Kortylewski et al., 2005b). We therefore assessed whether CpG-Stat3 siRNA conjugate treatment could lead to neutrophil-associated tumor cell apoptosis. Co-staining B16 tumor tissue sections with antibodies specific to activated caspase-3 and neutrophils revealed that CpG-Stat3 siRNA treatment-induced massive tumor cell apoptosis (activated caspase 3-positive) was associated with an increase in tumor-infiltrating neutrophils (FIGS. 28a, 28b).

The ratio of effector to regulatory T cells within the tumor microenvironment is considered to correlate well with the effect of adaptive immune responses on tumor progression and metastasis (Bui et al., 2006). We investigated the numbers of tumor infiltrating T cell populations in subcutaneously growing B16 tumors treated locally for 2 weeks with CpG-Stat3 siRNA, CpG-scrambled RNA control or treated with PBS only (FIG. 24a). We found that although CpG-Stat3 siRNA treatment did not induce significant changes in overall $CD4^+$ T cell numbers within the tumors, as shown by flow cytometric analysis (FIG. 28a), the percentage of $CD4^+$/$FoxP3^+$ Treg cells within all $CD4^+$ T cells dropped from approximately 60% to 25% after peritumoral injections of CpG-Stat3 siRNA (FIG. 28b). We observed an increase in the infiltration of total $CD8^+$ T cells in the tumor stroma from 5% to almost 20%, although CpG-scrambled RNA control treatment also led to some recruitment of $CD8^+$ T cells, as shown by flow cytometric analysis (FIG. 28c). These effects probably result from TLR9-mediated immunostimulation of tumor-infiltrating APCs. At the same time, we cannot rule out antitumor effects contributed by non-specific immunostimulation by double-stranded RNA. Fluorescent immunostaining of frozen tumor tissues with anti-CD8 antibody confirmed data generated by flow cytometric analysis (FIG. 28c) that CpG-Stat3 siRNA treatment caused increased $CD8^+$ T cell infiltration in tumors (data not shown). Activation of tumor antigen-specific $CD8^+$ T cells is believed to be critical for immune-mediated antitumor effects. We therefore examined the ability of CpG-Stat3 siRNA treatment to generate $CD8^+$ T cells specific for the B16 tumor antigen, TRP2. ELISPOT assays to determine IFN' production by T cells isolated from tumor draining lymph nodes in response to recall stimulation with TRP2 peptide indicated that in vivo CpG-Stat3 siRNA administration indeed induced antigen-specific $CD8^+$ T cells (FIG. 28d).

Figure 30A:
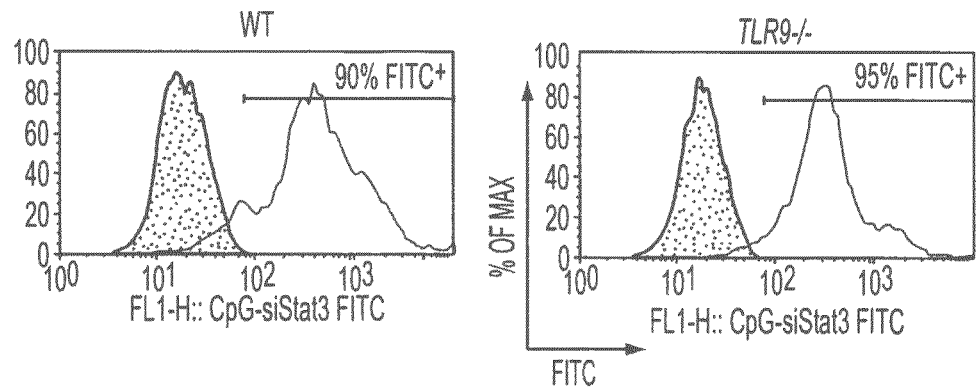
FIGS. 30a and 30b show that TLR9 is required for silencing effect of FITC-labeled CpG-Stat3 siRNA by myeloid cells.
Figure 30B:
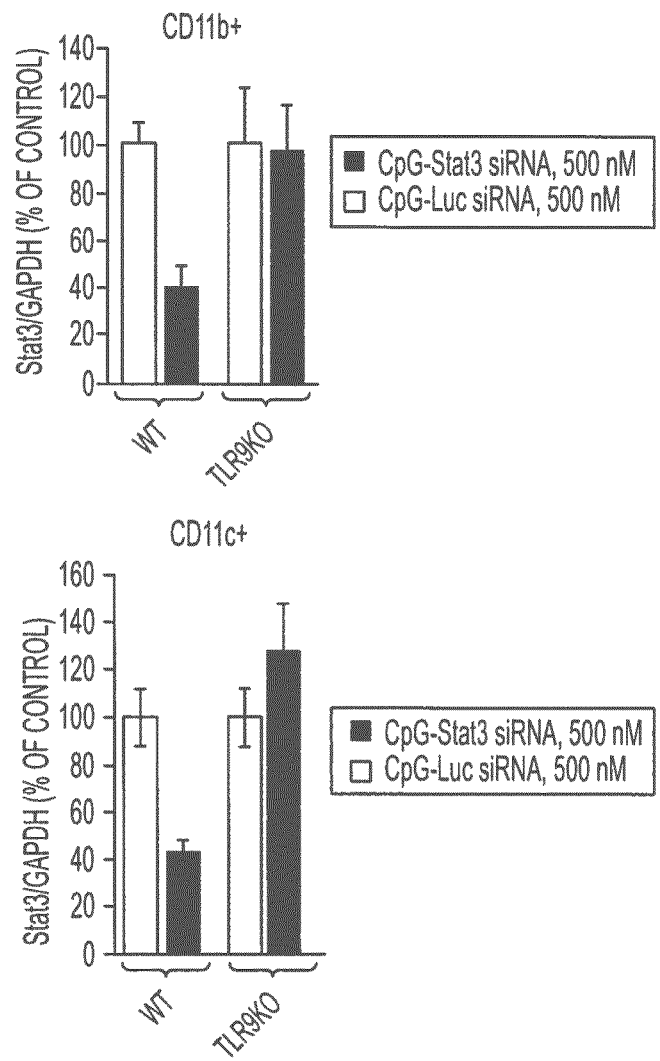

Additional results are shown in FIGS. 29a-29c for different siRNA Stat3 sequences. FIGS. 30a-30b also show that TLR9 is not necessary for uptake but is required for silencing effect of CpG-Stat3 siRNA by myeloid cells. FIGS. 31a-31e show that the CpG-siRNA approach effectively silences genes in $TLR9^+$ human tumor cells leading to therapeutic antitumor effects in animals. These results (i) show the validation of CpG-siRNA approach for cancer immunotherapy by using additional siRNAs with different sequences; (ii) show that TLR9 is not necessary for uptake but is required for silencing effect of CpG-Stat3 siRNA by myeloid cells and (iii) show that the CpG-siRNA approach effectively silences genes in $TLR9^+$ human tumor cells leading to therapeutic antitumor effects in animals.

We have developed a new strategy for targeted siRNA delivery together with immune activation by covalently linking TLR oligonucleotide agonists to siRNAs. These conjugates encompass three activities in a single molecule: targeting to immune cells, which include DCs, macrophages, and B cells, TLR activation and immune checkpoint silencing. In addition to TLR9, several other intracellular TLRs, such as TLR3, TLR7 and TLR8 also recognize nucleic acids, suggesting a broad application of this approach using various ligands for these TLRs to deliver various siRNAs into different immune cells. TLRs are important for stimulating dendritic cell maturation, antigen uptake and presentation, leading to CTL activation and $CD4^+$T helper cell differentiation. Therefore, TLR agonist-siRNA approaches can further stimulate desired immune responses for treating diseases such as cancer and infections. Although it has been established that binding to TLR9 is necessary for CpG-mediated immune activation, it remains to be fully explored how CpG ODN enter cells (Latz et al., 2004). Our results indicated that cellular uptake of both CpG ODN and the CpG-siRNA constructs can occur in the absence of TLR9. However, TLR9 is required for CpG-siRNA mediated gene silencing. While the exact underlying mechanism(s) remains to be determined, it is possible that triggering TLR9 could effect either endosomal release of CpG-siRNA into the cytoplasm, or/and its intracellular processing.

Although TLR9 is expressed in different types of mouse dendritic cells, its expression is more selective in humans. While the highest levels of constitutive TLR9 expression is observed on human plasmacytoid DCs and B cells, it is also expressed at lower levels on human monocytes and macrophages (Iwasaki and Medzihitov, 2004). These immune cells can serve as antigen-presenting cells and induce innate, adaptive or humoral immunity (Kanzler et al., 2007; Krieg, 2008; Marshner et al., 2005; Klinman et al., 2008). Furthermore, it has been demonstrated recently that adding triphosphate to the 5' of siRNA can greatly potentiate the antitumor effects of siRNA by stimulating antitumor immune responses, likely through intracellular RNA sensors such as RIG-I or MDA-5 (Poeck et al., 2008). It is therefore conceivable to incorporate triphosphate to the CpG-siRNA to further amplify antitumor immunity. In addition, a critical role of tumor stromal macrophages and B cells in promoting tumor development has been well documented (Pollard, 2004; Sica and Bronte, 2007; Tan and Coussens, 2007). Importantly, Stat3 and several other molecules produced by the tumor myeloid population, and possibly tumor-associated B cells, are critical for tumor immunosuppression (Yu et al., 2007), and Stat3 activity in the myeloid compartment (possibly B cells as well) promotes Stat3 activity in tumor cells and endothelial cells in the tumor, enhancing tumor cell growth/survival (Kujawski et al., 2008; Bollrath et al., 2009; Grivennikov et al., 2009; Lee et al., 2009). In addition to Stat3, other oncogenic molecules produced by the tumor myeloid/B cell compartment are also critical in promoting cancer growth and resistance to various therapies. Therefore, being able to target the tumor stromal myeloid cells/B cells through CpG-siRNA conjugate molecules is highly desirable for cancer therapies. In addition to normal immune cells, several types of tumor cells, including those of B cell origin, and some solid tumor cells, are also positive for TLR9 (Jahrsdorfer et al., 2005; Spaner et al., 2008). Our preliminary results suggested the feasibility of CpG-siRNA approach to silence genes in $TLR9^+$ tumor cells. For example, treating human $TLR9^+$ tumors in NOD/SCID/IL-2RγKO mice with CpG-Stat3 siRNA resulted in tumor cell apoptosis and tumor growth inhibition (Kortylewski and Yu, unpublished data).

Our results indicated that the gene silencing effects by CpG-siRNA in cultured cells requires high concentrations of the conjugates and are suboptimal relative to in vivo treatment. Work is underway to determine the possible cause(s) of this difference, which might include serum-dependent degradation of CpG-siRNAs or reduction of the overall silencing effect in rapidly dividing cell populations. It is possible that in vivo repeated treatments allow accumulative gene silencing effects, and the crosstalk between various cells in the tumor microenvironment could lead to secondary effects on Stat3 activity (Lee et al., 2009). The half-life of the constructs at present is limited. Although the CpG ODN in the construct is phosphorothioated, which should resist serum degradation, the siRNA in the chimeric construct is unmodified and negatively charged. Chemically modifying the siRNA to prolong serum stability and to neutralize the negative charge of the siRNA to facilitate endosomal release may improve the efficacy of TLR agonist-siRNA approach. Our results show the use of oligonucleotide TLR agonists for siRNA delivery into tumor-associated myeloid cells and B cells to inhibit expression of tumor-promoting/immunosuppressive molecules while activating TLR(s) for immune activation.

The proof-of-principle experiments provided evidence that systemically delivered CpG(A)-STAT3 siRNA (i.e., CpG (D19)-STAT3 siRNA) can target human TLR9+ cells in vivo. The intravenously injected CpG(A)-STAT3 siRNA led to STAT3 gene silencing in human MV4-11 acute myeloid leukemia (AML) cells residing in the bone-marrow of immunodeficient NOD/SCID/IL-2Rγ$^{null}$ (NSG) mice (FIG. 32a). In other preliminary studies, effects of CpG(A)-siRNAs targeting oncogenic and/or prosurvival genes injected intratumorally into KMS-11 multiple myeloma (MM) (FIG. 32b) or MonoMac6 and MV4-11 AML (FIG. 32c and FIG. 32d) tumors growing s.c. in NSG mice were compared. The repeated local administration of CpG(A)-siRNAs specific for either STAT3 or BCL $X_L$ genes resulted in gene-specific silencing, induced tumor cell death and reduced growth of xenotransplanted tumors (FIGS. 32b-32d).

Figure 33:
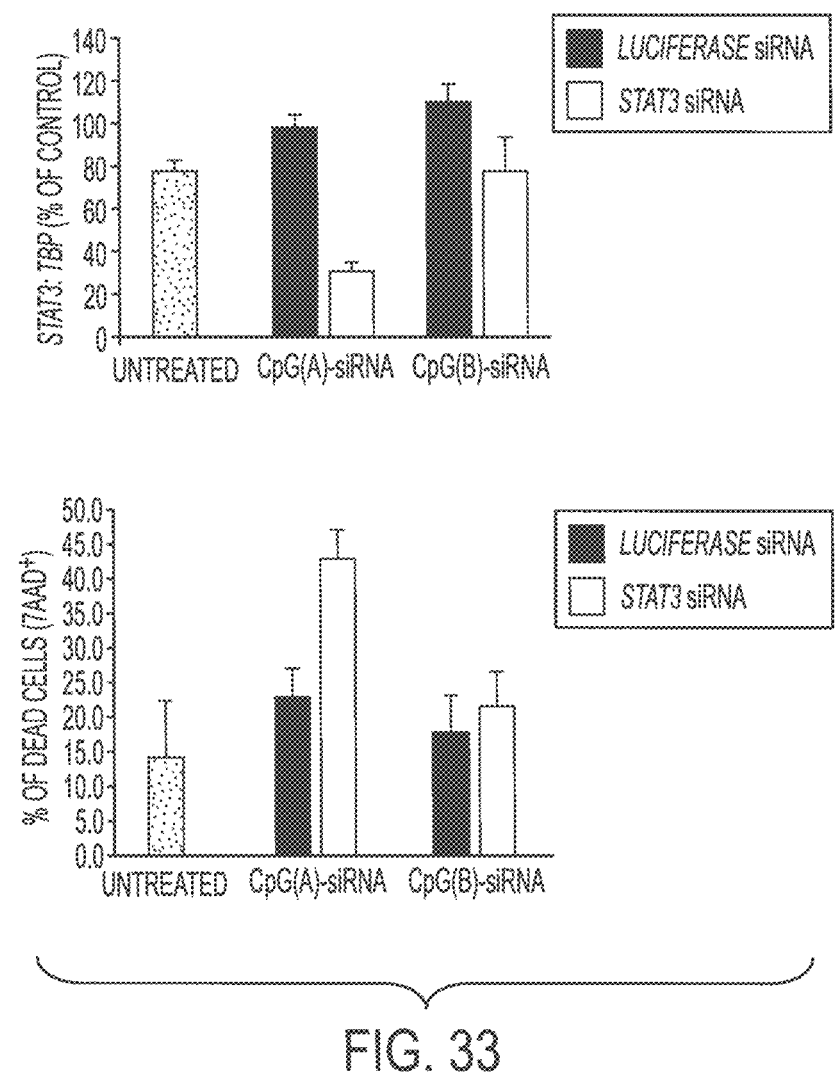
FIG. 33 shows the efficacy of in vivo target gene silencing by CpG-STAT3 siRNA depends on the CpG ODN sequence.

In preliminary studies, the silencing efficacy of CpG-siRNA conjugates based on CpG oligodeoxynucleotides from either class A or class B were also compared. As shown in FIG. 33 (top) and 33 (bottom), class A-based CpG(D19)-STAT3 siRNA induced more pronounced target gene silencing effect (FIG. 33 (*top*)) and higher degree of tumor cell death (FIG. 33 (bottom)) that than the class B-based CpG (7909)-STAT3 siRNA in comparison to matching control class A and class B CpG-Luciferase siRNAs, respectively. Sequences of single stranded constructs not disclosed above are listed below.

CpG(7909)-human STAT3 siRNA (antisense strand; underlined are deoxyribonucleotides, asterisks indicate phosphothioated sites, X indicates single C3 carbon chain linker)

(SEQ ID NO: 21-XXXXX-SEQ ID NO: 5)
5' T*C*G*T*C*G*T*T*T*T*G*T*C*G*T*T*T*T*G*T*C*G*T*T-XXXXX-UCAGUCGUA

UCUUUCUGCAGCUUCCGU 3'

CpG(7909)-Luciferase siRNA (antisense strand; underlined are deoxyribonucleotides, asterisks indicate phosphothioated sites, X indicates single C3 carbon chain linker)

(SEQ ID NO: 21-XXXXX-SEQ ID NO: 22)
5' T*C*G*T*C*G*T*T*T*T*G*T*C*G*T*T*T*T*G*T*C*G*T*T-XXXXX-UGUAAAAG

CAAUUGUUCCAGGAACCAG 3'

Luciferase siRNA (sense strand; underlined are deoxyribonucleotides)

(SEQ ID NO: 23)
5' GGUUCCUGGAACAAUUGCUUUUAC<u>A</u> 3'

Figure 34:
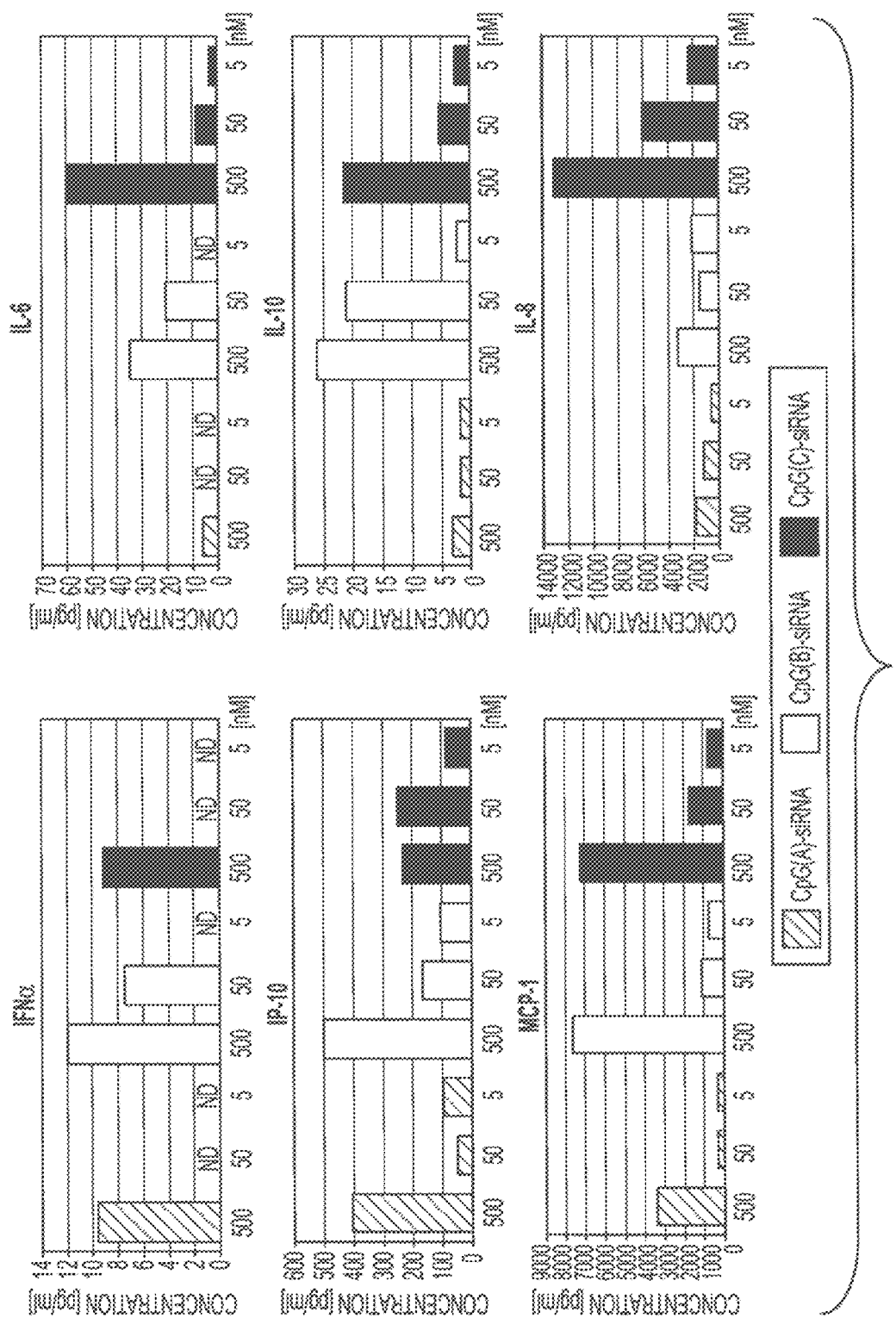
FIG. 34 shows that the class A ODN-based CpG(D19)-STAT3 siRNA conjugates induce production of proinflammatory protein mediators without stimulating expression of potentially tumor promoting IL-6, IL-8 or IL-10, which are co-activated by two other CpG-siRNA types. Human PBMCs were incubated for 24 h in the presence of class A—CpG (D19)-STAT3 siRNA, calls B—CpG(7909)-STAT3 siRNA or class C—CpG(2429)-STAT3 siRNA conjugates in concentrations as indicated. Supernatants from cultured PBMCs were analyzed for the production of pro-inflammatory and anti-inflammatory protein mediators using Cytokine Bead Arrays on Luminex platform. Shown are representative results from one of two independent experiment performed in triplicates; ND—not detectable.
Figure 35:
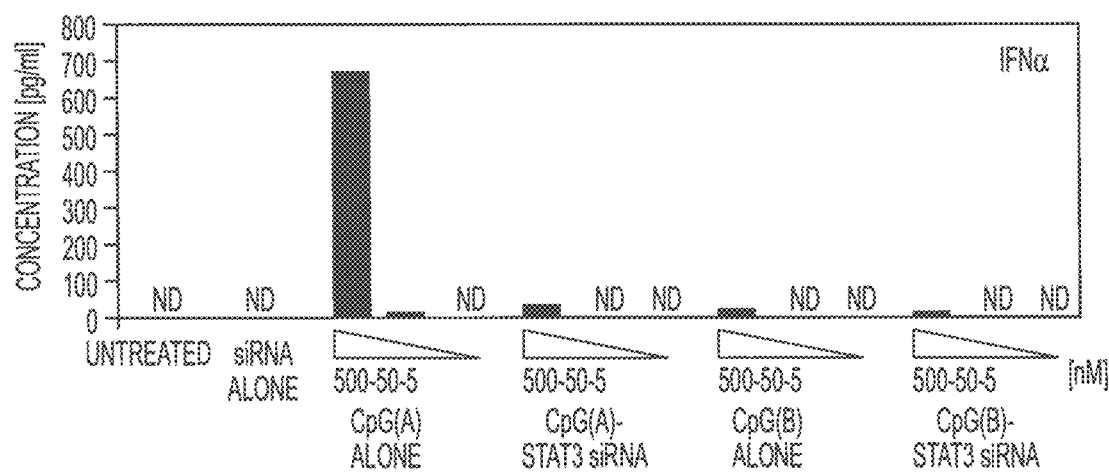
FIG. 35 shows that the CpG(D19)-STAT3 siRNA does not induce exacerbated type I interferon response, in contrast to unconjugated D19 class A oligodeoxynocleotides. Human PBMCs were incubated for 24 h in the presence of STAT3 siRNA, CpG(A)-D19, CpG(B)-7909 alone or as CpG-STAT3 siRNA conjugates in concentrations as indicated. Supernatants from cultured PBMCs were analyzed for the IFNα production using Cytokine Bead Array on Luminex platform. Shown are representative results from one of two independent experiment performed in triplicates; ND—not detectable.

To assess the potential safety of CpG-siRNAs for normal human immune cells, cultured human peripheral blood mononuclear cells (PBMCs) were used. Multiplex assays indicated that CpG(D19)-STAT3 siRNA induced more desirable cytokine expression profile comparing to the class B-based CpG(7909)-STAT3 siRNA and class C-based CpG (2429)-STAT3 siRNA (FIG. 34). Although inflammatory cytokines/chemokines, such as IFNα, IP-10, MCP-1, were induced at similar levels by all three conjugates, both CpG (7909)- and CpG(2429)-STAT3 siRNAs also led to production of potentially tumorigenic/tolerogenic IL-6 and IL-10 that could dampen the overall immunostimulatory effect. Importantly, the in vitro studies on human PBMCs demonstrated that CpG(A)-STAT3 siRNA was immunostimulatory but not immunotoxic for normal immune cells. The siRNA conjugation to CpG(D19) eliminated the exacerbated interferon type I responses typical for class A of CpG ODNs (FIG. 35), which hindered their clinical application. Sequences of single stranded constructs not disclosed above are listed below.

CpG(2429)-human STAT3 siRNA (antisense strand; underlined are deoxyribonucleotides, asterisks indicate phosphothioated sites, X indicates single C3 carbon chain linker)

(SEQ ID NO: 24-XXXXX-SEQ ID NO: 5)
5' T*C*G*T*C*G*T*T*T*T*C*G*G*C*G*G*C*C*G*C*C*G-XXXXX-UCAGUCGUAUC

UUUCUGCAGCUUCCGU 3'

CpG(2429)-Luciferase siRNA (antisense strand; underlined are deoxyribonucleotides, asterisks indicate phosphothioated sites, X indicates single C3 carbon chain linker)

(SEQ ID NO: 24-XXXXX-SEQ ID NO: 22)
5' T*C*G*T*C*G*T*T*T*T*C*G*G*C*G*G*C*C*G*C*C*G-XXXXX-GUAAAAGCAAU

UGUUCCAGGAACCAG 3'

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Alexopoulou, L. et al. (2001). Recognition of double-stranded RNA and activation of NK-κB by toll0like receptor 3. *Nature* 413:732-738.

Alonzi, T. et al. (2004). Induced somatic inactivation of STAT3 in mice triggers the development of a fulminant form of enterocolitis. *Cytokine* 26:45-56.

Barchet, W. et al. (2008). Accessing the therapeutic potential of immunostimulatory nucleic acids. *Curr Opin Immunol* 20:389-395.

Benkhart, E. M. et al (2000). Role of Stat3 in lipopolysaccharide-induced IL-10 gene expression. *J Immunol* 165:1612-1617.

Bollrath, J. et al. (2009). gp130-mediated Stat3 activation in enterocytes regulates cell survival and cell-cycle progression during colitis-associated tumorigenesis. *Cancer Cell* 15:91-102.

Bourke, E. et al. (2003). The toll-like receptor repertoire of human B lymphocytes: inducible and selective expression of TLR9 and TLR10 in normal and transformed cells. *Blood* 102:956-963.

Bromberg, J. F. et al. (1999). Stat3 as an oncogene. *Cell* 98:295-303.

Bui, J. D. and Schreiber, R. D. (2007). Cancer immunosurveillance, immunoediting and inflammation: independent or interdependent processes? *Curr Opin Immunol* 19:203-208.

Bui, J. D. et al. (2006). Comparative analysis of regulatory and effector T cells in progressively growing versus rejecting tumors of similar origins. *Cancer Res* 66:7301-7309.

Cao, Y. A. et al. (2004). Shifting foci of hematopoiesis during reconstitution from single stem cells. *Proc Natl Acad Sci USA* 101:221-226.

Chendrimada, T. P. et al. (2005). TRBP recruits the Dicer complex to Ago2 for microRNA processing and gene silencing. *Nature* 436:740-744.

Curiel, T. J. et al. (2004). Specific recruitment of regulatory T cells in ovarian carcinoma fosters immune privilege and predicts reduced survival. *Nat Med* 10:942-949.

Darnell, J. E., Jr. (2002). Transcription factors as targets for cancer therapy. *Nat Rev Cancer* 2:740-749.

Dhodapkar, M. V. et al. (2001). Antigen-specific inhibition of effector T cell function in humans after injection of immature dendritic cells. *J Exp Med* 193:233-238.

Dhodapkar, M. V. et al. (2008). Interactions of tumor cells with dendritic cells: balancing immunity and tolerance. *Cell Death Differ* 15:39-50.

Eckstein, F. (2000). Phosphorothioate oligodeoxynucleotides: what is their origin and what is unique about them? *Antisense Nucleic Acid Drug Dev* 10:117-21.

Ellington, A. D. and Szostak, J. W. (1990). In vitro selection of RNA molecules that bind specific ligands. *Nature* 346:818-822.

Ghiringhelli, F. et al. (2005). Tumor cells convert immature myeloid dendritic cells into TGF-beta-secreting cells inducing CD4+CD25+ regulatory T cell proliferation. *J Exp Med* 202:919-929.

Grivennikov, S. et al. (2009). IL-6 and Stat3 are required for survival of intestinal epithelial cells and development of colitis-associated cancer. *Cancer Cell* 15:103-113.

Haase, A. D. et al. (2005). TRBP, a regulator of cellular PKR and HIV-1 virus expression, interacts with Dicer and functions in RNA silencing. *EMBO Rep* 6:961-967.

Hemmi, H. et al. (2000). A Toll-like receptor recognizes bacterial DNA. *Nature* 408:740-745.

Herdewijn, P. (2000). Heterocyclic modifications of oligonucleotides and antisense technology. *Antisense Nucleic Acid Drug Dev* 10:297-310.

Hu-Lieskovan, S. et al. (2005). Sequence-specific knockdown of EWS-FLI1 by targeted, nonviral delivery of small interfering RNA inhibits tumor growth in a murine model of metastatic Ewing's sarcoma. *Cancer Res* 65:8984-8992.

Iwasaki, A. and Medzhitov, R. (2004). Toll-like receptor control of the adaptive immune responses. *Nat Immunol* 5:987-995.

Jahrsdorfer, B. et al. (2005). B-cell lymphomas differ in their responsiveness to CpG oligodeoxynucleotides. *Clin Cancer Res* 11:1490-1499.

Janowski, B. A. et al. (2007). Activating gene expression in mammalian cells with promoter-targeted duplex RNAs. *Nat Chemical Biol* 3:166-173.

Kanzler, H. et al. (2007). Therapeutic targeting of innate immunity with Toll-like receptor agonists and antagonists. *Nat Med* 13:552-559.

Kim, D. H. et al. (2005). Synthetic dsRNA Dicer substrates enhance RNAi potency and efficacy. *Nat Biotechnol* 23:222-226.

Kirkwood, J. M et al. (1999). Systemic interferon-alpha (IFN-alpha) treatment leads to Stat3 inactivation in melanoma precursor lesions. *Mol Med* 5:11-20.

Klinman, D. M. et al. (1996). CpG motifs present in bacteria DNA rapidly induce lymphocytes to secrete interleukin 6, interleukin 12, and interferon gamma. *Proc Natl Acad Sci USA* 93:2879-2883.

Klinman, D. M.et al. (2004). Use of CpG oligodeoxynucleotides as immune adjuvants. *Immunol Rev* 199:201-216.

Klinman, D. et al. (2008). Synthetic oligonucleotides as modulators of inflammation. *J Leukoc Biol* 84:958-964.

Kobayashi, M. et al. (2003). Toll-like receptor-dependent production of IL-12p40 causes chronic enterocolitis in myeloid cell-specific Stat3-deficient mice. *J Clin Invest* 111:1297-308.

Koebel, C. M. et al. (2007). Adaptive immunity maintains occult cancer in an equilibrium state. *Nature* 450:903-907.

Kortylewski, M. and Yu, H. Role of Stat3 in suppressing anti-tumor immunity. *Curr Opin Immunol* 20:228-233.

Kortylewski, M. et al. (2005a). Targeting STAT3 affects melanoma on multiple fronts. *Cancer Metastasis Rev* 24:315-327.

Kortylewski, M. et al. (2005b). Inhibiting Stat3 signaling in the hematopoietic system elicits multicomponent antitumor immunity. *Nat Med* 12:1314-1321.

Kortylewski, M. et al. (2009a). Regulation of the IL-23 and IL-12 balance by Stat3 signaling in the tumor microenvironment. *Cancer Cell* 15:114-123.

Kortylewski, M. et al. (2009b). Toll-like receptor 9 activation of signal transducer and activator of transcription 3 constrains its agonist-based immunotherapy. *Cancer Res* 69:2497-2505.

Krieg, A. M. (2008). Toll-like receptor 9 (TLR9) agonists in the treatment of cancer. *Oncogene* 27:161-167.

Krieg, A. M. et al. (1995). CpG motifs in bacterial DNA trigger direct B-cell activation. *Nature* 374:546-549.

Kuhn, R. et al. (1995). Inducible gene targeting in mice. *Science* 269:1427-1429.

Kujawski, M. et al. (2008). Stat3 mediates myeloid cell-dependent tumor angiogenesis in mice. *J Clin Invest* 118:3367-3377.

Kumar, P. et al. (2007). Transvascular delivery of small interfering RNA to the central nervous system. *Nature* 448:39-43.

Kuwabara, T. et al. (2005). The NRSE smRNA specifies the fate of adult hippocampal neural stem cells. *Nucleic Acids Symp Series* 49:87-88.

Latz, E. et al. (2004). TLR9 signals after translocating from the ER to CpG DNA in the lysosome. *Nat Immunol* 5:190-198.

Lee, C. K. et al. (2002). STAT3 is a negative regulator of granulopoiesis but is not required for G-CSF-dependent differentiation. *Immunity* 17:63-72.

Lee, H. et al. (2009). Persistently activated Stat3 maintains constitutive NF-kappaB activity in tumors. *Cancer Cell* 15:283-293.

Li, B. J. et al. (2005). Using siRNA in prophylactic and therapeutic regimens against SARS coronavirus in Rhesus macaque. *Nat Med* 11:944-951.

Li, L. et al. (2006). Small dsRNAs induce transcriptional activation in human cells. *Proc Natl Acad Sci USA* 103:17337-17342.

Marschner, A. et al. (2005). CpG ODN enhance antigen-specific NKT cell activation via plasmacytoid dendritic cells. *Eur J Immunol* 35:2347-2357.

McNamara, J. O., 2nd et al. (2006). Cell type-specific delivery of siRNAs with aptamer-siRNA chimeras. *Nat Biotechnol* 24:1005-1015.

McNamara, J. O. et al. (2008). Multivalent 4-1BB binding aptamers costimulate CD8+T cells and inhibit tumor growth in mice. *J Clin Invest* 118:376-386.

Melani, C. et al. (2003). Myeloid cell expansion elicited by the progression of spontaneous mammary carcinomas in c-erbB-2 transgenic BALB/c mice suppresses immune reactivity. *Blood* 102:2138-2145.

Peng, G. et al. (2005). Toll-like receptor 8-mediated reversal of $CD4^+$ regulatory T cell function. *Science* 309:1380-1384.

Poeck, H. et al. (2008). 5'-Triphosphate-siRNA: turning gene silencing and Rig-I activation against melanoma. *Nat Med* 14:1256-1263).

Pollard, J. W. (2004). Tumour-educated macrophages promote tumour progression and metastasis. *Nat Rev Cancer* 4:71-78.

Reid, G. S. et al. (2005). CpG stimulation of precursor B-lineage acute lymphoblastic leukemia induces a distinct change in costimulatory molecule expression and shifts allogeneic T cells toward a Th1 response. *Blood* 105:3641-3647.

Rose, S. D. et al. (2005). Functional polarity is introduced by Dicer processing of short substrate RNAs. *Nucleic Acids Res* 33:4140-4156.

Rusckowski, M. et al. (2000). Biodistribution and metabolism of a mixed backbone oligonucleotide (GEM 231) following single and multiple dose administration in mice. *Antisense Nucleic Acid Drug Dev* 10:333-345.

Samarasinghe, R. et al. (2006). Induction of an anti-inflammatory cytokine, IL-10, in dendritic cells after toll-like receptor signaling. *J Interferon Cytokine Res* 26:893-900.

Seela, F. and Kaiser, K. (1987). Oligodeoxyribonucleotides containing 1,3-propanediol as nucleoside substitute. *Nucl Acids Res* 15:3113-3129.

Shankaran, V. et al. (2001). IFNgamma and lymphocytes prevent primary tumour development and shape tumour immunogenicity. *Nature* 410:1107-1111.

Sica, A. and Bronte, V. (2007). Altered macrophage differentiation and immune dysfunction in tumor development. *J Clin Invest* 117:1155-1166.

Song, E. et al. (2005). Antibody mediated in vivo delivery of small interfering RNAs via cell-surface receptors. *Nat Biotechnol* 23:709-717.

Spaner, D. E. et al. (2008). Obstacles to effective Toll-like receptor agonist therapy for hematologic malignancies. *Oncogene* 27:208-217.

Stein, D. A. et al. (2001) Inhibition of Vesivirus infections in mammalian tissue culture with antisense morpholino oligomers. *Antisense Nucleic Acid Drug Dev* 11:317-25.

Sumimoto, H. et al. (2006). The BRAF-MAPK signaling pathway is essential for cancer-immune evasion in human melanoma cells. *J Exp Med* 203:1651-1656.

Swiderski, P. M. et al. (1994). Polystyrene reverse-phase ion-pair chromatography of chimeric ribozymes. *Analytical Biochemistry* 216:83-886.

Takeda, K. et al. (1999). Enhanced Th1 activity and development of chronic enterocolitis in mice devoid of Stat3 in macrophages and neutrophils. *Immunity* 10:39-49.

Tan, T. T. and Coussens, L. M. (2007). Humoral immunity, inflammation and cancer. *Curr Opin Immunol* 19:209-216.

Tuerk, C. and Gold, L. (1990). Systematic evolution of ligands by exponential enrichment: RNA ligands to bacteriophage T4 DNA polymerase. *Science* 249:505-510.

Verma, S. And Eckstein, F. (1998). Modified oligonucleotides: synthesis and strategy for users. *Annu Rev Biochem* 67:99-134.

Vicari, A. P. et al. (2002). Tumour escape from immune surveillance through dendritic cell inactivation. *Semin Cancer Biol* 12; 33-42.

Vorobjev, P. E. et al. (2001). Nuclease resistance and RNase H sensitivity of oligonucleotides bridged by oligomethylenediol and oligoethylene glycol linkers. *Antisense Nucleic Acid Drug Dev* 11:77-85.

Wang, L. et al. (2009). IL-17 is pro-carcinogenic through an IL-6/Stat3 signaling pathway. *J. Exp. Med.* 206:1457-1464.

Wang, T. et al. (2004). Regulation of the innate and adaptive immune responses by Stat-3 signaling in tumor cells. *Nat Med* 10:48-54.

Welte, T. et al. (2003). STAT3 deletion during hematopoiesis causes Crohn's disease-like pathogenesis and lethality: a critical role of STAT3 in innate immunity. *Proc Natl Acad Sci USA* 100:1879-84.

Xie, T. X. et al. (2004). Stat3 activation regulates the expression of matrix metalloproteinase-2 and tumor invasion and metastasis. *Oncogene* 23:3550-3560.

Xie, T. X. et al. (2006). Activation of stat3 in human melanoma promotes brain metastasis. *Cancer Res* 66:3188-3196.

Yu, C. L. et al. (1995). Enhanced DNA-binding activity of a Stat3-related protein in cells transformed by the Src oncoprotein. *Science* 269:81-83.

Yu, H. and Jove, R. (2004). The STATs of cancer—new molecular targets come of age. *Nat Rev Cancer* 4:97-105.

Yu, H. et al. (2007). Crosstalk between cancer and immune cells: role of STAT3 in the tumour microenvironment. *Nat Rev Immunol* 7:41-51.

Yu, P. et al. (2005). Intratumor depletion of CD4+ cells unmasks tumor immunogenicity leading to the rejection of late-stage tumors. *J Exp Med* 201:779-791.

Zimmermann, T. S. et al. (2006). RNAi-mediated gene silencing in non-human primates. *Nature* 441:111-114.

Zou, W. (2005) Immunosuppressive networks in the tumour environment and their therapeutic relevance. *Nat Rev Cancer* 5:263-274.

---

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial
<220> FEATURE:
<223> OTHER INFORMATION: Toll-like receptor ligand oligonucleotide

<400> SEQUENCE: 1
tccatgacgt tcctgatgct                                                 20

<210> SEQ ID NO 2
<211> LENGTH: 27
<212> TYPE: RNA
<213> ORGANISM: Artificial
<220> FEATURE:
<223> OTHER INFORMATION: siRNA oligonucleotide antisense strand

<400> SEQUENCE: 2
uuagcccaug ugaucugaca cccugaa                                         27

<210> SEQ ID NO 3
<211> LENGTH: 25
<212> TYPE: DNA
<213> ORGANISM: Artificial
<220> FEATURE:
<223> OTHER INFORMATION: siRNA oligonucleotide sense strand
<220> FEATURE:
<221> NAME/KEY: misc_feature
<222> LOCATION: (1)..(23)
<223> OTHER INFORMATION: RNA bases

<400> SEQUENCE: 3
caggguguca gaucacaugg gcuaa                                           25

<210> SEQ ID NO 4
<211> LENGTH: 25
<212> TYPE: DNA
<213> ORGANISM: Artificial
<220> FEATURE:
```

```
<223> OTHER INFORMATION: siRNA oligonucleotide sense strand
<220> FEATURE:
<221> NAME/KEY: misc_feature
<222> LOCATION: (1)..(23)
<223> OTHER INFORMATION: RNA bases

<400> SEQUENCE: 4
ggaagcugca gaaagauacg acuga                                            25

<210> SEQ ID NO 5
<211> LENGTH: 27
<212> TYPE: RNA
<213> ORGANISM: Artificial
<220> FEATURE:
<223> OTHER INFORMATION: siRNA oligonucleotide antisense strand

<400> SEQUENCE: 5
ucagucguau cuuucugcag cuuccgu                                          27

<210> SEQ ID NO 6
<211> LENGTH: 20
<212> TYPE: DNA
<213> ORGANISM: Artificial
<220> FEATURE:
<223> OTHER INFORMATION: Control oligonucleotide

<400> SEQUENCE: 6
tccatgagct tcctgatgct                                                  20

<210> SEQ ID NO 7
<211> LENGTH: 20
<212> TYPE: DNA
<213> ORGANISM: Artificial
<220> FEATURE:
<223> OTHER INFORMATION: Toll-like receptor ligand oligonucleotide

<400> SEQUENCE: 7
ggtgcatcga tgcagggggg                                                  20

<210> SEQ ID NO 8
<211> LENGTH: 25
<212> TYPE: DNA
<213> ORGANISM: Artificial
<220> FEATURE:
<223> OTHER INFORMATION: Scrambled RNA oligonucleotide sense strand
<220> FEATURE:
<221> NAME/KEY: misc_feature
<222> LOCATION: (1)..(23)
<223> OTHER INFORMATION: RNA bases

<400> SEQUENCE: 8
uccaaguaga uucgacggcg aagtg                                            25

<210> SEQ ID NO 9
<211> LENGTH: 27
<212> TYPE: RNA
<213> ORGANISM: Artificial
<220> FEATURE:
<223> OTHER INFORMATION: Scrambled RNA oligonucleotide antisense strand

<400> SEQUENCE: 9
cacuucgccg ucgaaucuac uuggauu                                          27

<210> SEQ ID NO 10
<211> LENGTH: 23
<212> TYPE: DNA
<213> ORGANISM: Artificial
```

```
<220> FEATURE:
<223> OTHER INFORMATION: Activating RNA oligonucleotide sense strand
<220> FEATURE:
<221> NAME/KEY: misc_feature
<222> LOCATION: (1)..(21)
<223> OTHER INFORMATION: RNA bases

<400> SEQUENCE: 10
uguccucugu ccucuaagau utt                                           23

<210> SEQ ID NO 11
<211> LENGTH: 23
<212> TYPE: DNA
<213> ORGANISM: Artificial
<220> FEATURE:
<223> OTHER INFORMATION: Activating RNA oligonucleotide antisense strand
<220> FEATURE:
<221> NAME/KEY: misc_feature
<222> LOCATION: (1)..(21)
<223> OTHER INFORMATION: RNA bases

<400> SEQUENCE: 11
aaucuuagag gacagaggac att                                           23

<210> SEQ ID NO 12
<211> LENGTH: 25
<212> TYPE: DNA
<213> ORGANISM: Artificial Sequence
<220> FEATURE:
<223> OTHER INFORMATION: siRNA oligonucleotide sense strand
<220> FEATURE:
<221> NAME/KEY: misc_feature
<222> LOCATION: (1)..(23)
<223> OTHER INFORMATION: RNA bases

<400> SEQUENCE: 12
gugacaccaa cgaccugcag caata                                         25

<210> SEQ ID NO 13
<211> LENGTH: 27
<212> TYPE: RNA
<213> ORGANISM: Artificial Sequence
<220> FEATURE:
<223> OTHER INFORMATION: siRNA oligonucleotide antisense strand

<400> SEQUENCE: 13
uauugcugca ggucguuggu gucacac                                       27

<210> SEQ ID NO 14
<211> LENGTH: 25
<212> TYPE: DNA
<213> ORGANISM: Artificial Sequence
<220> FEATURE:
<223> OTHER INFORMATION: siRNA oligonucleotide sense strand
<220> FEATURE:
<221> NAME/KEY: misc_feature
<222> LOCATION: (1)..(23)
<223> OTHER INFORMATION: RNA bases

<400> SEQUENCE: 14
gucugaaacu ccuaacuuug uggtt                                         25

<210> SEQ ID NO 15
<211> LENGTH: 27
<212> TYPE: RNA
<213> ORGANISM: Artificial Sequence
<220> FEATURE:
<223> OTHER INFORMATION: siRNA oligonucleotide antisense strand
```

```
<400> SEQUENCE: 15
aaccacaaag uuaggaguuu cagacga                                               27

<210> SEQ ID NO 16
<211> LENGTH: 20
<212> TYPE: DNA
<213> ORGANISM: Artificial Sequence
<220> FEATURE:
<223> OTHER INFORMATION: Toll-like receptor ligand oligonucleotide
<220> FEATURE:
<221> NAME/KEY: misc_feature
<222> LOCATION: (1)..(20)
<223> OTHER INFORMATION: phosphorothioated linkage between nucleotides 1
      and 2, 16 and 17, 17 and 18, 18 and 19, and 19 and 20

<400> SEQUENCE: 16
ggtgcatcga tgcagggggg                                                       20

<210> SEQ ID NO 17
<211> LENGTH: 25
<212> TYPE: DNA
<213> ORGANISM: Artificial Sequence
<220> FEATURE:
<223> OTHER INFORMATION: siRNA oligonucleotide sense strand
<220> FEATURE:
<221> NAME/KEY: misc_feature
<222> LOCATION: (1)..(23)
<223> OTHER INFORMATION: RNA bases
<220> FEATURE:
<221> NAME/KEY: misc_feature
<222> LOCATION: (1)..(23)
<223> OTHER INFORMATION: bases at positions 3, 4, 7, 9, 10, 12-14, 16-19
      and 23 are modified

<400> SEQUENCE: 17
ggaagcugca gaaagauacg acuga                                                 25

<210> SEQ ID NO 18
<211> LENGTH: 25
<212> TYPE: RNA
<213> ORGANISM: Artificial Sequence
<220> FEATURE:
<223> OTHER INFORMATION: siRNA oligonucleotide sense strand

<400> SEQUENCE: 18
ggaagcugca gaaagauacg acuga                                                 25

<210> SEQ ID NO 19
<211> LENGTH: 16
<212> TYPE: RNA
<213> ORGANISM: Artificial Sequence
<220> FEATURE:
<223> OTHER INFORMATION: oligonucleotide overhang
<220> FEATURE:
<221> NAME/KEY: misc_feature
<222> LOCATION: (1)..(16)
<223> OTHER INFORMATION: bases at positions 2, 4, 7, 8, and 11-15 are
      modified

<400> SEQUENCE: 19
acguggccga cuuccu                                                           16

<210> SEQ ID NO 20
<211> LENGTH: 16
<212> TYPE: RNA
<213> ORGANISM: Artificial Sequence
<220> FEATURE:
<223> OTHER INFORMATION: oligonucleotide overhang
<220> FEATURE:
```

```
<221> NAME/KEY: misc_feature
<223> OTHER INFORMATION: bases at positions 7, 8, 11, 12, 14 and 15 are
      modified

<400> SEQUENCE: 20
aggaagucgg ccacgu                                                     16

<210> SEQ ID NO 21
<211> LENGTH: 24
<212> TYPE: DNA
<213> ORGANISM: Artificial Sequence
<220> FEATURE:
<223> OTHER INFORMATION: Toll-like receptor ligand oligonucleotide
<220> FEATURE:
<221> NAME/KEY: misc_feature
<222> LOCATION: (1)..(24)
<223> OTHER INFORMATION: phosphorothioated linkage between each of
      nucleotides 1-24

<400> SEQUENCE: 21
tcgtcgtttt gtcgttttgt cgtt                                            24

<210> SEQ ID NO 22
<211> LENGTH: 27
<212> TYPE: RNA
<213> ORGANISM: Artificial Sequence
<220> FEATURE:
<223> OTHER INFORMATION: siRNA oligonucleotide antisense strand

<400> SEQUENCE: 22
uguaaaagca auguuccag gaaccag                                          27

<210> SEQ ID NO 23
<211> LENGTH: 25
<212> TYPE: DNA
<213> ORGANISM: Artificial Sequence
<220> FEATURE:
<223> OTHER INFORMATION: siRNA oligonucleotide sense strand
<220> FEATURE:
<221> NAME/KEY: misc_feature
<222> LOCATION: (1)..(23)
<223> OTHER INFORMATION: RNA bases

<400> SEQUENCE: 23
gguuccugga acaauugcuu uuaca                                           25

<210> SEQ ID NO 24
<211> LENGTH: 22
<212> TYPE: DNA
<213> ORGANISM: Artificial Sequence
<220> FEATURE:
<223> OTHER INFORMATION: Toll-like receptor ligand oligonucleotide
<220> FEATURE:
<221> NAME/KEY: misc_feature
<222> LOCATION: (1)..(22)
<223> OTHER INFORMATION: phosphorothioated linkage between each of
      nucleotides 1-22

<400> SEQUENCE: 24
tcgtcgtttt cggcggccgc cg                                              22
```

What is claimed is:

1. A method of treating a disease which comprises administering a therapeutically effective amount of a molecule to an individual in need thereof, wherein the disease is one that can be treated by regulating the Stat3 pathway or genes under control of Stat3, wherein the molecule comprises a modified human STAT3 sense strand and a human CpG(D19)-STAT3 antisense strand, wherein the modified human STAT3 sense strand comprises an oligonucleotide having the nucleotides set forth in SEQ ID NO:17, wherein the modifications are selected from the group consisting of 2'F, 2'OMe, LNA, nucleotides and other modifications described herein, wherein the human CpG(D19)-STAT3 antisense strand comprises (a) a first oligonucleotide having the nucleotides set forth in SEQ ID NO:16, (b) a C3 carbon chain or propanediol linker and (c) a second oligonucleotide having the nucleotides set forth in SEQ ID NO:5 that is the antisense strand, and wherein the sense strand and the antisense strand anneal to form a double stranded siRNA.

2. The method of claim 1, wherein the disease is selected from the group consisting of cancer, an infectious disease and an autoimmune disease.

3. A method of treating a disease which comprises administering a therapeutically effective amount of a molecule to an individual in need thereof, wherein the disease is one that can be treated by regulating the Stat3 pathway or genes under control of Stat3, wherein the molecule comprises a human STAT3 sense strand-overhang, a human CpG(D19)-overhang and a human STAT3 antisense strand, wherein the human STAT3 sense strand-overhang comprises (a) an oligonucleotide having the nucleotides set forth in SEQ ID NO:18 that is the sense strand, (b) a C3 carbon chain or propanediol linker and (c) an oligonucleotide having the nucleotides set forth in SEQ ID NO:19 that is the overhang, wherein the human CpG(D19)-overhang comprises (a) an oligonucleotide having the nucleotides set forth in SEQ ID NO:16, (b) a C3 carbon chain or propanediol linker and (c) an oligonucleotide having the nucleotides set forth in SEQ ID NO:20 that is the overhang, wherein the human STAT3 antisense strand comprises an oligonucleotide having the nucleotides set forth in SEQ ID NO:5, wherein the modifications are selected from the group consisting of 2'F, 2'OMe, LNA, nucleotides and other modifications described herein, wherein the overhangs anneal to form a double stranded RNA, and wherein the sense strand and the antisense strand anneal to form a double stranded siRNA.

4. The method of claim 3, wherein the disease is selected from the group consisting of cancer, an infectious disease and an autoimmune disease.

\* \* \* \* \*